US006503703B1

(12) United States Patent
Palese et al.

(10) Patent No.: US 6,503,703 B1
(45) Date of Patent: Jan. 7, 2003

(54) IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

(75) Inventors: Peter M Palese, Leonia, NJ (US); Robert O'Neill, New York, NY (US); Ronald Harty, Bensalem, PA (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 09/636,791

(22) Filed: Aug. 11, 2000

Related U.S. Application Data

(63) Continuation-in-part of application No. 08/444,994, filed on May 19, 1995.
(60) Provisional application No. 60/148,263, filed on Aug. 11, 1999.

(51) Int. Cl.$^7$ .............................. C12Q 1/00; C12Q 1/70; G01N 33/52; G01N 33/53; G01N 33/531
(52) U.S. Cl. ..................... 435/5; 435/4; 435/6; 435/7.1; 435/7.4; 435/7.71; 435/7.8; 435/7.92; 435/7.94; 435/7.93; 435/7.95; 435/8
(58) Field of Search .............................. 435/4, 5, 6, 7.1, 435/7.4, 7.71, 7.8, 7.92, 7.93, 7.94, 7.95, 8

(56) References Cited

U.S. PATENT DOCUMENTS

| 5,110,906 A | 5/1992 | Maddon et al. |
| 5,738,985 A | 4/1998 | Miles et al. |
| 5,744,353 A | 4/1998 | Draetta et al. |

FOREIGN PATENT DOCUMENTS

| WO | WO-9532310 | * 11/1995 |
| WO | WO 97/12967 | 4/1997 |

OTHER PUBLICATIONS

Romanos et al. Gene 1995, vol. 152, pp. 137–138.*
Eric et al. Microbiological Reviews 1995, vol. 59, pp. 94–123.*
U.S. application No. 60/148,263, Palese et al., filed Aug. 8, 1999.
U.S. application No. 08/444,994, Palese et al., filed May 19, 1995.
Albagli et al., 1995, "The BTB/POZ domain: a new protein–protein interaction motif common to DNA–and actin–binding proteins", Cell Growth Diff. 6:1193–1198.
Baez et al., 1981, "Neucleotide sequence of the influenza A/duck/Alberta/60/76 virus NS RNA: conservation of the NS1/NS2 overlapping gene structure in a divergent influenza virus RNA segment", Virology 113:397–402.
Bardwell and Treisman, 1994, "The POZ domain: a conserved protein–protein interaction motif", Genes Dev. 8:1664–1677.

Barik and Banerjee, 1992, "Phosphorylation by cellular casein kinase II is essential for transcriptional activity of vesicular stomatitis virus phosphoprotein P", Proc. Natl. Acad. Sci. USA 89:6570–6574.
Barik and Banerjee, 1992, "Sequential phosphorylation of the phosphoprotein of vesicular stomatitis virus by cellular and viral protein kinases is essential for transcription activation", J. Virol. 66:1109–1118.
Baudin et al., 1994, "Structure of influenza virus RNP. I. Influenza virus nucleoprotein melts secondary structure in panhandle RNA and exposes the bases to the solvent", EMBO J. 13:3158–3165.
Bean, 1984, "Correlation of influenza A virus nucleoprotein genes with host species", Virology 133:438–442.
Beaton and Krug, 1986, "Transcription antitermination during influenza viral template RNA synthesis requires the nucleocapsid protein and the absence of a 5' capped end", Proc. Natl. Acad. Sci. USA 83:6282–6286.
Belanger et al., 1994, "Genetic and physical interactions between Srp1p and nuclear pore complex proteins Nup1p and Nup2p", J. Cell Biol. 126:619–630.
Benmansour et al., 1994, "The polymerase–associated protein (M1) and the matrix protein (M2) from a virulent and an avirulent strain of viral hemorrhagic septicemia virus (VHSV), a fish rhabdovirus", Virology 198:602–612.
Bennett et al., 1993, "Functional chimeras of the Rous sarcoma virus and human immunodeficiency virus gag proteins", J. Virol. 67:6487–6498.
Bennett et al., 1991, "Amino acids encoded downstream of gag are not required by Rous sarcoma virus protease during gag–mediated assembly", J. Virol. 65:272–280.
Bond, 1988, "Heat shock but not other stress inducers leads to the disruption of a sub–set of snRNPs and inhibition of *in vitro* splicing in HeLa cells", EMBO J. 7:3509–3518.

(List continued on next page.)

Primary Examiner—Ali R. Salimi
Assistant Examiner—Bao Qunhi
(74) Attorney, Agent, or Firm—Pennie & Edmonds LLP

(57) ABSTRACT

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection. The invention is based, in part, on the Applicants' discovery of novel interactions between viral proteins and a human host cell proteins. One of these host cell proteins, referred to herein as NPI-1, interacts with influenza virus protein NP. Also, host cell proteins, referred to herein as NS1I-1 and NS1-BP interact with influenza virus protein $NS_1$. In addition, host cell proteins containing WW domains that interact with viral proteins such as Rhabdoviral M protein are described. Compounds that interfere with the binding of the host cell and viral proteins, and inhibit viral replication can be useful for treating viral infection in vivo.

21 Claims, 44 Drawing Sheets

OTHER PUBLICATIONS

Figure 1A:
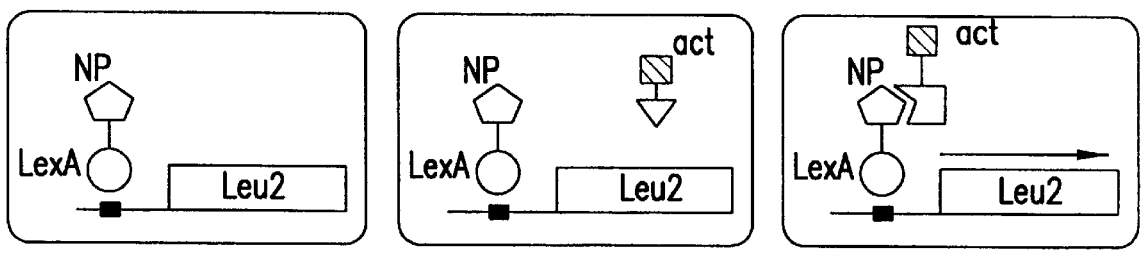

Bork and Doolittle, 1994, "*Drosophila kelch* motif is derived form a common enzyme fold", J. Mol. Biol. 236:1277–128.

Bork and Sudol, 1994, "The WW domain: a signalling site in dystrophin?", Trends Biochem. Sci. 19:531–533.

Brown et al., 1995, "Herpes simplex virus *trans*–regulatory protein ICP27 stabilizes and binds to 3' ends of labile mRNA", J. Virol. 69:7187–7195.

Buckler–White and Murphy, 1986, "Nucleotide sequence analysis of the nucleoprotein gene of an avian and a human influenza virus strain identifies two classes of nucleoproteins", Virology 55:345–355.

Bukreyev et al., 1995, "The complete nucleotide sequence of the Popp (1967) strain of Marburg virus: a comparison with the Musoke (1980) strain", Arch. Virol. 140:1589–1600.

Buonagurio et al., 1985, "Evolution of human influenza A viruses over 50 years: rapid, uniform rate of change in NS gene", Science 232:980–982.

Change–Yeh et al., 1991, "Identification of a novel murine IAP–promoted placenta–expressed gene", Nucl. Acids Res. 19:3667–3672.

Chelsky et al., 1989, "Sequence requirements for synthetic peptide–mediated translocation to the nucleus", Mol. Cell. Biol. 9:2487–2492.

Chen et al., 1997, "Characterization of the WW domain of human Yes–associated protein and its polyproline–containing ligands", J. Biol. Chem. 272:17070–17077.

Chen and Sudol, 1996, "Identification and characterization of protein ligands to the WW domain by Western ligand blotting", Techniques in Protein Chemistry VII, 7:3–12.

Chen and Sudol, 1995, "The WW domain of Yes–associated protein binds a proline–rich ligand that differs from the consensus established for Src homology 3–binding modules", Proc. Natl. Acad. Sci. USA 92:7819–7823.

Chen et al., 1995, "The BTB domain of *bric àbrac* mediates dimerization in vitro", Mol. Cell. Biol. 15:3424–3429 [retracted by Mol. Cell Biol. 17:6772 (1997)].

Chen et al., 1993, "Site–specific mutagenesis of *Drosophila* alcohol dehydrogenase: evidence for involvement of tyrosine–152 and lysine–156 in catalysis", Biochem. 32:3342–3346.

Chien et al., 1991, "The two–hybrid system: a method to identify and clone genes for proteins that interact with a protein of interest", Proc. Natl. Acad. Sci. USA 88:9578–9582.

Chong and Rose, 1994, "Interactions of normal and mutant vesicular stomatitis virus matrix protein in vivo", J. Virol. 67:407–414.

Cortes et al., 1994, "RAG–1 interacts with the repeated amino acid motif of the human homologue of the yeast protein SRP1" Proc. Natl. Acad. Sci. USA 91:7633–7637.

Craven et al., 1999, "Late domain function identified in the vesicular stomatitis virus M protein by use of rhabdovirus–retrovirus chimeras", J. Virol. 73:3359–3365.

Craven et al., 1993, "Necessity of the spacer peptide between CA and NC in the Rous sarcoma virus gag protein", J. Virol. 67:6246–6252.

Cuomo et al., 1994, "Rch1, a protein that specifically interacts with the RAG–1 recombination–activating protein", Proc. Natl. Acad. Sci. USA 91:6156–6160.

Cuomo et al., 1994, "Genes involved in V(D)J recombination", Meeting abstract F015, Keystone Symposium on Recombination.

Dalton & Treisman, 1992, "Characterization of SAP–1, a protein recruited by serum response factor to the c–*fos* serum response element", Cell 68:597–612.

de Hoop and Ab, 1992, "Import of proteins into peroxisomes and other microbodies", Biochem. J. 286:657–669.

De la Luna et al., 1995, "Influenza virus NS1 protein enhances the rate of translation initiation of viral mRNAs", J. Virol. 69:2427–2433.

Derossi et al., 1998, "Trojan peptides: the penetratin system for intracellular delivery", Trends Cell Biol. 8:84–87.

Devereux et al., 1984, "A comprehensive set of sequence analysis programs for the VAX", Nucl. Acids Res. 12:387–395.

Dhordain et al., 1995, "The BTB/POZ domain targets the LAZ3/BCL6 oncoprotein to nuclear dots and mediates homomerisation *in vivo*", Oncogene 11:2689–2697.

Dong et al., 1996, "Amino–terminal protein–protein interaction motif (POZ–domain) is responsible for activities of the promyelocytic leukemia zinc finger–retinoic acid receptor–α fusion protein", Proc. Natl.Acad. Sci. USA 93:3624–3629.

Du and Warren, 1997, "A functional interaction between the carboxy–terminal domain of RNA polymerase II and pre–mRNA splicing", J. Cell Biol. 136:5–18.

Durfee et al., 1993, "The retinoblastoma protein associates with the protein phosphatase type 1 catalytic subunit", Genes Dev. 7:555–569.

Einbond and Sudol, 1996, "Towards prediction of cognate complexes between the WW domain and proline–rich ligands", FEBS Lett. 384:1–8.

Enami et al., 1994, "Influenza virus NS1 protein stimulates translation of the M1 protein", J. Virol. 68:1433–1437.

Enami et al., 1990, "Introduction of site–specific mutations into the genome of influenza virus", Proc. Natl. Acad. Sci. USA 87:3802–3805.

Fakan, 1994, "Perichromatin fibrils are *in situ* forms of nascent transcripts", Trends Cell Biol. 4:86–90.

Fay et al., 1997, "Quantitative digital analysis of diffuse and concentrated nuclear distributions of nascent transcripts, SC35 and poly(A)", Exp. Cell Res. 231:27–37.

Fields and Sternglanz, 1994, "The two–hybrid system: an assay for protein–protein interactions", Trends Genet. 10:286–291.

Fortes et al., 1995, "Influenza virus NS1 protein alters the subnuclear localization of cellular splicing components", J. Gen. Virol. 76:1001–1007.

Fortes et al., 1994, "Influenza virus NS1 protein inhibits pre–mRNA splicing and blocks mRNA nucleocytoplasmic transport", EMBO J. 13:704–712.

Fu and Maniatis, 1990, "Factor required for mammalian spliceosome assembly is localized to discrete regions in the nucleus", Nature 343:437–441.

Gammelin et al., 1989, "Two subtypes of nucleoproteins (NP) of influenza A viruses", Virol. 170:71–80.

Gannon and Lane, 1990, "Interactions between SV40 T antigen and DNA polymerase α", New Biologist 2:84–92.

Garcia–Sastre et al., 1998, "Influenza A virus lacking the NS1 gene replicates in interferon–deficient systems", Virology 252:324–330.

Garnier et al., 1996, "WW domains and retrovirus budding", Nature 381:744–745.

Ge and Roeder, 1994, "Purification, cloning and characterization of a human coactivator, PC4, that mediates transcriptional activation of class II genes", Cell 78:513–523.
Ge et al., 1994, "Phosphorylation negatively regulates the function of coactivator PC4", Proc. Natl. Acad. Sci. USA 91:12691–12695.
Gill and Banerjee, 1986, "Complete nucleotide sequence of the matrix protein mRNA of vesicular stomatitis virus (New Jersey serotype)", Virology 150:308–312.
Goebel et al., 1990, "The complete DNA sequence of vaccinia virus", Virology 179:247–266 and 517–563.
Göttlinger et al., 1991, "Effect of mutations affecting the p6 gag protein on human immunodeficiency virus particle release", Proc. Natl. Acad. Sci. USA 88:3195–3199.
Greenspan et al., 1988, "Two nuclear location signals in the influenza virus NS1 nonstructural protein", J. Virol. 62:3020–3026.
Guthrie, 1991, "Messenger RNA splicing in yeast: clues to why the spliceosome is a ribonucleoprotein", Science 253:157–163.
Gyuris et al., 1993, "Cdi1, a human G1 and S phase protein phosphatase that associates with Cdk2", Cell 75:791–803.
Hall et al., 1984, "Targeting of E. coli β–galactosidase to the nucleus in yeast", Cell 36:1057–1065.
Hardy and Sandri–Goldin, 1994, "Herpes simplex virus inhibits host cell splicing, and regulatory protein ICP27 is required for this effect", J. Virol. 68:7790–7799.
Harty et al., 1999, "A proline–rich motif within the matrix protein of vesicular stomatitis virus and rabies virus interacts with WW domains of cellular proteins: implications for viral budding", J. Virol. 73:2921–2929.
Hatada and Fukada, 1992, "Binding of influenza A virus NS1 protein to dsRNA in vitro", J. Gen. Virol. 73:3325–3329.
Hatada et al., 1992, "Specific binding of influenza A virus NS1 protein to the virus minus–sense RNA in vitro", J. Gen. Virol 73:17–25.
Hatada et al., 1990, "Analysis of influenza A virus temperature–sensitive mutants with mutations in RNA segment 8", J. Gen. Virol. 71:1283–1292.
Hentze, 1994, "Enzymes as RNA–binding proteins: a role for (di)nucleotide–binding domains?", Trends Biochem. Sci. 19:101–103.
Hernandez et al., 1997, "ENC–1: a novel mammalian kelch–related gene specifically expressed in the nervous system encodes an actin–binding protein", J. Neurosci. 17:3038–3051.
Honda et al., 1988, "RNA polymerase of influenza virus: role of NP in RNA chain elongation", J. Biochem. 104:1021–1026.
Huang et al., 1995, "p6Gag is required for particle production from full–length human immunodeficiency virus type 1molecular clones expressing protease", J. Virol. 69:6810–6818.
Huang et al., 1990, "Determination of influenza virus proteins required for genome replication", J. Virol. 64:5669–5673.
Ito et al., 1991, "Novel thioether bond revealed by a 1.7 Å crystal structure of galactose oxidase", Nature 350:87–90.
Jackson et al., 1982, "Influenza virus RNA is synthesized at fixed sites in the nucleus", Nature 296:366–368.
Joklik et al. (eds.), 1992, "Antiviral chemotherapy, interferon and vaccines" in: Zinsser Microbiology, Appleton and Lange, Norwalk, CT, pp. 854–861.

Justice et al., 1995, "Membrane vesiculation function and exocytosis of wild–type and mutant matrix proteins of vesicular stomatitis virus", J. Virol. 69:3156–3160.
Kalpana et al., 1994, "Binding and stimulation of HIV–1 integrase by a human homolog of yeast transcription factor SNF5", Science 266:2002–2006.
Kaptur et al., 1995, "Assembly functions of vesicular stomatitis virus matrix protein are not disrupted by mutations at major sites of phosphorylation", Virology 206:894–903.
Kiuchi and Roy, 1984, "Comparison of the primary sequence of spring viremia of carp virus M protein with that of vesicular stomatitis virus", Virology 134:238–243.
Koennecke et al., 1981, "Isolation and properties of a temperature–sensitive mutant (ts 412) of an influenza A virus recombinant with a ts lesion in the gene coding for the nonstructural protein", Virology 110:16–25.
Konarska and Sharp, 1987, "Interactions between small nuclear ribonucleoprotein particles in formation of spliceosomes", Cell 49:763–774.
Kotwal and Moss, 1988, "Analysis of a large cluster of nonessential genes deleted from a vaccinia virus terminal transposition mutant", Virology 167:524–537.
Krug and Etkind, 1973, "Cytoplasmic and nuclear virus–specific proteins in influenza virus–infected MDCK cells", Virology 56:334–348.
Lahiri and Thomas, 1986, "A cDNA clone of the hnRNP C proteins and its homology with the single–stranded DNA binding protein UP2", Nucl. Acids Res. 14:4077–4094.
Lamb, 1989, "Genes and Proteins of the Influenza Viruses", in: The Influenza Viruses, Krug, ed., Plenum Press, NY, NY, pp. 1–87.
Lawrence, 1989, Henderson's Dictionary of Biological Terms, $10^{th}$ ed., John Wiley & Sons, New York, NY p. 460.
Lazarowitz et al., 1971, "Influenza virus structural and nonstructural proteins in infected cells and their plasma membranes", Virol. 46:830–843.
Lee et al., 1996, "Crystal structure of the conserved core of HIV–1 Nef complexed with a Src family SH3 domain", Cell 85:931–942.
Lee et al., 1995, "A single amino acid in the SH3 domain of Hck determines its high affinity and specificity in binding to HIV–1 Nef protein", EMBO J. 14:5006–5015.
Leenders et al., 1994, "Molecular cloning and amino acid sequence of the porcine 17 β–estradiol dehydrogenase", Eur. J. Biochem. 222:221–227.
Lenard, 1996, "Negative–strand virus M and retrovirus MA proteins: all in a family?", Virology 216:289–298.
Lenard and Vanderoef, 1990, "Localization of the membrane–associated region of vesicular stomatitis virus M protein at the N terminus, using the hydrophobic, photoreactive probe $^{125}$I–TID", J. Virol. 64:3486–3491.
Li et al., 1993, "Viral liposomes released from insect cells infected with recombinant baculovirus expressing the matrix protein of vesicular stomatitis virus", J. Virol. 67:4415–4420.
Longnecker et al., 1991, "An Epstein–Barr virus protein associated with cell growth transformation interacts with a tyrosine kinase", J. Virol. 65:3681–3692.
Lu et al., 1995, "Binding of the influenza virus NS1 protein to double–stranded RNA inhibits the activation of the protein kinase that phosphorylates the eIF–2 translation initiation factor", Virol. 214:222–228.
Lu et al., 1994, "The influenza virus NS1 protein: a novel inhibitor of pre–mRNA splicing", Genes Dev. 8:1817–1828.

Luban et al., 1993, "Human immunodeficiency virus type 1 Gag protein binds to cyclophilins A and B", Cell 73:1067–1078.

Ludwig et al., 1991, "Phylogenetic relationship of the non-structural (NS) genes of influenza A viruses", Virology 183:566–577.

Lyles et al., 1992, "Subunit interactions of vesicular stomatitis virus envelope glycoprotein stabilized by binding to viral matrix protein", J. Virol. 66:349–358.

Macias et al., 1996, "Structure of the WW domain of a kinase–associated protein complexed with a proline–rich peptide", Nature 382:646–649.

Martin, 1995, Dictionary of Endocrinology and Related Biomedical Sciences, Oxford University Press, New York, NY p. 623.

Massung et al., 1994, "Analysis of the complete genome of smallpox variola major virus strain Bangladesh–1975", Virology 201:215–240.

Massung et al., 1993, "DNA sequence anlaysis of conserved and unique regions of swinepox virus: identification of genetic elements supporting phenotypic observations including a novel G protein–coupled receptor homologue", Virology 197:511–528.

McCrea et al., 1991, "A homolog of the *armadillo* protein in *Drosophila* (plakoglobin) associated with E–cadherin", Science 254:1359–1361.

McCreedy and Lyles, 1989, "Distribution of M protein and nucleocapsid protein of vesicular stomatitis virus in infected cell plasma membranes", Virus Res. 14:189–206.

McLauchlan et al., 1992, "Herpes simplex virus IE63 acts at the posttranscriptional level to stimulate viral mRNAB 3' processing", J. Virol. 66:6939–6945.

Mebatsion et al., 1996, "Budding of rabies virus particles in the absence of the spike glycoprotein", Cell 84:941–951.

Merriam–Webster's Medical Desk Dictionary, 1993, Merriam–Webster, Inc., Springfield, MA, p. 605.

Nagase et al., 1995, "Prediction of the coding sequences of unidentified human genes. IV. The coding sequences of 40 new genes (KIAA0121–KIAA0160) deduced by anaylsis of cDNA clones from human cell line KG–1", DNA Res. 2:167–174; 199–210.

Nakada et al., 1984, "Complete nucleotide sequence of the influenza C/California/78 virus nucleoprotein gene", Virus Res. 1:433–441.

Newcomb et al., 1982, "In vitro reassembly of vesicular stomatitis virus skeletons", J. Virol. 41:1055–1062.

Norton et al., 1987, "Infectious influenza A and B virus variants with long carboxyl terminal deletions in the NS1 polypeptides", Virol. 156:204–213.

O'Neill et al., 1998, "The influenza virus NEP (NS2 protein) mediates the nuclear export of viral ribonucleoproteins", EMBO J. 17:288–296.

O'Neill et al., 1995, "Nuclear import of influenza virus RNA can be mediated by viral nucleoprotein and transport factors required for protein import", J. Biol. Chem. 270:22701–22704.

O'Neill and Palese, 1995, "NPI–1, the human homolog of SRP–1, interacts with influenza virus nucleoprotein", Virology 206:116–125.

O'Neill and Palese, 1994, "Cis–acting signals and trans–acting factors involved in influenza virus RNA synthesis", Chem. Abstr. 122:198, abstr. 124020p.

O'Neill and Palese, 1994, "*Cis*–acting signals and *trans*–acting factors involved in influenza virus RNA synthesis", Infect. Agents Dis. 3:77–84.

Pal and Wagner, 1987, "Rhabdovirus membrane and maturation", In: *The Rhabdoviruses*, Wagner, ed., Plenum Press, NY, NY, pp. 75–128.

Palese et al., 1997, "Host–viral protein–protein interactions in influenza virus replication", Society for General Microbiology, Symposium 55, Molecular Aspects of Host–Pathogen Interactions, McCrae et al., eds., pp. 326–340.

Palese et al., 1996, "Host cell and influenza virus protein interactions", In: The First Shizuoka Forum on Health and Longevity, pp. 196–199 (reprint pp. 1–4).

Parent et al., 1995, "Positionally independent and exchangeable late budding functions of the Rous sarcoma virus and human immunodeficiency virus Gag proteins", J. Virol. 69:5455–5460.

Parvin et al., 1989, "Promoter analysis of influenza virus RNA polymerase", J. Virol. 63:5142–5152.

Peelman et al., 1995, "The *BAT1* gene in the MHC encodes an evolutionarily conserved putative nuclear RNA helicase of the DEAD family", Genomics 26:210–218.

Peifer et al., 1994, "A repeating amino acid motif shared by proteins with diverse cellular roles", Cell 76:789–791.

Perkus et al., 1991, "Deletion of 55 open reading frames from the termini of vaccinia virus", Virology 180:406–410.

Persson et al., 1991, "Characteristics of short–chain alcohol dehydrogenases and related enzymes", Eur. J. Biochem. 200:537–543.

Phelan and Clements, 1997, "Herpes simplex virus type 1 immediate early protein IE63 shuttles between nuclear compartments and the cytoplasm", J. Gen. Virol. 78:3327–3331.

Phelan et al., 1993, "A herpes simplex virus type 1 immediate–early gene product, IE63, regulates small nuclear ribonucleoprotein distribution", Proc. Natl. Acad. Sci. USA 90:9056–9060.

Puffer et al., 1997, "Equine infectious anemia virus utilizes a YXXL motif within the late assembly domain of the gag p9 protein", J. Virol. 71:6541–6546.

Qiu et al., 1995, "The influenza virus NS1 protein binds to a specific region in human U6 snRNA and inhibits U6–U2 and U6–U4 snRNA interactions during splicing", RNA 1:304–316.

Qiu and Krug, 1994, "The influenza virus NS1 protein is a poly(A)–binding protein that inhibits nuclear export of mRNAs containing poly(A)", J. Virol. 68:2425–2432.

Rayssiguier et al., 1986, "Cloning of rabies virus matrix protein mRNA and determination of its amino acid sequence", Virus Res. 5:177–190.

Riggleman et al., 1989, "Molecular analysis of the *armadillo* locus: uniformly distributed transcripts and a protein with novel internal repeats are associated with a *Drosophila* segment polarity gene", Genes Dev. 3:96–113.

Robinson and Cooley, 1997, "*Drosophila* kelch is an oligomeric ring canal actin organizer", J. Cell Biol. 138:799–810.

Rose and Gallione, 1981, "Nucleotide sequences of the mRNA's encoding the vesicular stomatitis virus G and M proteins determined from cDNA clones containing the complete coding regions", J. Virol. 39:519–528.

Sanchez et al., 1993, "Sequence analysis of the Ebola virus genome: organization, genetic elements, and comparison with the genome of Marburg virus", Virus Res. 29:215–240.

Sandri–Goldin et al., 1995, "The C–terminal repressor region of Herpes simplex virus type 1 ICP27 is required for the redistribution of small nuclear ribonuclearprotein particles and splicing factor SC35; however, these alterations are not sufficient to inhibit host cell splicing", J. Virol. 69:6063–6076.

Schmid et al., 1994, "Three–dimensional structure of a single filament in the *Limulus* acrosomal bundle: scruin binds to homologous helix–loop–beta motifs in actin", J. Cell Biol. 124:341–350.

Scholtissek, 1986, "Molecular biological background of the species and organ specificity of influenza A viruses", Angew. Chem. Int. Ed. Engl. 25:47–56.

Scholtissek et al., 1985, "The nucleoprotein as a possible major factor in determining host specificity of influenza H3N2 viruses", Virol. 147:287–294.

Scholtissek et al., 1978, "Host range recombinants of fowl plague (influenza A) virus", Virol. 91:79–85.

Shapiro and Krug, 1988, "Influenza virus RNA replication in vitro: synthesis of viral template RNAs and virion RNAs in the absence of an added primer", J. Virol. 62:2285–2290.

Sharp, 1994, "Split genes and RNA splicing", Cell 77:805–815.

Shimizu et al., 1983, "Temperature–sensitive mutants of influenza A/Udorn/72 (H3N2) virus. III. Genetic analysis of temperature–dependent host range mutants", Virology 124:35–44.

Singer and Green, 1997, "Compartmentalization of eukaryotic gene expression: causes and effects", Cell 91:291–294.

Skorko et al., 1991, "Influenza A virus *in vitro* transcription: roles of NS1 and NP proteins in regulating RNA synthesis", Virology 180:668–677.

Smith and Inglis, 1985, "Regulated production of an influenza virus spliced mRNA mediated by virus–specific products", EMBO J. 4:2313–2319.

Snyder et al., 1990, "A 36 nucleotide deletion mutation in the coding region of the NS1 gene of an influenza virus RNA segment 8 specifies a temperature–dependent host–range phenotype", Virus Res. 15:69–84.

Soliman et al., 1997, "Shuttling of the herpes simplex virus type 1 regulatory protein ICP27 between the nucleus and cytoplasm mediates the expression of late proteins", J. Virol. 71:9188–9197.

Spector, 1993, "Macromolecular domains within the cell nucleus", Annu. Rev. Cell Biol. 9:265–315.

Spector et al., 1991, "Associations between distinct pre–mRNA splicing components and the cell nucleus", EMBO J. 10:3467–3481.

Staub et al., 1996, "WW domains of Nedd4 bind to the proline–rich PY motifs in the epithelial $Na^+$ channel deleted in Liddle's syndrome", EMBO J. 15:2371–2380.

Stedman's Medical Dictionary, 1995, $26^{th}$ Ed., Williams & Wilkins, Baltimore, MD, pp. 1508–1510.

Sudol, 1996, "Structure and function of the WW domain", In: *Prog. Biophys. Mol. Biol.*, vol. 65, Blundell et al., eds., Elsevier Science Ltd., Great Britain, pp. 113–132.

Sudol et al., 1995, "Characterization of the mammalian YAP (Yes–associated protein) gene and its role in defining a novel protein module, the WW domain", J. Biol. Chem. 270:14733–14741.

Sudol, 1994, "Yes–associated protein (YAP65) is a proline–rich phosphoprotein that binds to the SH3 domain of the Yes proto–oncogene product", Oncogene 9:2145–2152.

Sugiura et al., 1997, "Expression cloning and intracellular localization of a human ZF5 homologue", Biochem. Biophys. Acta 1352:23–26.

Treanor et al., 1989, "The B allele of the NS gene of avian influenza viruses, but not the A allele, attenuates a human influenza A virus for squirrel monkeys", Virology 171:1–9.

Upton et al., 1990, "Myxoma virus and malignant rabbit fibroma virus encode a serpin–like protein important for virus virulence", Virology 179:618–631.

Valcarel et al., 1991, "Regulated M1 mRNA splicing in influenza virus–infected cells", J. Gen. Virol. 72:1301–1308.

Varkey et al., 1995, "The *Caenorhabditis elegans* spe–26 gene is necessary to form spermatids and encodes a protein similar to the actin–associated proteins kelch and scruin", Genes Dev. 9:1074–1086.

von Bü low et al., 1995, "Molecular nature of calicin, a major basic protein of the mammalian sperm head cytoskeleton", Exp. Cell Res. 219:407–413.

Vojtek et al., 1993, "Mammalian Ras interacts directly with the serine/threonine kinase Raf", Cell 74:205–214.

Wang et al., 1997, "The NPI–1/NPI–3 (karyopherin $\alpha$) binding site on the influenza A virus nucleoprotein NP is a nonconventional nuclear localization signal", J. Virol. 71:1850–1856.

Way et al., 1995, "$\beta$–scruin, a homologue of the actin crosslinking protein scruin, is localized to the acrosomal vesicle of *Limulus* sperm", J. Cell Sci. 108:3155–3162.

Way et al., 1995, "Sequence and domain organization of scruin, an actin–cross–linking protein in the acrosomal process of *Limulus* sperm", J. Cell Biol. 128:51–60.

Weldon et al., 1990, "Incorporation of chimeric Gag protein into retroviral particles", J. Virol. 64:4169–4179.

Wills et al., 1994, "An assembly domain of the Rous sarcoma virus Gag protein required late in budding", J. Virol. 68:6605–6618.

Wills et al., 1991, "Suppression of retroviral MA deletions by the amino–terminal membrane–binding domain of $p60^{src}$", J. Virol. 65:3804–3812.

Wills and Craven, 1991, "Form, function, and use of retroviral gag proteins", AIDS 5:639–654.

Wolff et al., 1998, "NS1–binding protein (NS1–BP): a novel human protein that interacts with the influenza A virus nonstructural NS1 protein is relocalized in the nuclei of infected cells", J. Virol. 72:7170–7180 [official publication date (print and internet versions) is Aug. 7, 1998].

Wolff et al., 1996, "Interaction cloning of NS1–I, a human protein that binds to the nonstructural NS1 proteins of influenza A and B viruses", J. Virol. 70:5363–5372.

Wolstenholme et al., 1980, "Influenza virus–specific RNA and protein syntheses in cells infected with temperature–sensitive mutants defective in the genome segment encoding nonstructural proteins", J. Virol. 35:1–7.

Xue and Cooley, 1993, "*kelch* encodes a component of intercellular bridges in Drosophila egg chambers", Cell 72:681–693.

Yano et al., 1994, "Yeast Srp1p has homology to armadillo/plakoglobin/$\beta$–catenin and participates in apparently multiple nuclear functions including the maintenance of the nucleolar structure", Proc. Natl. Acad. Sci. USA 91:6880–6884.

Yano et al., 1992, "Cloning and characterization of *SRP1*, a suppressor of temperature–sensitive RNA polymerase I mutations, in *Saccharomyces cerevisiae*", Mol. Cell Biol. 12:5640–5651.

Ye et al., 1994, "Membrane–binding domains and cytopathogenesis of the matrix protein of vesicular stomatitis virus", J. Virol. 68:7386–7396.

Young et al., 1983, "Efficient expression of influenza virus NS1 nonstructural proteins in Escherichia coli", Proc. Natl. Acad. Sci. USA 80:6105–6109.

Yuryev et al., 1996, "The C–terminal domain of the largest subunit of RNA polymerase II interacts with a novel set of serine/arginine–rich proteins", Proc. Natl. Acad. Sci. USA 93:6975–6980.

Zakowski et al. 1981, "Role of matrix protein in assembling the membrane of vesicular stomatitis virus: reconstitution of matrix protein with negatively charged phospholipid vesicles", Biochem. 20:3902–3907.

Zakowski and Wagner, 1980, "Localization of membrane–associated proteins in vesicular stomatitis virus by use of hydrophobic membrane probes and cross–linking reagents", J. Virol. 36:93–102.

Zervos et al., 1993, "Mxi1, a protein that specifically interacts with Max to bind Myc–Max recognition sites", Cell 72:223–232.

Zollman et al., 1994, "The BTB domain, found primarily in zinc finger proteins, defines an evolutionarily conserved family that includes several developmentally regulated genes in *Drosophila*", Proc. Natl. Acad. Sci. USA 91:10717–10721.

* cited by examiner

```
                    20                    40                    60
CTAACTTCAG CGGTGGCACC GGGATCGGTT GCCTTGAGCC TGAAATATGA CCACCCCAGG
                                                     M  T    T    P    G>

80                   100                   120
AAAAGAGAAC TTTCGCCTGA AAAGTTACAA GAACAAATCT CTGAATCCCG ATGAGATGCG
 K    E    N    F    R    L    K    S    Y    K    N    K    S    L    N    P    D    E    M    R>

140                   160                   180
CAGGAGGAGG GAGGAAGAAG GACTGCAGTT ACGAAAGCAG AAAAGAGAAG AGCAGTTATT
 R    R    R    E    E    E    G    L    Q    L    R    K    Q    K    R    E    E    Q    L    F>

200                   220                   240
CAAGCGGAGA AATGTTGCTA CAGCAGAAGA AGAAACAGAA GAAGAAGTTA TGTCAGATGG
 K    R    R    N    V    A    T    A    E    E    E    T    E    E    E    V    M    S    D    G>

260                   280                   300
AGGCTTTCAT GAGGCTCAGA TTAGTAACAT GGAGATGGCA CCAGGTGGTG TCATCACTTC
 G    F    H    E    A    Q    I    S    N    M    E    M    A    P    G    G    V    I    T    S>

320                   340                   360
TGACATGATT GAGATGATAT TTTCCAAAAG CCCAGAGCAA CAGCTTTCAG CAACACAGAA
 D    M    I    E    M    I    F    S    K    S    P    E    Q    Q    L    S    A    T    Q    K>

380                   400                   420
ATTCAGGAAG CTGCTTTCAA AAGAACCTAA CCCTCCTATT GATGAAGTTA TCAGCACACC
 F    R    K    L    L    S    K    E    P    N    P    P    I    D    E    V    I    S    T    P>

440                   460                   480
AGGAGTAGTG GCCAGGTTTG TGGAGTTCCT CAAACGAAAA GAGAATTGTT CACTGCAGTT
 G    V    V    A    R    F    V    E    F    L    K    R    K    E    N    C    S    L    Q    F>

500                   520                   540
TGAATCAGCT TGGGTACTGA CAAATATTGC TTCAGGAAAT TCTCTTCAGA CCCGAATTGT
 E    S    A    W    V    L    T    N    I    A    S    G    N    S    L    Q    T    R    I    V>

560                   580                   600
GATTCAGGCA AGAGCTGTGC CCATCTTCAT AGAGTTGCTC AGCTCAGAGT TTGAAGATGT
 I    Q    A    R    A    V    P    I    F    I    E    L    L    S    S    E    F    E    D    V>

620                   640                   660
CCAGGAACAG GCAGTCTGGG CTCTTGGCAA CATTGCTGGA GATAGTACCA TGTGCAGGGA
 Q    E    Q    A    V    W    A    L    G    N    I    A    G    D    S    T    M    C    R    D>

680                   700                   720
CTATGTCTTA GACTGCAATA TCCTTCCCCC TCTTTTGCAG TTATTTTCAA AGCAAAACCG
 Y    V    L    D    C    N    I    L    P    P    L    L    Q    L    F    S    K    Q    N    R>

740                   760                   780
CCTGACCATG ACCCGGAATG CAGTATGGGC TTTGTCTAAT CTCTGTAGAG GGAAAAGTCC
 L    T    M    T    R    N    A    V    W    A    L    S    N    L    C    R    G    K    S    P>
```

FIG.2A

```
                600                    820                    840
ACCTCCAGAA TTTGCAAAGG TTTCTCCATG TCTGAATGTG CTTTCCTGGT TGCTGTTTGT
 P  P  E    F  A  K   V  S  P  C   L  N  V   L  S  W    L  L  F  V>

860                    880                    900
CAGTGACACT GATGTACTGG CTGATGCCTG CTGGGCCCTC TCATATCTAT CAGATGGACC
 S  D  T    D  V  L   A  D  A  C   W  A  L   S  Y  L    S  D  G  P>

920                    940                    960
CAATGATAAA ATTCAAGCGG TCATCGATGC GGGAGTATGT AGGAGACTTG TGGAACTGCT
 N  D  K    I  Q  A   V  I  D  A   G  V  C    R  R  L   V  E  L  L>

980                   1000                   1020
GATGCATAAT GATTATAAAG TGGTTTCTCC TGCTTTGCGA GCTGTGGGAA ACATTGTCAC
 M  H  N    D  Y  K   V  V  S  P   A  L  R    A  V  G   N  I  V  T>

1040                   1060                   1080
AGGGGATGAT ATTCAGACAC AGGTAATTCT GAATTGCTCA GCTCTGCAGA GTTTATTGCA
 G  D  D    I  Q  T   Q  V  I  L   N  C  S    A  L  Q   S  L  L  H>

1100                   1120                   1140
TTTGCTGAGT AGCCCAAAGG AATCTATCAA AAAGGAAGCA TGTTGGACGA TATCTAATAT
 L  L  S    S  P  K   E  S  I  K   K  E  A    C  W  T   I  S  N  I>

1160                   1180                   1200
TACAGCTGGA AATAGGGCAC AGATCCAGAC TGTGATAGAT GCCAACATTT TCCCAGCCCT
 T  A  G    N  R  A   Q  I  Q  T   V  I  D    A  N  I   F  P  A  L>

1220                   1240                   1260
CATTAGTATT TTACAAACTG CTGAATTTCG GACAAGAAAA GAAGCAGCTT GGGCCATCAC
 I  S  I    L  Q  T   A  E  F  R   T  R  K    E  A  A   W  A  I  T>

1280                   1300                   1320
AAATGCAACT TCTGGAGGAT CAGCTGAACA GATCAAGTAC CTAGTAGAAC TGGGTTGTAT
 N  A  T    S  G  G   S  A  E  Q   I  K  Y    L  V  E   L  G  C  I>

1340                   1360                   1380
CAAGCCGCTC TGTGATCTCC TCACGGTCAT GGACTCTAAG ATTGTACAGG TTGCCCTAAA
 K  P  L    C  D  L   L  T  V  M   D  S  K    I  V  Q   V  A  L  N>

1400                   1420                   1440
TGGCTTGGAA AATATCCTGA GGCTTGGAGA ACAGGAAGCC AAAAGGAACG GCACTGGCAT
 G  L  E    N  I  L   R  L  G  E   Q  E  A    K  R  N   G  T  G  I>

1460                   1480                   1500
TAACCCTTAC TGTGCTTTGA TTGAAGAAGC TTATGGTCTG GATAAAATTG AGTTCTTACA
 N  P  Y    C  A  L   I  E  E  A   Y  G  L    D  K  I   E  F  L  Q>

1520                   1540                   1560
GAGTCATGAA AACCAGGAGA TCTACCAAAA GGCCTTTGAT CTTATTGAGC ATTACTTCGG
 S  H  E    N  Q  E   I  Y  Q  K   A  F  D    L  I  E   H  Y  F  G>

1580                   1600                   1620
GACCGAAGAT GAAGACAGCA GCATTGCACC CCAGGTTGAC CTTAACCAGC AGCAGTACAT
 T  E  D    E  D  S   S  I  A  P   Q  V  D    L  N  Q   Q  Q  Y  I>
```

FIG.2B

```
                1640                   1660                    1680
CTTCCAACAG TGTGAGGCTC CTATGGAAGG TTTCCAGCTT TGAAGCAATA CTCTGCTTTC
 F  Q  Q    C  E  A   P  M  E  G  F  Q  L>

1700                   1720                    1740
ACGTACCTGT GCTCAGACCA GGCTACCCAG TCGAGTCCTC TTGTGGAGCC CACAGTCCTC 1760                   1780                    1800
ATGGAGCTAA CTTCTCAAAT GTTTTCCATA ATACTGTTTG CGCTCATTTG CTTGCCTTGC 1820                   1840                    1860
GCACCTGCTC TCTTACACAC ATCTGGAAAA CCTCCGGCTC TCTGTGGTGG GATACCCTTC 1880                   1900                    1920
TAATAAAAGG GTAACCAGAA CGGCCCACTC TCTTTTACGG AAAAATCCCT AGGCTTTGGA 1940                   1960                    1980
GATCCGCACT TACATTAGAG TTATGGGAAT ATACACATAT TAATGTGGCT CCCTTTTTCT 2000                   2020                    2040
TGTGGGGGAA TAAAAGAGGA CTCCTCCTCA TTCCCTTTAA CATGGGGGAA AAAACTGACA 2060                   2080                    2100
TTAAAAGATG AGACTAAATC TTTATCTTGA ATTTTACACA ACTACTTACG ACAAGGGAGA 2120                   2140                    2160
TGTTTAGACC TGTTGGTATA CTTCAGAGTA CTTTTCATGA GTTCTTCCAC AGTGAACCCT 2180                   2200                    2220
TGGATTACCT GGTGGCTTTT TCTAGCCAGA TTGCATTAAT CCTTACTGAG ATTGGATGGT 2240                   2260                    2280
TTTCTTTCCT CTATTGGCGC CATTCTTCAG ATATTAAAGT TAAACCATCC ACTCCCTCAC 2300                   2320                    2340
CTTCAGCCTT CAGTGAATGT GCTTTCTAGT TGTCAGGAAT GCTGAAGAAT TAACACTTTG 2360                   2380                    2400
ACTCCTAAAT GTGATACTGG TGGGTAAGAG CAGGGCACAT TTAATTTGTT CGCTTTTGCT 2420                   2440                    2460
TCTCTTTGGT CTGGGCACAT TTAATTTGTT CGCTTTTGCT TCTCTTTGGT CTTTTCGAAT 2480                   2500                    2520
ACTTAGTAAT CGAAAACCAT ATCCTGTAAT TTAATAAAAA AAACTAAGGA CGAAAAAACC 2540                   2560                    2580
CCTCCAATTT TCCCAAATGC AATCAGTGTA ACTAGGGGCT GTGTTTCTGC ATTAAAATAA 2600                   2620                    2640
ATGTTTCAGG CTTTGTGGTC CTGATCAAGG TCCTCATTAA AAAATTGGAG TTCACCCTAG 2660                   2680                    2700
GCTTTTCCCC TCTGTGACTG GCAGATAACA CATACTTTTG AAAGTAACTT TGGGATTTTT
```

FIG.2C

```
          2720                2740                2760
TTTCTTAGGT GCAGCTCGAT TCTAATCTTT TCATGCTGCA CACGATTCCT TTAATCGATA 2780                2800                2820
GCATCCTTAT CTGAAAGAAA TAACCATCTT CTCAACATGA CCTGCTTAAC CCAAATAAGA 2840                2860                2880
ACAGTGATCT TATAACCTCA TTGTTTCCTA ATCTATTTTA TTTCATCTCC TGCTAGTACT 2900                2920                2940
GTGCCGCTTC CCCCTCCCCC CACACAAAAT AAAAACAGTA TCTCGCTTCT GGCTCATTTT
```

FIG.2D

```
                                                     1           12
NPI-1                                           MTTPGKENFRLK
                                                |:     |||  .
SRP1                                         MDNGTDSSTSKEVPEYRRT
         13                                                    58
NPI-1    SYKWKS-LNPDVMRRRREEEGLQLRKLKREEQLFKRRNVVTAEEETE
         ||||||  ||||  ||||||·|  |||||  ||||·|  ||||  |·|·|·||
SRP1     HFKHKGRFSADELRRRRDTQQVELRKAKRDEALAKRRNFIPFTDGAD
         53                             .                     105
NPI-1    EEVHSDGGFHEAQISNHEHAPGGVITSDHIEHIFSKSPEQQLSATQK
         ·|  ·|||  ··|    ||··  ·  |||·|  |  |··  ||||||| |
SRP1     SDEEDESSVSADQQFYSQLQQ---ELPQMTQQLHSDDHQEQLSATVK
         106                                                  150
NPI-1    FRKLLSKEPDPPIDE-VISTPGVVARFVFFLKR-KEHCSLQFESANV      |
         ||::||:|.  ||||  |:   :|||:|:|||::   ::    ||:|:||.  |Repeat #1
SRP1     FRQILSREHRPPID--VVIQAGVVPRLVEFHRE-HQPEMLQLEAANA      |
         151                                                  192
NPI-1    LTNIASGNSLQTRI--VIQARAV-PIFIELLSS-ESEDVQE-QAVKA      |
         ||||||·|  ||::  |:||  ||  |:||:||  :  ·|  :|:|  ||:|| |Repeat #2
SRP1     LTNIASGTSAQTKV--VVDADAV-PLFIQLLYY-GSVEVKE-QAIKA      |
         193                                                  235
NPI-1    LGNIAGDSTHCRDY--VLDCNIL-PPLLQLFSKQNRLTHTR-NAVKA      |
         |||:|||||  ·|||  |||||  :   |:|  ||:.  |:  ::·|   ·|·|: |Repeat #3
SRP1     LGNVAGDSTDYRDY--VLQCNAM-EPILGLFNS-HKPSLTR-TATWT      |
         236                                                  277
NPI-1    LSNLCRGKSPPPEF--AKVSPCL-NVLSWLLFV-SDTDVLA-DACWA      |
         ||||||||·|·|::   :   ||·  |  ·|:  |::   ||:·|·   |||| |Repeat #4
SRP1     LSNLCPGKKPQPDW--SVVSQAL-PTLAKLIYS-HDTETLV-DACWA      |
         278                                                  318
NPI-1    LSYLSDGPNDKIQA---VIDAEYVET-VELLMH-NDYKVVS-PALRA      |
         :|||||||::  |||     |||·  ·   ||||  |  :·    |  :  ||||| |Repeat #5
```

FIG.3A

```
SRP1   ISYLSDGPQEAIQA---VIDVRIPKRLVELLSH-ESTLVQT-PALRA    |
       319                                        360
NPI-1  VGHIVTGDDIQTQV---ILNCSALQSLLHLLSS-PKESIKK-EACWT    |
       ||||||:|:||||    ::|  :.|.:| ||||  |||:|||  |||||  |Repeat #6
SRP1   VGNIVTGHDLQTQV---VINAGVLPALRLLLSS-PKENIKK-EACWT    |
       361                                        402
NPI-1  ISHITAGNRAQIQT---VIDANIFPALISILQT-AEFRTRK-EAAWA    |
       ||||||||  .|||:   |||||::|:|:..:|:. ||::|:| || ||  |Repeat #7
SRP1   ISNITAGNTEQIQA---VIDANLIPPLVKLLEV-AEYKTKK-EACWA    |
       403                                        445
NPI-1  ITNATSGG--SAEQIKYLVELGCIKPLCDLLTV-HDSKIVQ-VALNG    |
       |:||:|||   .::  |:|||. ||||||||||.:  |:::|::  |:|::  |Repeat #8
SRP1   ISHASSGGLQRPDIIRYLVSQGCIKPLCDLLEI-ADNRIIE-VTLDA    |
       406                                        490
NPI-1  LEHILRLGEQEAKRNGTGINPYCALIEEAYGLDKIEFL-LSHENQEI
       ||||||:||.:  .  .|  .||    .:||.| |::|| |    :||:.|
SRP1   LEHILKMGEADKEARGLNINEHADEIEKAGGMEKI-FNCQQNENDKI
       491                                     ---
NPI-1  YQKAFDLIEHYFGTEDE--DSSIAPQVDQNQQQYIFQQCEAPMEGFQL
       |:||:.:||  |||.|::    |.:::||
SRP1   YEKAYKIIETYFGEEEDAVDETHAPQNAGNTFGFGSNVNQQFHFN
```

---

Repeat element Consensuses:

```
ARM:       L+NLS*+***N+*--ALL**GGL-PALV+LL*S-*+E**L*-*AA*A
           A
                   II   I   I           I
                   VV   V   V           V
NPI-1
 &SRP1:    LSNI*SG***QPQ--*VVI*AGV*PPLV-LL*S-*-*E*K+E-ACWA
           I           V  A
```

FIG.3B

```
                     20                    40                    60
GGAGGCACCG AAGGGCAGCG CCGAGTCGGA GGGGGCGAAG ATTGACGCCA GTAAGAACGA
                     80                   100                   120
GGAGGATGAA GGCCATTCAA ACTCCTCCCC ACGACACTCT GAAGCAGCGA CGGCACAGCG
                    140                   160
GGAAGAATGG AAAATGTTTA TAGGAGGCCT TAGCTGGGAC ACTACAAAGA
```

FIG. 7

```
                    20                          40                          60
GAGGTCAATG  TGGAGCTGAG  GAAAGCTAAG  AAGGATGACC  AGATGCTGAA  GAGGAGAAAT
 E  V  N     V  E  L  R   K  A  K    K  D  D    Q  M  L  K   R  R  N>
                    80                         100                         120
GTAAGCTCAT  TTCCTGATGA  TGCTACTTCT  CCGCTGCAGG  AAAACCGCAA  CAACCAGGGC
 V  S  S    F  P  D  D   A  T  S    P  L  Q     E  N  R  N   N  Q  G>
                   140                         160                         180
ACTGTAAATT  GGTCTGTTGA  TGACATTGTC  AAAGGCATAA  ATAGCAGCAA  TGTGGAAAAT
 T  V  N    W  S  V  D   D  I  V    K  G  I     N  S  S  N   V  E  N>
                   200                         220                         240
CAGCTCCAAG  CTACTCAAGC  TGCCAGGAAA  CTACTTTCCA  GAGAAAAACA  GCCCCCCATA
 Q  L  Q    A  T  C  A   A  R  K    L  L  S     R  E  K  Q   P  P  I>
                   260                         280                         300
GACAACATAA  TCCGGGCTGG  TTTGATTCCG  AAATTTGTGT  CCTTCTTGGG  CAGAACTGAT
 D  N  I    I  R  A  G   L  I  P    K  F  V     S  F  L  G   R  T  D>
                   320                         340                         360
TGTAGTCCCA  TTCAGTTTGA  ATCTGCTTGG  GCACTACTA   ACATTGCTTC  TGGGACATCA
 C  S  P    I  Q  F  E   S  A  W    A  L  T     N  I  A  S   G  T  S>
                   380                         400                         420
GAACAAACCA  AGGCTGTGGT  AGATGGAGGT  GCCATCCCAG  CATTCATTTC  TCTGTTGGCA
 E  Q  T    K  A  V  V   D  G  G    A  I  P     A  F  I  S   L  L  A>
                   440                         460                         480
TCTCCCCATG  CTCACATCAG  TGAACAAGCT  GTCTGGGCTC  TAGGAAACAT  TGCAGGTGAT
 S  P  H    A  H  I  S   E  Q  A    V  W  A     L  G  N  I   A  G  D>
                   500                         520                         540
GGCTCAGTGT  TCCGAGACTT  GGTTATTAAG  TACGGTGCAG  TTGACCCACT  GTTGGCTCTC
 G  S  V    F  R  D  L   V  I  K    Y  G  A     V  D  P  L   L  A  L>
                   560                         580                         600
CTTGCAGTTC  CTGATATGTC  ATCTTTAGCA  TGTGGCTACT  TACGTAATCT  TACCTGGACA
 L  A  V    P  D  M  S   S  L  A    C  G  Y     L  R  N  L   T  W  T>
                   620                         640                         660
CTTTCTAATC  TTTGCCGCAA  CAAGAATCCT  GCACCCCCGA  TAGATGCTGT  TGAGCAGATT
 L  S  N    L  C  R  N   K  N  P    A  P  P     I  D  A  V   E  Q  I>
                   680                         700                         720
CTTCCTACCT  TAGTTCGGCT  CCTGCATCAT  GATGATCCAG  AAGTGTTAGC  AGATACCTGC
 L  P  T    L  V  R  L   L  H  H    D  D  P     E  V  L  A   D  T  C>
                   740                         760                         780
TGGGCTATTT  CCTACCTTAC  TGATGGTCCA  AATGAACGAA  TTGGCATGGT  GGTGAAAACA
 W  A  I    S  Y  L  T   D  G  P    N  E  R     I  G  M  V   V  K  T>
```

FIG.8A

```
                800                      820                      840
GGAGTTGTGC CCCAACTTGT GAAGCTTCTA GGAGCTTCTG AATTGCCAAT TGTGACTCCT
 G  V  V    P  Q  L  V  K  L  L   G  A  S   E  L  P  I  V  T  P>

860                      880                      900
GCCCTAAGAG CCATAGGGAA TATTGTCACT GGTACAGATG AACAGACTCA GGTTGTGATT
 A  L  R    A  I  G  N  I  V  T   G  T  D   E  Q  T  Q  V  V  I>

920                      940                      960
GATGCAGGAG CACTCGCCGT CTTTCCCAGC CTGCTCACCA ACCCCAAAAC TAACATTCAG
 D  A  G    A  L  A  V  F  P  S   L  L  T   N  P  K  T  N  I  Q>

980                     1000                     1020
AAGGAAGCTA CGTGGACAAT GTCAAACATC ACAGCCGGCC GCCAGGACCA GATACAGCAA
 K  E  A    T  W  T  M  S  W  I   T  A  G   R  Q  D  Q  I  Q  Q>

1040                     1060                     1080
GTTGTGAATC ATGGATTAGT CCCATTCCTT GTCAGTGTTC TCTCTAAGGC AGATTTTAAG
 V  V  N    H  G  L  V  P  F  L   V  S  V   L  S  K  A  D  F  K>

1100                     1120                     1140
ACACAAAAGG AAGCTGTGTG GGCCGTGACC AACTATACCA GTGGTGGAAC AGTTGAACAG
 T  Q  K    E  A  V  W  A  V  T   N  Y  T   S  G  G  T  V  E  Q>

1160                     1180                     1200
ATTGTGTACC TTGTTCACTG TGGCATAATA GAACCGTTGA TGAACCTCCT AACTGCAAAA
 I  V  Y    L  V  H  C  G  I  I   E  P  L   M  N  L  L  T  A  K>

1220                     1240                     1260
GATACCAAGA TTATTCTGGT TATCCTGGAT GCCATTTCAA ATATCTTTCA GGCTGCTGAG
 D  T  K    I  I  L  V  I  L  D   A  I  S   N  I  F  Q  A  A  E>

1280                     1300                     1320
AAACTAGGTG AAACTAGCTG CCCGTCTTCA CAGATTCAAG AACAAGGGAA AAGACAGTAC
 K  L  G    E  T  S  C  P  S  S   Q  I  Q   E  Q  G  K  R  Q  Y>
```

FIG.8B

```
                1340                    1360                    1380
AGAAATGAGG  CGTCCGAGGC  GTCGCAGAAT  AGAGAAACTT  AGTATAATGA  TTGAAGAATG
  R   N  E    A  S  E   A  S   Q    N   R  E   T>

1400                    1420                    1440
TGGAGGCTTA  GACAAAATTG  AAGCTCTACA  AAACCATGAA  AATGAGTCTG  TGTATAAGGC 1460                    1480                    1500
TTCGTTAAGC  TTAATTGAGA  AGTATTTCTC  TGTAGAGGAA  GAGGAAGATC  AAAACGTTGT 1520                    1540                    1560
ACCAGAAACT  ACCTCTGAAG  GCTACACTTT  CCAAGTTCAG  GATGGGGCTC  CTGGGACCTT 1580                    1600                    1620
TAACTTTTAG  ATCATGTAGC  TGAGACATAA  ATTTGTTGTG  TACTACGTTT  GGTATTTTGT 1640                    1660                    1680
CTTATTGTTT  CTCTACTAAG  AACTCTTTCT  TAAATGTGGT  TTGTTACTGT  AGCACTTTTT 1700                    1720                    1740
ACACTGAAAC  TATACTTGAA  CAGTTCCAAC  TGTACATACA  TACTGTATGA  AGCTTGTCCT 1760                    1780                    1800
CTGACTAGGT  TTCTAATTTC  TATGTGGAAT  TTCCTATCTT  GCAGCATCCT  GTAAATAAAC

1820
ATTCAAGTCC  ACCCTTTTCT  TGACTTC
```

FIG.8C

```
                    20              40              60
GAACGACCAA GAGGGTGTTC GACTGCTAGA GCCGAGCAGA AGCGTGCCTA AATCAAAGGA 80             100             120
ACTTGTTTCT TCAAGCTCTT CTGGCAGTGA TTCTGACAGT GAGGTTGACA AAAAGTTAAG 140             160             180
CAGGAAAAAG CAAGTTGCTC CAGAAAAACC TGTAAAGAAA CAAAAGACAG GTGAGACTTC 200             220             240
GAGAGCCCTG TCATCTTCTA AACAGAGCAG CAGCAGCAGA GATGATAACA TGTTTCAGAT

TGGGAAAATG AGGTCAGTT
```

FIG.9

```
                    20                          40                          60
        TGTCGACTGT  GGCTTTGAGC  ATCCGTCAGA  AGTCCAGCAT  GAGTGCATCC  CTCAGGCCAT 80                         100                         120
        TCTGGGAATG  GATGTCCTGT  GCCAGGCCAA  GTCGGGCATG  GGAAAGACAG  CAGTGTTTGT 140                         160                         180
        CTTGGCCACA  CTGCAACAGC  TGGAGCCAGT  TACTGGGCAG  GTGTCTGTAC  TGGTGATGTG 200                         220
        TCACACTCGG  GAGTTGGCTT  TTCAGATCAG  CAAGGAATAT  G
```

FIG. 10

```
                    20                          40                          60
        ATTTGTAAAC  CCCGGAGCGA  GGTTCTGCTT  ACCCGAGGCC  GCTGCTGTGC  GGAGACCCCC 80                         100                         120
        GGGTGAAGCC  ACCGTCATCA  TGTCTGACCA  GGAGGCAAAA  CCTTCAACTG  AGGACTTGGG 140                         160                         180
        GGATAAGAAG  GAAGGTGAAT  ATATTAAACT  CAAAGTCATT  GGACAGGATA  GCAGTGAGAT 200                         220                         240
        TCACTTCAAA  GTGAAAATGA  CAACACATCT  CAAGAAACTC  AAAGAATCAT  ACTGTCAAAG 260                         280                         300
        ACAGGGTGTT  CCAATGAATT  CACTCAGGTT  TCTCTTTGAG  GGTCAGAGAA  TTGCTGATAA 320                         340                         360
        TCATACTCCA  AAAGAACTGG  AATGGAGGA   AGAAGTTGTG  ATTGAAGTTT  ATCAGGAACA

AACGGGGGGT  CA
```

FIG. 11

-103                                                TCTGACCCTCGTCCCGCCCCGC          -80

-81 CATTCGCGCCTCCTCCTGTCCCGCAGTCGGGCGTCCAGCGGCTCTGCTGTTCGTGTGTCGTTGCAGGCCTTATTC       -1

1 ATGGGCTCACCGCTCGAGGTTCGACGGGCGGGGTACTGGTCACCGGCGGATTGGGCCGAGCCTATGCCCT             80
    M  G  S  P  L  R  F  D  G  R  V  V  L  V  T  G  A  G  A  G  L  G  R  A  Y  A  L    27

81 GGCTTTTGCAGAAAGAGAGGAGCGTTAGTTGTTGTGAATGATTTGGGAGGGCACTTCAAAGGAGTTGGTAAAGGCTCCTTAG  160
    A  F  A  E  R  G  A  L  V  V  V  N  D  L  G  G  D  F  K  G  V  G  K  G  S  L

161 CTGATAAAGGTTGTTGAAGAATAAGAAGGAGAGGTGGAAAAGCAGTGGCCAACTATGATTCAGTGGAAGAAGGAGAAGAAG   240
    A  D  K  V  V  E  E  I  R  R  R  G  G  K  A  V  A  N  Y  D  S  V  E  E  G  E  K    80

241 GTTGTGAAGACAGCCCTGGATGCTTTTGGAAGAATAGATGTTGGTCAACAATGCTGGAATTCTGAGGATCATTCCTT       320
    V  V  K  T  A  L  D  A  F  G  R  I  D  V  V  V  N  N  A  G  I  L  R  D  H  S  F    107

321 TGCTAGGATAAGTGATGAAGACTGGGATATAATCCACAGAGTTCATTTGCGGGGTTCATTCCAAGTGACACTGGCAGCAT    400
    A  R  I  S  D  E  D  W  D  I  I  H  R  V  H  L  R  G  S  F  Q  V  T  R  A  A       133

401 GGGAACACATGAAGAAACAGAAGAAACAGAAGTATGGAAGGATTATTATGACTTCATCAGCTTCAGGAATATATGCAACTTTGGCCAG  480
    W  E  H  M  K  K  Q  K  Y  G  R  I  I  M  T  S  S  A  S  G  I  Y  G  N  F  G  Q    160

481 GCCAATTATAGTGCTGCAAAGTTGGGTCTTCTCTGGGCTTGCAAATTCTTGCAATGAAGGCAGGAAAAGCAACATTCA     560
    A  N  Y  S  A  A  K  L  G  L  L  G  L  A  N  S  L  A  I  E  G  R  K  S  N  I  H    187

561 TTGTAACCATTGCTCCTAATGCGGGATCACGGATGACTCAGACAGTTATGCCTGAAGATCTTGTGGAAGCCTTGAAGC    640
    C  N  T  I  R  P  N  A  G  S  R  M  T  Q  T  V  M  P  E  D  L  V  E  A  L  K       213

FIG.12A

```
641 CAGAGTATGTGGCACCTCTTGTCCTTGGCTTTGTCACGAGAGTTGTGAGGAGAATGGTGGCTTGTTGAGGTTGGTGCA  720
     P  E  Y  V  A  P  L  V  L  W  L  C  H  E  S  C  E  E  N  G  G  L  F  E  V  G  A   240

721 GGATGGATTGGAAAATTACGCTGGGAGCGGACTCTTGGAGCTATTGTAAGACAAAAGAATCACCCAATGACTCCTGAGGC  800
     G  W  I  G  K  L  R  W  E  R  T  L  G  A  I  V  R  Q  K  N  H  P  M  T  P  E  A   267

801 AGTCAAGGCTAACTGGAAGAAGATCTGTGACTTTGAGAATGCCAGCAAGCCTCAGAGTATCCAAGAATCAACTGGCAGTA  880
     V  K  A  N  W  K  K  I  C  D  F  E  N  A  S  K  P  Q  S  I  Q  E  S  T  G  S     293

881 TAATTGAAGTTCTGAGTAAAATAGATTCAGAAGGAGGAGTTTCAGCAAATCATACTAGTCGTGCAACGTCTACAGCAACA  960
     I  I  E  V  L  S  K  I  D  S  E  G  G  V  S  A  N  H  T  S  R  A  T  S  T  A  T   320

961 TCAGGATTTGCTGGAGCTATTGGCCAGAAACTCCCTCCATTTCTATGCTTATACGAACTGGAAGCTATTATGTATGC  1040
     S  G  F  A  G  A  I  G  Q  K  L  P  P  F  S  Y  A  Y  T  E  L  E  A  I  M  Y  A   347

1041 CCTTGGAGTGGGAGCGTCAATCAAGGATCCAAAAGATTTGAAATTTATTTATGAAGGAAGTTCTGATTTCTCCTGTTGC  1120
      L  G  V  G  A  S  I  K  D  P  K  D  L  K  F  I  Y  E  G  S  S  D  F  S  C  L     373

1121 CCACCTTCGGAGTTATCATAGGTCAGAAATCTATGATGGGTGGAAGCAGAAAATTCCTGGACTTTCAATCAACTTT  1200
      P  T  F  G  V  I  I  G  Q  K  S  M  M  G  G  G  L  A  E  I  P  G  L  S  I  N  F   400

1201 GCAAAGGTTCTTCATGGAGAGCAGTATTTAGAGTTATATAAACCACTTCCCAGAGCAGGAAAATTAAAATGTGAAGCAGT  1280
      A  K  V  L  H  G  E  Q  Y  L  E  L  Y  K  P  L  P  R  A  G  K  L  K  C  E  A  V   427

1281 TGTTGCTGATGTCCTAGATAAAGGATCCGGTGTAGTGATTATTATGGATGTGTATTCTTATTCTGAAGAGAACTTATAT  1360
      V  A  D  V  L  D  K  G  S  G  V  V  I  I  M  D  V  Y  S  Y  S  E  K  E  L  I     453

1361 GCCACACAATCAGTTCTCTCTCTTTTGGCCTCTGGAGGCTTTGGTGGAAAACGGACATCAGACAAAGTCAAGGTAGCT  1440
      C  H  N  Q  F  S  L  F  L  V  G  S  G  G  F  G  G  K  R  T  S  D  K  V  K  V  A   480
```

FIG 12B

```
1441 GTAGCCATACCTAATAGACCTCCTGATGCTGTACTTACAGATACCACCTCTCTTAATCAGGTGCTTTGTACCGCCTCAG 1520
      V  A  I  P  N  R  P  P  D  A  V  L  T  D  T  T  S  L  N  Q  A  A  L  Y  R  L  S    507

1521 TGGAGACCGGAATCCCTTACACATTGATCCTAACTTGCTAGTCTAGCAGGTTTGACAAGCCCATATTACATGGATTAT 1600
      G  D  R  N  P  L  H  I  D  P  N  F  A  S  L  A  G  F  D  K  P  I  L  H  G  L    533

1601 GTACATTTGGATTTTCTGCCAGGCGTGTGTTACAGCAGTTTGCAGATAATGATGTGTCAAGATTCAAGGCAGTTAAGGCT 1680
      C  T  F  G  F  S  A  R  R  V  L  Q  Q  F  A  D  N  D  V  S  R  F  K  A  V  K  A    560

1681 CGTTTGCAAAACCAGTATATCCAGGACAAACTCTACAAACTGAGATGTGGAAGGAAGGAAACAGAATTCATTTCAAAC 1760
      R  F  A  K  P  V  Y  P  G  Q  T  L  Q  T  E  M  W  K  E  G  N  R  I  H  F  Q  T    587

1761 CAAGGTCCAAGAAACTGGACACATTGTCATTTCAAATGCATATGTGGATCTTGCACCAACATCTGGTACTTCAGCTAAGA 1840
      K  V  Q  E  T  G  D  I  V  I  S  N  A  Y  V  D  L  A  P  T  S  G  T  S  A  E    613

1841 CACCCCTCTGAGGGCGGGAAGCTTCAGAGTACCTTTGTATTTGAGGAAATAGGACGCCGCCTAAAGGATATTGGGCCTGAG 1920
      T  P  S  E  G  G  K  L  Q  S  T  F  V  F  E  E  I  G  R  R  R  L  K  D  I  G  P  E    640

1921 GTGGTGAAGAAAGTAAATGCTGTATTTGAGTGGCATATAACCAAAGGGCGGAAATATTGGGGCTAAGTGGACTATTGACCT 2000
      V  V  K  K  V  N  A  V  F  E  W  H  I  T  K  G  G  N  I  G  A  K  W  T  I  D  L    667
```

FIG. 12C

```
2001 GAAAAGTGGTCTGGAAAAGTGTACCAAGGCCCTGCAAAAGGTGTCTGATACAACAATCATACTTTCAGATGAAGATT 2080
      K  S  G  S  G  K  V  Y  Q  G  P  A  K  G  A  A  D  T  T  I  I  L  S  D  E  D     693

2081 TCATGGAGGTGGTCCTGGGCAAGCTTGACCCTCAGAAGGCATTCTTTAGTGGCAGGCGATTGAAGGCTGAAGGCCAGAGGAACATCATG 2160
      F  M  E  V  V  L  G  K  L  D  P  Q  K  A  F  F  S  G  R  L  K  A  R  G  N  I  M     720

2161 CTGAGCCAGAAACTTCAGATGATTCTTAAAGACTACGCCAAGCTCTGAAGGGCACACTACACTATTAATAAAAATGAAT 2240
      L  S  Q  K  L  Q  H  I  L  K  D  Y  A  K  L                                       735

2241 CATTAAATACTCTCTTCACCCAAATATGCTTGATTATTCTGCAAAGTGATTAGAACTAAGATGCAGGGGAAATTGCTTA 2320

2321 ACATTTCAGATATCAGATAACTGCAGATTTTCATTTCTACTAATTTTCATGTATCATTATTTTACAAGGAACTATA 2400

2401 TATAAGCTAGCACATAATTATCCTTCTGTTCTTAGATCTGTATCTTCATAATAAAAAATTTGCCCAAGTCCTGTTTCC 2480

2481 TTAGAATTTGTGATAGCATTGATAAGTTGAAAGGAAAATTAAATCAATAAAGGCCTTTGATACCTTTAAAAAAAAAAAA 2560
     AAAAAAAAAA
```

FIG.12D

```
-537 AGTGTCTCCCGGTTCGCGCGTCGGAGGTCGGTGCTCAGAGCTGCTCGGGCAGTTTCT  -481
-480 CCGCCTGCTGCTTCGGCGCGGGCTGTATCGGGGAGGGAGCGAGTTCCCGCGAGTTCTCGGTGGCGCTCCCCTTCCTTCA  -401
-400 GTCTCCACGGACTGGCCCCTCGTCCTTCTACTTGACCGCTCCCGTCTTCTGCCGCTTCTGGCGCTTCGTTGGGCCGA  -321
-320 TTCCGGCCCGCTTCCTCCTGCTTCCCCATGGAAGCTCTAGAAATGAATGTTCCATCTCTTCAGAGATGAACCAGATTATG  -241
-240 ATGCATCATTATCACAGAGAAATTCGTGTCTATAGCTTTTAAGGACTTGATTACATCATTTTCAAGCCTGATAGTTTTG  -161
-160 GAATCACCATTAGAGCTTAAGAGACACACCTGCCTTCATTTCAACCACCTGTCTTCATACCCTGACGAAGTGCACCTTTAA  -81
-80  CACTCCTTTGTCCTTGGATTACTTAAGAGTTCCCAGAAATACATTTGCCACCAACAGAGTAGCCAAATTTATAAGGAAAA  -1
1    ATGATTCCCAATGGATATTTGATGTTGAGGATGAAAATTTTATTGAGTCTTCTGTTGCCAAATTAAATGCCCTGAGGAA  80
     M   I   P   N   G   Y   L   M   F   E   D   E   N   F   I   E   S   S   V   A   K   L   N   A   L   R   K   27
81   AAGTGGCCAGTTCTGTGATGTTCGACTTCAGGTCTGTGGCCATGAAATGTTAGCACACAGAGCAGTGCTAGCTTGCTGCA  160
     S   G   Q   F   C   D   V   R   L   Q   V   C   G   H   E   M   L   A   H   R   A   V   L   A   C   C   53
161  GTCCCTATTTATTGAAATCTTTAATAGTGATAGTGATCCTCAGTTGAAATTCGACGATCTCAATCCA  240
     S   P   Y   L   F   E   I   F   N   S   D   S   D   P   H   G   I   S   H   V   K   F   D   D   L   N   P   80
241  GAAGCTGTTGAAGTCTTGTTGAATATGCTCAGTTGAAAGCAGATAAGGAATTGGTAAAAGATGTTATTC  320
     E   A   V   E   V   L   L   N   Y   A   Y   T   A   Q   L   K   A   D   K   E   L   V   K   D   V   V   Y   S   107
321  TGCAGCAAAAGAGCTGAAGATCGAGTAAAGCAGGTTTGTGGTGATTATTACTGTCTAGAATGGATGTTACCAGCT  400
     A   A   K   E   L   K   M   D   R   V   K   Q   V   C   G   D   Y   L   L   S   R   M   D   V   T   S   133
```

FIG. 16A

```
401  GCATCTCTTACCGAAATTTTGCAAGTTGTATGGGAGACTCCATTTGTTGAATAAGGTTGATGCTTATATTCAGGAGCAT   480
      C   I   S   Y   R   N   F   A   S   C   M   G   D   S   H   L   L   N   K   V   D   A   Y   I   Q   E   H     160

481  TTGTTACAAATTTCTGAAGAGGAGGAGTTTCTTAAGCTTCCAAGGCTAAAGTTGGAGGTAATGCTTGAAGATAATGTTTG   560
      L   L   Q   I   S   E   E   E   E   F   L   K   L   P   R   L   K   L   E   V   M   L   E   D   N   V   C     187

561  CTTGCCCAGCAATGGCAAATTATATACAAAGGTAATCAACTGGGTGCAGCGTAGCATCTGGGAGAATGGAGACAGTCTGG   640
      L   P   S   N   G   K   L   Y   T   K   V   I   N   W   V   Q   R   S   I   W   E   N   G   D   S   L       213

641  AAGAGCTGATGGAAGAGGTTCAAACCTTGTACTACTCAGCTGATCACAAGCTGCTTGATGGAAACCTACTAGATGGACAG   720
      E   E   L   M   E   E   V   Q   T   L   Y   Y   S   A   D   H   K   L   L   D   G   N   L   L   D   G   Q     240

721  GCTGAGGTGTTTGGCAGTGATGATGACCATTCAGTTTGTGCAGAAAAAGCCACCGTGAGAATGGCCATAAGCAGAT       800
      A   E   V   F   G   S   D   D   D   H   U   Q   F   V   Q   K   K   P   P   R   E   N   G   H   K   Q   I     267

801  AAGTAGCAGTTCAACTGGATGTCTCTTCTCCAAATGCTACAGTCCAAAGCCCTAAGCATGAGTGGAAAATCGTTGCTT     880
      S   S   S   S   T   G   C   L   S   S   P   N   A   T   V   Q   S   P   K   H   E   W   K   I   V   A       293

881  CAGAAAAGACTTCAAATAACACTTACTTGTGCCTGGCTGTGCTGGATGGTATATTCTGTGTCATTTTCTTCATGGGAGA   960
      S   E   K   T   S   N   N   T   Y   L   C   L   A   V   L   D   G   I   F   C   V   I   F   L   H   G   R     320

961  AACAGCCCACAGAGCTCACCAACAAGTACTCCAAAAACTAAGTAAGAGTTTAAGCTTTGAGATGCAACAAGATGAGCTAAT   1040
      N   S   P   Q   S   S   P   T   S   T   P   K   L   S   K   S   L   S   F   E   M   Q   Q   D   E   L   I     347

1041 CGAAAAGCCCATGTCTCCTATGCAGTACGCAGCACGATCTGGTCTGGGAACAGCAGAGATGAATGGCAAACTCATAGCTGCAG   1120
      E   K   P   M   S   P   M   Q   Y   A   R   S   G   L   G   T   A   E   M   N   G   K   L   I   A   A       373

1121 GTGGCTATAACAGAGAGGAATGTCTTCGAACAGTCGAATGCTATAATCCACATACAGATCACTGGTCCTTTCTTGCTCCC   1200
      G   G   Y   N   R   E   E   C   L   R   T   V   E   C   Y   N   P   H   T   D   H   W   S   F   L   A   P     400
```

FIG. 16B

```
1201  ATGAGAACACCAAGAGCCCGATTTCAAATGGCTGTACTCATGGGCCAGCTCTATGTGGTAGGTGGATCAAATGGCCACTC  1280
       M  R  T  P  R  A  R  F  Q  M  A  V  L  M  G  Q  L  Y  V  V  G  G  S  N  G  H  S   427
1281  AGATGACCTGAGTTGTGTGGAGAGATGTATGATTCAAACATAGATGACTGGATTCCTGTTCCAGAATTGAGAACTAACCGTT 1360
       D  D  L  S  C  G  E  M  Y  D  S  N  I  D  D  W  I  P  V  P  E  L  R  T  N  R      453
1361  GTAATGCAGGAGTGTGTGCTCTGAATGGAAAGTTATACATCGTTGGTGGCTCTGATCCATATGGTCAAAAAGGACTGAAA  1440
       C  N  A  G  V  C  A  L  N  G  K  L  Y  I  V  G  G  S  D  P  Y  G  Q  K  G  L  K   480
1441  AATTGTGATGTATTTGATCCTGTAACAAAGTTGTGGACAAGCTGTGCCCCTCTTAACATTCGGAGACACCAGTCTGCAGT  1520
       N  C  D  V  F  D  P  V  T  K  L  W  T  S  C  A  P  L  N  I  R  R  H  Q  S  A  V   507
1521  CTGTGAGCTTGGTGGTTATTTGTACATAATCGGAGGTGCAGAGAATCTTGGAATTGTCTGAACACAGTAGAACGATACAATC 1600
       C  E  L  G  G  Y  L  Y  I  I  G  G  A  E  S  W  N  C  L  N  T  V  E  R  Y  N      533
1601  CTGAAAATAATACCTGGACTTTAATTGCACCCATGAATGTGGCTCTCATGGAGGAGCTGGAGTGGCTGTGTTCTTAATGGAAAAA 1680
       P  E  N  N  T  W  T  L  I  A  P  M  N  V  A  R  R  G  A  G  V  A  V  L  N  G  K   560
1681  CTGTTTGTATGTGGCTTTGATGGTTCTCATGCCATCAGTTGTGTGGAAATGTATGATCCAACTAGAAATGAATGGAA  1780
       L  F  V  C  G  G  F  D  G  S  H  A  I  S  C  V  E  M  Y  D  P  T  R  N  E  W  K   587
1761  GATGATGGGACATATGACTTCACCAAGGAGCAATGCTGGGATTGCAACTGTAGGGAACACCATTTATGCAGTGGAGGATT  1840
       M  M  G  H  M  T  S  P  R  S  N  A  G  I  A  T  V  G  N  T  I  Y  A  V  E  D      613
1841  CGATGGCAATGAATTTCTGAATACGGCGGAAGTCTATAACCTTGAGTCAAATGAATGGAGCCCCTATACAAAGATTTTCC  1920
       S  M  A  M  N  F  *
1921  AGTTTTAACGGGTTTAAGACCCTCTCAAACTAACAGGCTTAGTGATGTAATTATGGTTAGCAGAGAGGTACACTTGTGAATA  2000
2001  AAGAGGGTGGGTGGGGATAGATGTTGCTAACAGCAACACAAGCTTTGCATATTGCATATTAAACATGCTGTACAT  2080
2081  ACTTTTTGGGTTTATTTGGGAAGGAATGCAAAGATGAAGGTCTGTTGTGTACTTTTAAGACTTTGGTTATTTACTTTT  2160
2161  TGGAAAAGATAAACCAAGAATTGATTGGGCACATCAAAAAAAAAAAAAAAAA
```

FIG. 16C

```
              1                                                            49
Repeat 1   KliaaGGyn.  .rEeCLrtVE  cYnPhTdhWs  FLAPMrtpRa  rfqmAvLmG   415
Repeat 2   qLYVVGGsnG  hsD.dLScgE  MYDsnidDWi  pvpeLrtnRc  nAGVcaLNG   463
Repeat 3   KLYIVGGsDp  ygqkgLkncD  vFDPvTklWt  scAPLnirRh  qsaVceLgG   512
Repeat 4   yLYIIGGaEs  .wn.ClntVE  rYnPenntWt  LiAPMnvaRr  gAGVAvLNG   559
Repeat 5   KLFVcGGfDG  .sh.aiScVE  MYPDtrnEWk  MMghMtspRS  nAGIAtvgn   606

Consens.   KLY--GG---  -----L--VE  -YPD----W-  --APM---R-  -AGVA-L-G-
```

FIG. 18

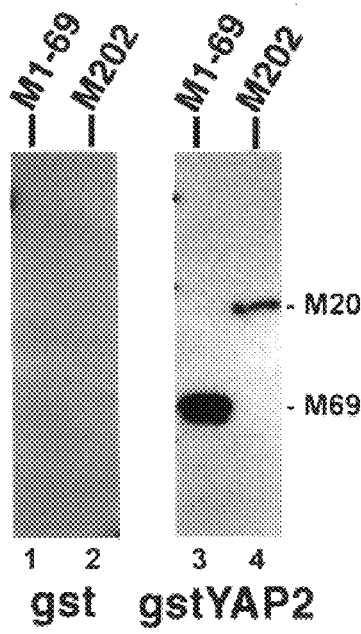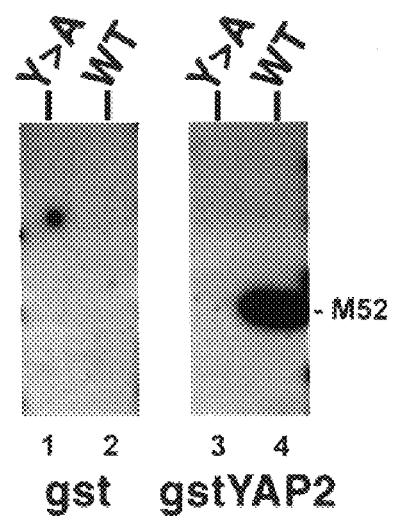
FIG.29A  FIG.29B  FIG.29C

```
                              SEQUENCE LISTING

<160> NUMBER OF SEQ ID NOS: 42

<210> SEQ ID NO 1
<211> LENGTH: 27
<212> TYPE: DNA
<213> ORGANISM: Artificial Sequence
<220> FEATURE:
<223> OTHER INFORMATION: pLexA-NP bait plasmid

<400> SEQUENCE: 1
gactggctgg aattccccat ggcgtcc                                            27

<210> SEQ ID NO 2
<211> LENGTH: 9
<212> TYPE: PRT
<213> ORGANISM: Artificial Sequence
<220> FEATURE:
<223> OTHER INFORMATION: pLexA-NP bait plasmid

<400> SEQUENCE: 2

Asp Trp Leu Glu Phe Pro Met Ala Ser
  1               5

<210> SEQ ID NO 3
<211> LENGTH: 2940
<212> TYPE: DNA
<213> ORGANISM: Homo sapiens
<220> FEATURE:
<221> NAME/KEY: CDS
<222> LOCATION: (47)...(1660)

<400> SEQUENCE: 3
ctaacttcag cggtggcacc gggatcggtt gccttgagcc tgaaat atg acc acc          55
                                                  Met Thr Thr
                                                    1 cca gga aaa gag aac ttt cgc ctg aaa agt tac aag aac aaa tct ctg        103
Pro Gly Lys Glu Asn Phe Arg Leu Lys Ser Tyr Lys Asn Lys Ser Leu
      5                  10                  15 aat ccc gat gag atg cgc agg agg agg gag gaa gga ctg cag tta            151
Asn Pro Asp Glu Met Arg Arg Arg Arg Glu Glu Glu Gly Leu Gln Leu
 20                  25                  30                  35 cga aag cag aaa aga gaa gag cag tta ttc aag cgg aga aat gtt gct        199
Arg Lys Gln Lys Arg Glu Glu Gln Leu Phe Lys Arg Arg Asn Val Ala
                  40                  45                  50 aca gca gaa gaa gaa aca gaa gaa gaa gtt atg tca gat gga ggc ttt        247
Thr Ala Glu Glu Glu Thr Glu Glu Glu Val Met Ser Asp Gly Gly Phe
              55                  60                  65 cat gag gct cag att agt aac atg gag atg gca cca ggt ggt gtc atc        295
His Glu Ala Gln Ile Ser Asn Met Glu Met Ala Pro Gly Gly Val Ile
          70                  75                  80 act tct gac atg att gag atg ata ttt tcc aaa agc cca gag caa cag        343
Thr Ser Asp Met Ile Glu Met Ile Phe Ser Lys Ser Pro Glu Gln Gln
      85                  90                  95 ctt tca gca aca cag aaa ttc agg aag ctg ctt tca aaa gaa cct aac        391
Leu Ser Ala Thr Gln Lys Phe Arg Lys Leu Leu Ser Lys Glu Pro Asn
100                 105                 110                 115 cct cct att gat gaa gtt atc agc aca cca gga gta gtg gcc agg ttt        439
```

```
Pro Pro Ile Asp Glu Val Ile Ser Thr Pro Gly Val Val Ala Arg Phe
        120                 125                 130 gtg gag ttc ctc aaa cga aaa gag aat tgt tca ctg cag ttt gaa tca       487
Val Glu Phe Leu Lys Arg Lys Glu Asn Cys Ser Leu Gln Phe Glu Ser
            135                 140                 145 gct tgg gta ctg aca aat att gct tca gga aat tct ctt cag acc cga       535
Ala Trp Val Leu Thr Asn Ile Ala Ser Gly Asn Ser Leu Gln Thr Arg
        150                 155                 160 att gtg att cag gca aga gct gtg ccc atc ttc ata gag ttg ctc agc       583
Ile Val Ile Gln Ala Arg Ala Val Pro Ile Phe Ile Glu Leu Leu Ser
165                 170                 175 tca gag ttt gaa gat gtc cag gaa cag gca gtc tgg gct ctt ggc aac       631
Ser Glu Phe Glu Asp Val Gln Glu Gln Ala Val Trp Ala Leu Gly Asn
180                 185                 190                 195 att gct gga gat agt acc atg tgc agg gac tat gtc tta gac tgc aat       679
Ile Ala Gly Asp Ser Thr Met Cys Arg Asp Tyr Val Leu Asp Cys Asn
            200                 205                 210 atc ctt ccc cct ctt ttg cag tta ttt tca aag caa aac cgc ctg acc       727
Ile Leu Pro Pro Leu Leu Gln Leu Phe Ser Lys Gln Asn Arg Leu Thr
        215                 220                 225 atg acc cgg aat gca gta tgg gct ttg tct aat ctc tgt aga ggg aaa       775
Met Thr Arg Asn Ala Val Trp Ala Leu Ser Asn Leu Cys Arg Gly Lys
        230                 235                 240 agt cca cct cca gaa ttt gca aag gtt tct cca tgt ctg aat gtg ctt       823
Ser Pro Pro Pro Glu Phe Ala Lys Val Ser Pro Cys Leu Asn Val Leu
        245                 250                 255 tcc tgg ttg ctg ttt gtc agt gac act gat gta ctg gct gat gcc tgc       871
Ser Trp Leu Leu Phe Val Ser Asp Thr Asp Val Leu Ala Asp Ala Cys
260                 265                 270                 275 tgg gcc ctc tca tat cta tca gat gga ccc aat gat aaa att caa gcg       919
Trp Ala Leu Ser Tyr Leu Ser Asp Gly Pro Asn Asp Lys Ile Gln Ala
            280                 285                 290 gtc atc gat gcg gga gta tgt agg aga ctt gtg gaa ctg ctg atg cat       967
Val Ile Asp Ala Gly Val Cys Arg Arg Leu Val Glu Leu Leu Met His
        295                 300                 305 aat gat tat aaa gtg gtt tct cct gct ttg cga gct gtg gga aac att      1015
Asn Asp Tyr Lys Val Val Ser Pro Ala Leu Arg Ala Val Gly Asn Ile
        310                 315                 320 gtc aca ggg gat gat att cag aca cag gta att ctg aat tgc tca gct      1063
Val Thr Gly Asp Asp Ile Gln Thr Gln Val Ile Leu Asn Cys Ser Ala
325                 330                 335 ctg cag agt tta ttg cat ttg ctg agt agc cca aag gaa tct atc aaa      1111
Leu Gln Ser Leu Leu His Leu Leu Ser Ser Pro Lys Glu Ser Ile Lys
340                 345                 350                 355 aag gaa gca tgt tgg acg ata tct aat att aca gct gga aat agg gca      1159
Lys Glu Ala Cys Trp Thr Ile Ser Asn Ile Thr Ala Gly Asn Arg Ala
            360                 365                 370 cag atc cag act gtg ata gat gcc aac att ttc cca gcc ctc att agt      1207
Gln Ile Gln Thr Val Ile Asp Ala Asn Ile Phe Pro Ala Leu Ile Ser
        375                 380                 385 att tta caa act gct gaa ttt cgg aca aga aaa gaa gca gct tgg gcc      1255
Ile Leu Gln Thr Ala Glu Phe Arg Thr Arg Lys Glu Ala Ala Trp Ala
        390                 395                 400 atc aca aat gca act tct gga gga tca gct gaa cag atc aag tac cta      1303
Ile Thr Asn Ala Thr Ser Gly Gly Ser Ala Glu Gln Ile Lys Tyr Leu
        405                 410                 415 gta gaa ctg ggt tgt atc aag ccg ctc tgt gat ctc ctc acg gtc atg      1351
Val Glu Leu Gly Cys Ile Lys Pro Leu Cys Asp Leu Leu Thr Val Met
420                 425                 430                 435
```

| | | |
|---|---|---|
| gac tct aag att gta cag gtt gcc cta aat ggc ttg gaa aat atc ctg | | 1399 |
| Asp Ser Lys Ile Val Gln Val Ala Leu Asn Gly Leu Glu Asn Ile Leu | | |
| 440 445 450 | | |
| agg ctt gga gaa cag gaa gcc aaa agg aac ggc act ggc att aac cct | | 1447 |
| Arg Leu Gly Glu Gln Glu Ala Lys Arg Asn Gly Thr Gly Ile Asn Pro | | |
| 455 460 465 | | |
| tac tgt gct ttg att gaa gaa gct tat ggt ctg gat aaa att gag ttc | | 1495 |
| Tyr Cys Ala Leu Ile Glu Glu Ala Tyr Gly Leu Asp Lys Ile Glu Phe | | |
| 470 475 480 | | |
| tta cag agt cat gaa aac cag gag atc tac caa aag gcc ttt gat ctt | | 1543 |
| Leu Gln Ser His Glu Asn Gln Glu Ile Tyr Gln Lys Ala Phe Asp Leu | | |
| 485 490 495 | | |
| att gag cat tac ttc ggg acc gaa gat gaa gac agc agc att gca ccc | | 1591 |
| Ile Glu His Tyr Phe Gly Thr Glu Asp Glu Asp Ser Ser Ile Ala Pro | | |
| 500 505 510 515 | | |
| cag gtt gac ctt aac cag cag cag tac atc ttc caa cag tgt gag gct | | 1639 |
| Gln Val Asp Leu Asn Gln Gln Gln Tyr Ile Phe Gln Gln Cys Glu Ala | | |
| 520 525 530 | | |
| cct atg gaa ggt ttc cag ctt tgaagcaata ctctgctttc acgtacctgt | | 1690 |
| Pro Met Glu Gly Phe Gln Leu | | |
| 535 | | |
| gctcagacca ggctacccag tcgagtcctc ttgtggagcc cacagtcctc atggagctaa | | 1750 |
| cttctcaaat gttttccata atactgtttg cgctcatttg cttgccttgc gcacctgctc | | 1810 |
| tcttacacac atctgaaaaa cctccggctc tctgtggtgg atacccttc taataaaagg | | 1870 |
| gtaaccagaa cggcccactc tcttttacgg aaaaatccct aggctttgga gatccgcact | | 1930 |
| tacattagag ttatgggaat atacacatat taatgtggct ccctttttct tgtgggggaa | | 1990 |
| taaaagagga ctcctcctca ttcccttttaa catgggggaa aaaactgaca ttaaaagatg | | 2050 |
| agactaaatc tttatcttga attttacaca actacttacg acaagggaga tgtttagacc | | 2110 |
| tgttggtata cttcagagta cttttcatga gttcttccac agtgaaccct tggattacct | | 2170 |
| ggtggctttt tctagccaga ttgcattaat ccttactgag attggatggt tttctttcct | | 2230 |
| ctattggcgc cattcttcag atattaaagt taaaccatcc actccctcac cttcagcctt | | 2290 |
| cagtgaatgt gctttctagt tgtcaggaat gctgaagaat taacactttg actcctaaat | | 2350 |
| gtgatactgg tgggtaagag cagggcacat ttaatttgtt cgcttttgct tctctttggt | | 2410 |
| ctgggcacat ttaatttgtt cgcttttgct tctctttggt cttttcgaat acttagtaat | | 2470 |
| cgaaaaccat atcctgtaat ttaataaaaa aaactaagga cgaaaaaacc cctccaattt | | 2530 |
| tcccaaatgc aatcagtgta actaggggct gtgtttctgc attaaaataa atgtttcagg | | 2590 |
| ctttgtggtc ctgatcaagg tcctcattaa aaaattggag ttcaccctag gcttttcccc | | 2650 |
| tctgtgactg gcagataaca catactttg aaagtaactt tgggattttt tttcttaggt | | 2710 |
| gcagctcgat tctaatcttt tcatgctgca cacgattcct ttaatcgata gcatccttat | | 2770 |
| ctgaaagaaa taaccatctt ctcaacatga cctgcttaac ccaaataaga acagtgatct | | 2830 |
| tataacctca ttgtttccta atctatttta tttcatctcc tgctagtact gtgccgcttc | | 2890 |
| cccctccccc cacacaaaat aaaaacagta tctcgcttct ggctcatttt | | 2940 |

<210> SEQ ID NO 4
<211> LENGTH: 538
<212> TYPE: PRT
<213> ORGANISM: Homo sapiens

<400> SEQUENCE: 4

Met Thr Thr Pro Gly Lys Glu Asn Phe Arg Leu Lys Ser Tyr Lys Asn

-continued

```
  1               5                  10                 15
Lys Ser Leu Asn Pro Asp Glu Met Arg Arg Arg Glu Glu Gly
                20              25              30
Leu Gln Leu Arg Lys Gln Arg Glu Glu Leu Phe Lys Arg Arg
            35              40              45
Asn Val Ala Thr Ala Glu Glu Thr Glu Glu Val Met Ser Asp
        50              55              60
Gly Phe His Glu Ala Gln Ile Ser Asn Met Glu Met Ala Pro Gly
65              70              75              80
Gly Val Ile Thr Ser Asp Met Ile Glu Met Ile Phe Ser Lys Ser Pro
                85              90              95
Glu Gln Gln Leu Ser Ala Thr Gln Lys Phe Arg Lys Leu Leu Ser Lys
                100             105             110
Glu Pro Asn Pro Pro Ile Asp Glu Val Ile Ser Thr Pro Gly Val Val
                115             120             125
Ala Arg Phe Val Glu Phe Leu Lys Arg Lys Glu Asn Cys Ser Leu Gln
        130             135             140
Phe Glu Ser Ala Trp Val Leu Thr Asn Ile Ala Ser Gly Asn Ser Leu
145             150             155             160
Gln Thr Arg Ile Val Ile Gln Ala Arg Ala Val Pro Ile Phe Ile Glu
                165             170             175
Leu Leu Ser Ser Glu Phe Glu Asp Val Gln Glu Gln Ala Val Trp Ala
                180             185             190
Leu Gly Asn Ile Ala Gly Asp Ser Thr Met Cys Arg Asp Tyr Val Leu
            195             200             205
Asp Cys Asn Ile Leu Pro Pro Leu Leu Gln Leu Phe Ser Lys Gln Asn
        210             215             220
Arg Leu Thr Met Thr Arg Asn Ala Val Trp Ala Leu Ser Asn Leu Cys
225             230             235             240
Arg Gly Lys Ser Pro Pro Pro Glu Phe Ala Lys Val Ser Pro Cys Leu
                245             250             255
Asn Val Leu Ser Trp Leu Leu Phe Val Ser Asp Thr Asp Val Leu Ala
                260             265             270
Asp Ala Cys Trp Ala Leu Ser Tyr Leu Ser Asp Gly Pro Asn Asp Lys
        275             280             285
Ile Gln Ala Val Ile Asp Ala Gly Val Cys Arg Arg Leu Val Glu Leu
        290             295             300
Leu Met His Asn Asp Tyr Lys Val Val Ser Pro Ala Leu Arg Ala Val
305             310             315             320
Gly Asn Ile Val Thr Gly Asp Asp Ile Gln Thr Gln Val Ile Leu Asn
                325             330             335
Cys Ser Ala Leu Gln Ser Leu Leu His Leu Leu Ser Ser Pro Lys Glu
            340             345             350
Ser Ile Lys Lys Glu Ala Cys Trp Thr Ile Ser Asn Ile Thr Ala Gly
        355             360             365
Asn Arg Ala Gln Ile Gln Thr Val Ile Asp Ala Asn Ile Phe Pro Ala
        370             375             380
Leu Ile Ser Ile Leu Gln Thr Ala Glu Phe Arg Thr Arg Lys Glu Ala
385             390             395             400
Ala Trp Ala Ile Thr Asn Ala Thr Ser Gly Gly Ser Ala Glu Gln Ile
                405             410             415
Lys Tyr Leu Val Glu Leu Gly Cys Ile Lys Pro Leu Cys Asp Leu Leu
            420             425             430
```

```
Thr Val Met Asp Ser Lys Ile Val Gln Val Ala Leu Asn Gly Leu Glu
        435                 440                 445
Asn Ile Leu Arg Leu Gly Glu Gln Glu Ala Lys Arg Asn Gly Thr Gly
    450                 455                 460
Ile Asn Pro Tyr Cys Ala Leu Ile Glu Glu Ala Tyr Gly Leu Asp Lys
465                 470                 475                 480
Ile Glu Phe Leu Gln Ser His Glu Asn Gln Glu Ile Tyr Gln Lys Ala
                485                 490                 495
Phe Asp Leu Ile Glu His Tyr Phe Gly Thr Glu Asp Glu Asp Ser Ser
            500                 505                 510
Ile Ala Pro Gln Val Asp Leu Asn Gln Gln Tyr Ile Phe Gln Gln
        515                 520                 525
Cys Glu Ala Pro Met Glu Gly Phe Gln Leu
    530                 535
```

<210> SEQ ID NO 5
<211> LENGTH: 542
<212> TYPE: PRT
<213> ORGANISM: Saccharomyces cerevisiae

<400> SEQUENCE: 5

```
Met Asp Asn Gly Thr Asp Ser Ser Thr Ser Lys Phe Val Pro Glu Tyr
1               5                   10                  15
Arg Arg Thr Asn Phe Lys Asn Lys Gly Arg Phe Ser Ala Asp Glu Leu
            20                  25                  30
Arg Arg Arg Arg Asp Thr Gln Gln Val Glu Leu Arg Lys Ala Lys Arg
        35                  40                  45
Asp Glu Ala Leu Ala Lys Arg Arg Asn Phe Ile Pro Pro Thr Asp Gly
    50                  55                  60
Ala Asp Ser Asp Glu Glu Asp Glu Ser Ser Val Ser Ala Asp Gln Gln
65                  70                  75                  80
Phe Tyr Ser Gln Leu Gln Gln Glu Leu Pro Gln Met Thr Gln Gln Leu
                85                  90                  95
Asn Ser Asp Asp Met Gln Glu Gln Leu Ser Ala Thr Val Lys Phe Arg
            100                 105                 110
Gln Ile Leu Ser Arg Glu His Arg Pro Pro Ile Asp Val Val Ile Gln
        115                 120                 125
Ala Gly Val Val Pro Arg Leu Val Glu Phe Met Arg Glu Asn Gln Pro
    130                 135                 140
Glu Met Leu Gln Leu Glu Ala Ala Trp Ala Leu Thr Asn Ile Ala Ser
145                 150                 155                 160
Gly Thr Ser Ala Gln Thr Lys Val Val Asp Ala Asp Ala Val Pro
                165                 170                 175
Leu Phe Ile Gln Leu Leu Tyr Thr Gly Ser Val Glu Val Lys Glu Gln
                180                 185                 190
Ala Ile Trp Ala Leu Gly Asn Val Ala Gly Asp Ser Thr Asp Tyr Arg
        195                 200                 205
Asp Tyr Val Leu Gln Cys Asn Ala Met Glu Pro Ile Leu Gly Leu Phe
    210                 215                 220
Asn Ser Asn Lys Pro Ser Leu Ile Arg Thr Ala Thr Trp Thr Leu Ser
225                 230                 235                 240
Asn Leu Cys Arg Gly Lys Lys Pro Gln Pro Asp Trp Ser Val Val Ser
                245                 250                 255
Gln Ala Leu Pro Thr Leu Ala Lys Leu Ile Tyr Ser Met Asp Thr Glu
```

```
                260                 265                 270
Thr Leu Val Asp Ala Cys Trp Ala Ile Ser Tyr Leu Ser Asp Gly Pro
            275                 280                 285

Gln Glu Ala Ile Gln Ala Val Ile Asp Val Arg Ile Pro Lys Arg Leu
            290                 295                 300

Val Glu Leu Leu Ser His Glu Ser Thr Leu Val Gln Thr Pro Ala Leu
305                 310                 315                 320

Arg Ala Val Gly Asn Ile Val Thr Gly Asn Asp Leu Gln Thr Gln Val
                325                 330                 335

Val Ile Asn Ala Gly Val Leu Pro Ala Leu Arg Leu Leu Ser Ser
                340                 345                 350

Pro Lys Glu Asn Ile Lys Lys Glu Ala Cys Trp Thr Ile Ser Asn Ile
            355                 360                 365

Thr Ala Gly Asn Thr Glu Gln Ile Gln Ala Val Ile Asp Ala Asn Leu
            370                 375                 380

Ile Pro Pro Leu Val Lys Leu Leu Glu Val Ala Glu Tyr Lys Thr Lys
385                 390                 395                 400

Lys Glu Ala Cys Trp Ala Ile Ser Asn Ala Ser Ser Gly Gly Leu Gln
                405                 410                 415

Arg Pro Asp Ile Ile Arg Tyr Leu Val Ser Gln Gly Cys Ile Lys Pro
            420                 425                 430

Leu Cys Asp Leu Leu Glu Ile Ala Asp Asn Arg Ile Ile Glu Val Thr
            435                 440                 445

Leu Asp Ala Leu Glu Asn Ile Leu Lys Met Gly Glu Ala Asp Lys Glu
            450                 455                 460

Ala Arg Gly Leu Asn Ile Asn Glu Asn Ala Asp Phe Ile Glu Lys Ala
465                 470                 475                 480

Gly Gly Met Glu Lys Ile Phe Asn Cys Gln Gln Asn Glu Asn Asp Lys
                485                 490                 495

Ile Tyr Glu Lys Ala Tyr Lys Ile Ile Glu Thr Tyr Phe Gly Glu Glu
            500                 505                 510

Glu Asp Ala Val Asp Glu Thr Met Ala Pro Gln Asn Ala Gly Asn Thr
            515                 520                 525

Phe Gly Phe Gly Ser Asn Val Asn Gln Gln Phe Asn Phe Asn
            530                 535                 540

<210> SEQ ID NO 6
<211> LENGTH: 170
<212> TYPE: DNA
<213> ORGANISM: Saccharomyces cerevisiae

<400> SEQUENCE: 6
ggaggcaccg aagggcagcg ccgagtcgga gggggcgaag attgacgcca gtaagaacga      60
ggaggatgaa ggccattcaa actcctcccc acgacactct gaagcagcga cggcacagcg     120
ggaagaatgg aaaatgttta taggaggcct tagctgggac actacaaaga                170

<210> SEQ ID NO 7
<211> LENGTH: 1827
<212> TYPE: DNA
<213> ORGANISM: Homo sapiens
<220> FEATURE:
<221> NAME/KEY: CDS
<222> LOCATION: (1)...(1359)

<400> SEQUENCE: 7 gag gtc aat gtg gag ctg agg aaa gct aag aag gat gac cag atg ctg      48
```

```
Glu Val Asn Val Glu Leu Arg Lys Ala Lys Lys Asp Asp Gln Met Leu
 1               5                  10                  15 aag agg aga aat gta agc tca ttt cct gat gat gct act tct ccg ctg       96
Lys Arg Arg Asn Val Ser Ser Phe Pro Asp Asp Ala Thr Ser Pro Leu
             20                  25                  30 cag gaa aac cgc aac aac cag ggc act gta aat tgg tct gtt gat gac      144
Gln Glu Asn Arg Asn Asn Gln Gly Thr Val Asn Trp Ser Val Asp Asp
         35                  40                  45 att gtc aaa ggc ata aat agc agc aat gtg gaa aat cag ctc caa gct      192
Ile Val Lys Gly Ile Asn Ser Ser Asn Val Glu Asn Gln Leu Gln Ala
    50                  55                  60 act caa gct gcc agg aaa cta ctt tcc aga gaa aaa cag ccc ccc ata      240
Thr Gln Ala Ala Arg Lys Leu Leu Ser Arg Glu Lys Gln Pro Pro Ile
 65                  70                  75                  80 gac aac ata atc cgg gct ggt ttg att ccg aaa ttt gtg tcc ttc ttg      288
Asp Asn Ile Ile Arg Ala Gly Leu Ile Pro Lys Phe Val Ser Phe Leu
                 85                  90                  95 ggc aga act gat tgt agt ccc att cag ttt gaa tct gct tgg gca ctc      336
Gly Arg Thr Asp Cys Ser Pro Ile Gln Phe Glu Ser Ala Trp Ala Leu
            100                 105                 110 act aac att gct tct ggg aca tca gaa caa acc aag gct gtg gta gat      384
Thr Asn Ile Ala Ser Gly Thr Ser Glu Gln Thr Lys Ala Val Val Asp
        115                 120                 125 gga ggt gcc atc cca gca ttc att tct ctg ttg gca tct ccc cat gct      432
Gly Gly Ala Ile Pro Ala Phe Ile Ser Leu Leu Ala Ser Pro His Ala
130                 135                 140 cac atc agt gaa caa gct gtc tgg gct cta gga aac att gca ggt gat      480
His Ile Ser Glu Gln Ala Val Trp Ala Leu Gly Asn Ile Ala Gly Asp
145                 150                 155                 160 ggc tca gtg ttc cga gac ttg gtt att aag tac ggt gca gtt gac cca      528
Gly Ser Val Phe Arg Asp Leu Val Ile Lys Tyr Gly Ala Val Asp Pro
                165                 170                 175 ctg ttg gct ctc ctt gca gtt cct gat atg tca tct tta gca tgt ggc      576
Leu Leu Ala Leu Leu Ala Val Pro Asp Met Ser Ser Leu Ala Cys Gly
            180                 185                 190 tac tta cgt aat ctt acc tgg aca ctt tct aat ctt tgc cgc aac aag      624
Tyr Leu Arg Asn Leu Thr Trp Thr Leu Ser Asn Leu Cys Arg Asn Lys
        195                 200                 205 aat cct gca ccc ccg ata gat gct gtt gag cag att ctt cct acc tta      672
Asn Pro Ala Pro Pro Ile Asp Ala Val Glu Gln Ile Leu Pro Thr Leu
210                 215                 220 gtt cgg ctc ctg cat cat gat gat cca gaa gtg tta gca gat acc tgc      720
Val Arg Leu Leu His His Asp Asp Pro Glu Val Leu Ala Asp Thr Cys
225                 230                 235                 240 tgg gct att tcc tac ctt act gat ggt cca aat gaa cga att ggc atg      768
Trp Ala Ile Ser Tyr Leu Thr Asp Gly Pro Asn Glu Arg Ile Gly Met
                245                 250                 255 gtg gtg aaa aca gga gtt gtg ccc caa ctt gtg aag ctt cta gga gct      816
Val Val Lys Thr Gly Val Val Pro Gln Leu Val Lys Leu Leu Gly Ala
            260                 265                 270 tct gaa ttg cca att gtg act cct gcc cta aga gcc ata ggg aat att      864
Ser Glu Leu Pro Ile Val Thr Pro Ala Leu Arg Ala Ile Gly Asn Ile
        275                 280                 285 gtc act ggt aca gat gaa cag act cag gtt gtg att gat gca gga gca      912
Val Thr Gly Thr Asp Glu Gln Thr Gln Val Val Ile Asp Ala Gly Ala
290                 295                 300 ctc gcc gtc ttt ccc agc ctg ctc acc aac ccc aaa act aac att cag      960
Leu Ala Val Phe Pro Ser Leu Leu Thr Asn Pro Lys Thr Asn Ile Gln
305                 310                 315                 320
```

-continued

```
aag gaa gct acg tgg aca atg tca aac atc aca gcc ggc cgc cag gac      1008
Lys Glu Ala Thr Trp Thr Met Ser Asn Ile Thr Ala Gly Arg Gln Asp
                325                 330                 335 cag ata cag caa gtt gtg aat cat gga tta gtc cca ttc ctt gtc agt      1056
Gln Ile Gln Gln Val Val Asn His Gly Leu Val Pro Phe Leu Val Ser
    340                 345                 350 gtt ctc tct aag gca gat ttt aag aca caa aag gaa gct gtg tgg gcc      1104
Val Leu Ser Lys Ala Asp Phe Lys Thr Gln Lys Glu Ala Val Trp Ala
355                 360                 365 gtg acc aac tat acc agt ggt gga aca gtt gaa cag att gtg tac ctt      1152
Val Thr Asn Tyr Thr Ser Gly Gly Thr Val Glu Gln Ile Val Tyr Leu
        370                 375                 380 gtt cac tgt ggc ata ata gaa ccg ttg atg aac ctc tta act gca aaa      1200
Val His Cys Gly Ile Ile Glu Pro Leu Met Asn Leu Leu Thr Ala Lys
385                 390                 395                 400 gat acc aag att att ctg gtt atc ctg gat gcc att tca aat atc ttt      1248
Asp Thr Lys Ile Ile Leu Val Ile Leu Asp Ala Ile Ser Asn Ile Phe
                405                 410                 415 cag gct gct gag aaa cta ggt gaa act agc tgc ccg tct tca cag att      1296
Gln Ala Ala Glu Lys Leu Gly Glu Thr Ser Cys Pro Ser Ser Gln Ile
    420                 425                 430 caa gaa caa ggg aaa aga cag tac aga aat gag gcg tcc gag gcg tcg      1344
Gln Glu Gln Gly Lys Arg Gln Tyr Arg Asn Glu Ala Ser Glu Ala Ser
435                 440                 445 cag aat aga gaa act tagtataatg attgaagaat gtggaggctt agacaaaatt      1399
Gln Asn Arg Glu Thr
    450 gaagctctac aaaaccatga aaatgagtct gtgtataagg cttcgttaag cttaattgag    1459 aagtatttct ctgtagagga agaggaagat caaaacgttg taccagaaac tacctctgaa    1519 ggctacactt tccaagttca ggatggggct cctgggacct ttaactttta gatcatgtag    1579 ctgagacata aatttgttgt gtactacgtt tggtattttg tcttattgtt tctctactaa    1639 gaactctttc ttaaatgtgg tttgttactg tagcactttt tacactgaaa ctatacttga    1699 acagttccaa ctgtacatac atactgtatg aagcttgtcc tctgactagg tttctaattt    1759 ctatgtggaa tttcctatct tgcagcatcc tgtaaataaa cattcaagtc cacccttttc    1819 ttgacttc                                                             1827
```

<210> SEQ ID NO 8
<211> LENGTH: 453
<212> TYPE: PRT
<213> ORGANISM: Homo sapiens

<400> SEQUENCE: 8

```
Glu Val Asn Val Glu Leu Arg Lys Ala Lys Lys Asp Asp Gln Met Leu
1               5                   10                  15

Lys Arg Arg Asn Val Ser Ser Phe Pro Asp Asp Ala Thr Ser Pro Leu
                20                  25                  30

Gln Glu Asn Arg Asn Asn Gln Gly Thr Val Asn Trp Ser Val Asp Asp
            35                  40                  45

Ile Val Lys Gly Ile Asn Ser Ser Asn Val Glu Asn Gln Leu Gln Ala
        50                  55                  60

Thr Gln Ala Ala Arg Lys Leu Leu Ser Arg Glu Lys Gln Pro Pro Ile
65                  70                  75                  80

Asp Asn Ile Ile Arg Ala Gly Leu Ile Pro Lys Phe Val Ser Phe Leu
                85                  90                  95

Gly Arg Thr Asp Cys Ser Pro Ile Gln Phe Glu Ser Ala Trp Ala Leu
```

```
                    100                 105                 110
Thr Asn Ile Ala Ser Gly Thr Ser Glu Gln Thr Lys Ala Val Val Asp
            115                 120                 125
Gly Gly Ala Ile Pro Ala Phe Ile Ser Leu Leu Ala Ser Pro His Ala
        130                 135                 140
His Ile Ser Glu Gln Ala Val Trp Ala Leu Gly Asn Ile Ala Gly Asp
145                 150                 155                 160
Gly Ser Val Phe Arg Asp Leu Val Ile Lys Tyr Gly Ala Val Asp Pro
                165                 170                 175
Leu Leu Ala Leu Leu Ala Val Pro Asp Met Ser Ser Leu Ala Cys Gly
            180                 185                 190
Tyr Leu Arg Asn Leu Thr Trp Thr Leu Ser Asn Leu Cys Arg Asn Lys
        195                 200                 205
Asn Pro Ala Pro Pro Ile Asp Ala Val Glu Gln Ile Leu Pro Thr Leu
    210                 215                 220
Val Arg Leu Leu His His Asp Asp Pro Glu Val Leu Ala Asp Thr Cys
225                 230                 235                 240
Trp Ala Ile Ser Tyr Leu Thr Asp Gly Pro Asn Glu Arg Ile Gly Met
                245                 250                 255
Val Val Lys Thr Gly Val Val Pro Gln Leu Val Lys Leu Leu Gly Ala
            260                 265                 270
Ser Glu Leu Pro Ile Val Thr Pro Ala Leu Arg Ala Ile Gly Asn Ile
        275                 280                 285
Val Thr Gly Thr Asp Glu Gln Thr Gln Val Val Ile Asp Ala Gly Ala
    290                 295                 300
Leu Ala Val Phe Pro Ser Leu Leu Thr Asn Pro Lys Thr Asn Ile Gln
305                 310                 315                 320
Lys Glu Ala Thr Trp Thr Met Ser Asn Ile Thr Ala Gly Arg Gln Asp
                325                 330                 335
Gln Ile Gln Gln Val Val Asn His Gly Leu Val Pro Phe Leu Val Ser
            340                 345                 350
Val Leu Ser Lys Ala Asp Phe Lys Thr Gln Lys Glu Ala Val Trp Ala
        355                 360                 365
Val Thr Asn Tyr Thr Ser Gly Gly Thr Val Glu Gln Ile Val Tyr Leu
    370                 375                 380
Val His Cys Gly Ile Ile Glu Pro Leu Met Asn Leu Leu Thr Ala Lys
385                 390                 395                 400
Asp Thr Lys Ile Ile Leu Val Ile Leu Asp Ala Ile Ser Asn Ile Phe
                405                 410                 415
Gln Ala Ala Glu Lys Leu Gly Glu Thr Ser Cys Pro Ser Ser Gln Ile
            420                 425                 430
Gln Glu Gln Gly Lys Arg Gln Tyr Arg Asn Glu Ala Ser Glu Ala Ser
        435                 440                 445
Gln Asn Arg Glu Thr
    450

<210> SEQ ID NO 9
<211> LENGTH: 259
<212> TYPE: DNA
<213> ORGANISM: Homo sapiens

<400> SEQUENCE: 9
gaacgaccaa gagggtgttc gactgctaga gccgagcaga agcgtgccta aatcaaagga      60
acttgtttct tcaagctctt ctggcagtga ttctgacagt gaggttgaca aaaagttaag     120
```

```
caggaaaaag caagttgctc cagaaaaacc tgtaaagaaa caaagacag gtgagacttc      180 gagagccctg tcatcttcta aacagagcag cagcagcaga gatgataaca tgtttcagat      240
tgggaaaatg aggtcagtt                                                   259

<210> SEQ ID NO 10
<211> LENGTH: 221
<212> TYPE: DNA
<213> ORGANISM: Homo sapiens

<400> SEQUENCE: 10
tgtcgactgt ggctttgagc atccgtcaga agtccagcat gagtgcatcc ctcaggccat       60
tctgggaatg gatgtcctgt gccaggccaa gtcgggcatg ggaaagacag cagtgtttgt      120
cttggccaca ctgcaacagc tggagccagt tactgggcag gtgtctgtac tggtgatgtg      180
tcacactcgg gagttggctt ttcagatcag caaggaatat g                         221

<210> SEQ ID NO 11
<211> LENGTH: 372
<212> TYPE: DNA
<213> ORGANISM: Homo sapiens

<400> SEQUENCE: 11
atttgtaaac cccggagcga ggttctgctt acccgaggcc gctgctgtgc ggagaccccc       60
gggtgaagcc accgtcatca tgtctgacca ggaggcaaaa ccttcaactg aggacttggg      120
ggataagaag gaaggtgaat atattaaact caaagtcatt ggacaggata gcagtgagat      180
tcacttcaaa gtgaaaatga caacacatct caagaaactc aaagaatcat actgtcaaag      240
acagggtgtt ccaatgaatt cactcaggtt tctctttgag ggtcagagaa ttgctgataa      300
tcatactcca aaagaactgg gaatggagga agaagttgtg attgaagttt atcaggaaca      360 aacgggggt ca                                                          372

<210> SEQ ID NO 12
<211> LENGTH: 2675
<212> TYPE: DNA
<213> ORGANISM: Homo sapiens
<220> FEATURE:
<221> NAME/KEY: CDS
<222> LOCATION: (104)...(2310)

<400> SEQUENCE: 12
tctgaccctc gtcccgcccc cgccattcgc cgcctcctcc tgtcccgcag tcggcgtcca       60
gcggctctgc ttgttcgtgt gtgtgtcgtt gcaggcctta ttc atg ggc tca ccg       115
                                                Met Gly Ser Pro
                                                  1 ctg agg ttc gac ggg cgg gtg gta ctg gtc acc ggc gcg ggg gca gga       163
Leu Arg Phe Asp Gly Arg Val Val Leu Val Thr Gly Ala Gly Ala Gly
  5                  10                  15                  20 ttg ggc cga gcc tat gcc ctg gct ttt gca gaa aga gga gcg tta gtt       211
Leu Gly Arg Ala Tyr Ala Leu Ala Phe Ala Glu Arg Gly Ala Leu Val
              25                  30                  35 gtt gtg aat gat ttg gga ggg cac ttc aaa gga gtt ggt aaa ggc tcc       259
Val Val Asn Asp Leu Gly Gly His Phe Lys Gly Val Gly Lys Gly Ser
          40                  45                  50 tta gct gat aag gtt gtt gaa gaa ata aga agg aga ggt gga aaa gca       307
Leu Ala Asp Lys Val Val Glu Glu Ile Arg Arg Arg Gly Gly Lys Ala
      55                  60                  65 gtg gcc aac tat gat tca gtg gaa gaa gga gag aag gtt gtg aag aca       355
```

-continued

```
Val Ala Asn Tyr Asp Ser Val Glu Glu Gly Lys Val Val Lys Thr
         70              75                  80 gcc ctg gat gct ttt gga aga ata gat gtt gtg gtc aac aat gct gga      403
Ala Leu Asp Ala Phe Gly Arg Ile Asp Val Val Val Asn Asn Ala Gly
 85              90                  95                 100 att ctg agg gat cat tcc ttt gct agg ata agt gat gaa gac tgg gat      451
Ile Leu Arg Asp His Ser Phe Ala Arg Ile Ser Asp Glu Asp Trp Asp
                105                 110                 115 ata atc cac aga gtt cat ttg cgg ggt tca ttc caa gtg aca cgg gca      499
Ile Ile His Arg Val His Leu Arg Gly Ser Phe Gln Val Thr Arg Ala
            120                 125                 130 gca tgg gaa cac atg aag aaa cag aag tat gga agg att att atg act      547
Ala Trp Glu His Met Lys Lys Gln Lys Tyr Gly Arg Ile Ile Met Thr
        135                 140                 145 tca tca gct tca gga ata tat ggc aac ttt ggc cag gcc aat tat agt      595
Ser Ser Ala Ser Gly Ile Tyr Gly Asn Phe Gly Gln Ala Asn Tyr Ser
150                 155                 160 gct gca aag ttg ggt ctt ctg ggc ctt gca aat tct ctt gca att gaa      643
Ala Ala Lys Leu Gly Leu Leu Gly Leu Ala Asn Ser Leu Ala Ile Glu
165                 170                 175                 180 ggc agg aaa agc aac att cat tgt aac acc att gct cct aat gcg gga      691
Gly Arg Lys Ser Asn Ile His Cys Asn Thr Ile Ala Pro Asn Ala Gly
                185                 190                 195 tca cgg atg act cag aca gtt atg cct gaa gat ctt gtg gaa gcc ttg      739
Ser Arg Met Thr Gln Thr Val Met Pro Glu Asp Leu Val Glu Ala Leu
            200                 205                 210 aag cca gag tat gtg gca cct ctt gtc ctt tgg ctt tgt cac gag agt      787
Lys Pro Glu Tyr Val Ala Pro Leu Val Leu Trp Leu Cys His Glu Ser
        215                 220                 225 tgt gag gag aat ggt ggc ttg ttt gag gtt ggt gca gga tgg att gga      835
Cys Glu Glu Asn Gly Gly Leu Phe Glu Val Gly Ala Gly Trp Ile Gly
230                 235                 240 aaa tta cgc tgg gag cgg act ctt gga gct att gta aga caa aag aat      883
Lys Leu Arg Trp Glu Arg Thr Leu Gly Ala Ile Val Arg Gln Lys Asn
245                 250                 255                 260 cac cca atg act cct gag gca gtc aag gct aac tgg aag aag atc tgt      931
His Pro Met Thr Pro Glu Ala Val Lys Ala Asn Trp Lys Lys Ile Cys
                265                 270                 275 gac ttt gag aat gcc agc aag cct cag agt atc caa gaa tca act ggc      979
Asp Phe Glu Asn Ala Ser Lys Pro Gln Ser Ile Gln Glu Ser Thr Gly
            280                 285                 290 agt ata att gaa gtt ctg agt aaa ata gat tca gaa gga gga gtt tca     1027
Ser Ile Ile Glu Val Leu Ser Lys Ile Asp Ser Glu Gly Gly Val Ser
        295                 300                 305 gca aat cat act agt cgt gca acg tct aca gca aca tca gga ttt gct     1075
Ala Asn His Thr Ser Arg Ala Thr Ser Thr Ala Thr Ser Gly Phe Ala
310                 315                 320 gga gct att ggc cag aaa ctc cct cca ttt tct tat gct tat acg gaa     1123
Gly Ala Ile Gly Gln Lys Leu Pro Pro Phe Ser Tyr Ala Tyr Thr Glu
325                 330                 335                 340 ctg gaa gct att atg tat gcc ctt gga gtg gga gcg tca atc aag gat     1171
Leu Glu Ala Ile Met Tyr Ala Leu Gly Val Gly Ala Ser Ile Lys Asp
                345                 350                 355 cca aaa gat ttg aaa ttt att tat gaa gga agt tct gat ttc tcc tgt     1219
Pro Lys Asp Leu Lys Phe Ile Tyr Glu Gly Ser Ser Asp Phe Ser Cys
            360                 365                 370 ttg ccc acc ttc gga gtt atc ata ggt cag aaa tct atg atg ggt gga     1267
Leu Pro Thr Phe Gly Val Ile Ile Gly Gln Lys Ser Met Met Gly Gly
        375                 380                 385
```

```
gga tta gca gaa att cct gga ctt tca atc aac ttt gca aag gtt ctt        1315
Gly Leu Ala Glu Ile Pro Gly Leu Ser Ile Asn Phe Ala Lys Val Leu
        390                 395                 400 cat gga gag cag tac tta gag tta tat aaa cca ctt ccc aga gca gga        1363
His Gly Glu Gln Tyr Leu Glu Leu Tyr Lys Pro Leu Pro Arg Ala Gly
405                 410                 415                 420 aaa tta aaa tgt gaa gca gtt gtt gct gat gtc cta gat aaa gga tcc        1411
Lys Leu Lys Cys Glu Ala Val Val Ala Asp Val Leu Asp Lys Gly Ser
                425                 430                 435 ggt gta gtg att att atg gat gtc tat tct tat tct gag aag gaa ctt        1459
Gly Val Val Ile Ile Met Asp Val Tyr Ser Tyr Ser Glu Lys Glu Leu
            440                 445                 450 ata tgc cac aat cag ttc tct ctc ttt ctt gtt ggc tct gga ggc ttt        1507
Ile Cys His Asn Gln Phe Ser Leu Phe Leu Val Gly Ser Gly Gly Phe
            455                 460                 465 ggt gga aaa cgg aca tca gac aaa gtc aag gta gct gta gcc ata cct        1555
Gly Gly Lys Arg Thr Ser Asp Lys Val Lys Val Ala Val Ala Ile Pro
        470                 475                 480 aat aga cct cct gat gct gta ctt aca gat acc acc tct ctt aat cag        1603
Asn Arg Pro Pro Asp Ala Val Leu Thr Asp Thr Thr Ser Leu Asn Gln
485                 490                 495                 500 gct gct ttg tac cgc ctc agt gga gac cgg aat ccc tta cac att gat        1651
Ala Ala Leu Tyr Arg Leu Ser Gly Asp Arg Asn Pro Leu His Ile Asp
                505                 510                 515 cct aac ttt gct agt cta gca ggt ttt gac aag ccc ata tta cat gga        1699
Pro Asn Phe Ala Ser Leu Ala Gly Phe Asp Lys Pro Ile Leu His Gly
            520                 525                 530 tta tgt aca ttt gga ttt tct gcc agg cgt gtg tta cag cag ttt gca        1747
Leu Cys Thr Phe Gly Phe Ser Ala Arg Arg Val Leu Gln Gln Phe Ala
            535                 540                 545 gat aat gat gtg tca aga ttc aag gca gtt aag gct cgt ttt gca aaa        1795
Asp Asn Asp Val Ser Arg Phe Lys Ala Val Lys Ala Arg Phe Ala Lys
550                 555                 560 cca gta tat cca gga caa act cta caa act gag atg tgg aag gaa gga        1843
Pro Val Tyr Pro Gly Gln Thr Leu Gln Thr Glu Met Trp Lys Glu Gly
565                 570                 575                 580 aac aga att cat ttt caa acc aag gtc caa gaa act gga gac att gtc        1891
Asn Arg Ile His Phe Gln Thr Lys Val Gln Glu Thr Gly Asp Ile Val
                585                 590                 595 att tca aat gca tat gtg gat ctt gca cca aca tct ggt act tca gct        1939
Ile Ser Asn Ala Tyr Val Asp Leu Ala Pro Thr Ser Gly Thr Ser Ala
            600                 605                 610 aag aca ccc tct gag ggc ggg aag ctt cag agt acc ttt gta ttt gag        1987
Lys Thr Pro Ser Glu Gly Gly Lys Leu Gln Ser Thr Phe Val Phe Glu
            615                 620                 625 gaa ata gga cgc cgc cta aag gat att ggg cct gag gtg gtg aag aaa        2035
Glu Ile Gly Arg Arg Leu Lys Asp Ile Gly Pro Glu Val Val Lys Lys
        630                 635                 640 gta aat gct gta ttt gag tgg cat ata acc aaa ggc gga aat att ggg        2083
Val Asn Ala Val Phe Glu Trp His Ile Thr Lys Gly Gly Asn Ile Gly
645                 650                 655                 660 gct aag tgg act att gac ctg aaa agt ggt tct gga aaa gtg tac caa        2131
Ala Lys Trp Thr Ile Asp Leu Lys Ser Gly Ser Gly Lys Val Tyr Gln
                665                 670                 675 ggc cct gca aaa ggt gct gct gat aca aca atc ata ctt tca gat gaa        2179
Gly Pro Ala Lys Gly Ala Ala Asp Thr Thr Ile Ile Leu Ser Asp Glu
            680                 685                 690 gat ttc atg gag gtg gtc ctg ggc aag ctt gac cct cag aag gca ttc        2227
Asp Phe Met Glu Val Val Leu Gly Lys Leu Asp Pro Gln Lys Ala Phe
            695                 700                 705
```

```
ttt agt ggc agg ctg aag gcc aga ggg aac atc atg ctg agc cag aaa    2275
Phe Ser Gly Arg Leu Lys Ala Arg Gly Asn Ile Met Leu Ser Gln Lys
        710                 715                 720 ctt cag atg att ctt aaa gac tac gcc aag ctc tg aagggcacac           2320
Leu Gln Met Ile Leu Lys Asp Tyr Ala Lys Leu
725                 730                 735 tacactatta ataaaaatgg aatcattaaa tactctcttc acccaaatat gcttgattat   2380
tctgcaaaag tgattagaac taagatgcag gggaaattgc ttaacatttt cagatatcag   2440
ataactgcag attttcattt tctactaatt tttcatgtat cattattttt acaaggaact   2500
atatataagc tagcacataa ttatccttct gttcttagat ctgtatcttc ataataaaaa   2560
aattttgccc aagtcctgtt tccttagaat ttgtgatagc attgataagt tgaaaggaaa   2620
attaaatcaa taaggcctt tgatacctt aaaaaaaaaa aaaaaaaaa aaaaa           2675
```

<210> SEQ ID NO 13
<211> LENGTH: 735
<212> TYPE: PRT
<213> ORGANISM: Homo sapiens

<400> SEQUENCE: 13

```
Met Gly Ser Pro Leu Arg Phe Asp Gly Arg Val Val Leu Val Thr Gly
1               5                   10                  15

Ala Gly Ala Gly Leu Gly Arg Ala Tyr Ala Leu Ala Phe Ala Glu Arg
                20                  25                  30

Gly Ala Leu Val Val Asn Asp Leu Gly Gly His Phe Lys Gly Val
            35                  40                  45

Gly Lys Gly Ser Leu Ala Asp Lys Val Val Glu Glu Ile Arg Arg Arg
    50                  55                  60

Gly Gly Lys Ala Val Ala Asn Tyr Asp Ser Val Glu Glu Gly Glu Lys
65                  70                  75                  80

Val Val Lys Thr Ala Leu Asp Ala Phe Gly Arg Ile Asp Val Val
                85                  90                  95

Asn Asn Ala Gly Ile Leu Arg Asp His Ser Phe Ala Arg Ile Ser Asp
                100                 105                 110

Glu Asp Trp Asp Ile Ile His Arg Val His Leu Arg Gly Ser Phe Gln
            115                 120                 125

Val Thr Arg Ala Ala Trp Glu His Met Lys Lys Gln Lys Tyr Gly Arg
    130                 135                 140

Ile Ile Met Thr Ser Ser Ala Ser Gly Ile Tyr Gly Asn Phe Gly Gln
145                 150                 155                 160

Ala Asn Tyr Ser Ala Ala Lys Leu Gly Leu Leu Gly Leu Ala Asn Ser
                165                 170                 175

Leu Ala Ile Glu Gly Arg Lys Ser Asn Ile His Cys Asn Thr Ile Ala
            180                 185                 190

Pro Asn Ala Gly Ser Arg Met Thr Gln Thr Val Met Pro Glu Asp Leu
    195                 200                 205

Val Glu Ala Leu Lys Pro Glu Tyr Val Ala Pro Leu Val Leu Trp Leu
    210                 215                 220

Cys His Glu Ser Cys Glu Glu Asn Gly Gly Leu Phe Glu Val Gly Ala
225                 230                 235                 240

Gly Trp Ile Gly Lys Leu Arg Trp Glu Arg Thr Leu Gly Ala Ile Val
                245                 250                 255

Arg Gln Lys Asn His Pro Met Thr Pro Glu Ala Val Lys Ala Asn Trp
            260                 265                 270
```

-continued

```
Lys Lys Ile Cys Asp Phe Glu Asn Ala Ser Lys Pro Gln Ser Ile Gln
            275                 280                 285

Glu Ser Thr Gly Ser Ile Ile Glu Val Leu Ser Lys Ile Asp Ser Glu
        290                 295                 300

Gly Gly Val Ser Ala Asn His Thr Ser Arg Ala Thr Ser Thr Ala Thr
305                 310                 315                 320

Ser Gly Phe Ala Gly Ala Ile Gly Gln Lys Leu Pro Pro Phe Ser Tyr
                325                 330                 335

Ala Tyr Thr Glu Leu Glu Ala Ile Met Tyr Ala Leu Gly Val Gly Ala
            340                 345                 350

Ser Ile Lys Asp Pro Lys Asp Leu Lys Phe Ile Tyr Glu Gly Ser Ser
            355                 360                 365

Asp Phe Ser Cys Leu Pro Thr Phe Gly Val Ile Ile Gly Gln Lys Ser
        370                 375                 380

Met Met Gly Gly Gly Leu Ala Glu Ile Pro Gly Leu Ser Ile Asn Phe
385                 390                 395                 400

Ala Lys Val Leu His Gly Glu Gln Tyr Leu Glu Leu Tyr Lys Pro Leu
                405                 410                 415

Pro Arg Ala Gly Lys Leu Lys Cys Glu Ala Val Val Ala Asp Val Leu
            420                 425                 430

Asp Lys Gly Ser Gly Val Val Ile Met Asp Val Tyr Ser Tyr Ser
            435                 440                 445

Glu Lys Glu Leu Ile Cys His Asn Gln Phe Ser Leu Phe Leu Val Gly
        450                 455                 460

Ser Gly Gly Phe Gly Gly Lys Arg Thr Ser Asp Lys Val Lys Val Ala
465                 470                 475                 480

Val Ala Ile Pro Asn Arg Pro Pro Asp Ala Val Leu Thr Asp Thr Thr
                485                 490                 495

Ser Leu Asn Gln Ala Ala Leu Tyr Arg Leu Ser Gly Asp Arg Asn Pro
            500                 505                 510

Leu His Ile Asp Pro Asn Phe Ala Ser Leu Ala Gly Phe Asp Lys Pro
        515                 520                 525

Ile Leu His Gly Leu Cys Thr Phe Gly Phe Ser Ala Arg Arg Val Leu
            530                 535                 540

Gln Gln Phe Ala Asp Asn Asp Val Ser Arg Phe Lys Ala Val Lys Ala
545                 550                 555                 560

Arg Phe Ala Lys Pro Val Tyr Pro Gly Gln Thr Leu Gln Thr Glu Met
                565                 570                 575

Trp Lys Glu Gly Asn Arg Ile His Phe Gln Thr Lys Val Gln Glu Thr
            580                 585                 590

Gly Asp Ile Val Ile Ser Asn Ala Tyr Val Asp Leu Ala Pro Thr Ser
        595                 600                 605

Gly Thr Ser Ala Lys Thr Pro Ser Glu Gly Gly Lys Leu Gln Ser Thr
            610                 615                 620

Phe Val Phe Glu Glu Ile Gly Arg Arg Leu Lys Asp Ile Gly Pro Glu
625                 630                 635                 640

Val Val Lys Lys Val Asn Ala Val Phe Glu Trp His Ile Thr Lys Gly
                645                 650                 655

Gly Asn Ile Gly Ala Lys Trp Thr Ile Asp Leu Lys Ser Gly Ser Gly
            660                 665                 670

Lys Val Tyr Gln Gly Pro Ala Lys Gly Ala Ala Asp Thr Thr Ile Ile
        675                 680                 685
```

```
Leu Ser Asp Glu Asp Phe Met Glu Val Val Leu Gly Lys Leu Asp Pro
    690                 695                 700

Gln Lys Ala Phe Phe Ser Gly Arg Leu Lys Ala Arg Gly Asn Ile Met
705                 710                 715                 720

Leu Ser Gln Lys Leu Gln Met Ile Leu Lys Asp Tyr Ala Lys Leu
                725                 730                 735

<210> SEQ ID NO 14
<211> LENGTH: 2752
<212> TYPE: DNA
<213> ORGANISM: Homo sapiens
<220> FEATURE:
<221> NAME/KEY: CDS
<222> LOCATION: (538)...(2394)

<400> SEQUENCE: 14
```

| | | |
|---|---|---|
| agtgtctccc ggtcgcgcgt ggaggtcggt cgctcagagc tgctgggcgc agtttctccg | 60 |
| cctgctgctt cggcgcggct gtatcggcga gcgagcgagt tcccgcgagt tctcggtggc | 120 |
| gctccccctt cctttcagtc tccacggact ggccctcgt ccttctactt gaccgctccc | 180 |
| gtcttctgcc gccttctggc gctttccgtt gggccgattc ccgcccgctt cctcctgctt | 240 |
| cccatcgaag ctctagaaat gaatgtttcc atctcttcag agatgaacca gattatgatg | 300 |
| catcattatc acagaagaaa ttcgtgtcta tagcttttaa ggacttgatt acatcatttt | 360 |
| caagcctgat agttttggaa tcaccattag agcttaagac acacctgcct tcatttcaac | 420 |
| cacctgtctt catacgctga cgaagtgcac cttttaaaac tccttttgtcc ttggattact | 480 |
| taagagttcc cagaaataca tttgccacca acagagtagc caaatttata aggaaaa atg | 540 |
| | | Met |
| | | 1 |

```
att ccc aat gga tat ttg atg ttt gag gat gaa aat ttt att gag tct    588
Ile Pro Asn Gly Tyr Leu Met Phe Glu Asp Glu Asn Phe Ile Glu Ser
        5                  10                  15 tct gtt gcc aaa tta aat gcc ctg agg aaa agt ggc cag ttc tgt gat    636
Ser Val Ala Lys Leu Asn Ala Leu Arg Lys Ser Gly Gln Phe Cys Asp
        20                  25                  30 gtt cga ctt cag gtc tgt ggc cat gaa atg tta gca cac aga gca gtg    684
Val Arg Leu Gln Val Cys Gly His Glu Met Leu Ala His Arg Ala Val
 35                  40                  45 cta gct tgc tgc agt ccc tat tta ttt gaa atc ttt aat agt gat agt    732
Leu Ala Cys Cys Ser Pro Tyr Leu Phe Glu Ile Phe Asn Ser Asp Ser
 50                  55                  60                  65 gat cct cat gga att tct cac gtt aaa ttt gat gat ctc aat cca gaa    780
Asp Pro His Gly Ile Ser His Val Lys Phe Asp Asp Leu Asn Pro Glu
                70                  75                  80 gct gtt gaa gtc ttg ttg aat tat gcc tac act gct cag ttg aaa gca    828
Ala Val Glu Val Leu Leu Asn Tyr Ala Tyr Thr Ala Gln Leu Lys Ala
            85                  90                  95 gat aag gaa ttg gta aaa gat gtt tat tct gca gca aaa gag ctg aag    876
Asp Lys Glu Leu Val Lys Asp Val Tyr Ser Ala Ala Lys Glu Leu Lys
        100                 105                 110 atg gat cga gta aag cag gtt tgt ggt gat tat tta ctg tct aga atg    924
Met Asp Arg Val Lys Gln Val Cys Gly Asp Tyr Leu Leu Ser Arg Met
    115                 120                 125 gat gtt acc agc tgc atc tct tac cga aat ttt gca agt tgt atg gga    972
Asp Val Thr Ser Cys Ile Ser Tyr Arg Asn Phe Ala Ser Cys Met Gly
130                 135                 140                 145 gac tcc cat ttg ttg aat aag gtt gat gct tat att cag gag cat ttg   1020
Asp Ser His Leu Leu Asn Lys Val Asp Ala Tyr Ile Gln Glu His Leu
                150                 155                 160
```

-continued

| | | |
|---|---|---|
| tta caa att tct gaa gag gag gag ttt ctt aag ctt cca agg cta aag<br>Leu Gln Ile Ser Glu Glu Glu Glu Phe Leu Lys Leu Pro Arg Leu Lys<br>165                    170                  175 | 1068 | |
| ttg gag gta atg ctt gaa gat aat gtt tgc ttg ccc agc aat ggc aaa<br>Leu Glu Val Met Leu Glu Asp Asn Val Cys Leu Pro Ser Asn Gly Lys<br>        180                  185                  190 | 1116 | |
| tta tat aca aag gta atc aac tgg gtg cag cgt agc atc tgg gag aat<br>Leu Tyr Thr Lys Val Ile Asn Trp Val Gln Arg Ser Ile Trp Glu Asn<br>195                    200                  205 | 1164 | |
| gga gac agt ctg gaa gag ctg atg gaa gag gtt caa acc ttg tac tac<br>Gly Asp Ser Leu Glu Glu Leu Met Glu Glu Val Gln Thr Leu Tyr Tyr<br>210                    215                  220                  225 | 1212 | |
| tca gct gat cac aag ctg ctt gat ggg aac cta cta gat gga cag gct<br>Ser Ala Asp His Lys Leu Leu Asp Gly Asn Leu Leu Asp Gly Gln Ala<br>        230                  235                  240 | 1260 | |
| gag gtg ttt ggc agt gat gat gac cac att cag ttt gtg cag aaa aag<br>Glu Val Phe Gly Ser Asp Asp Asp His Ile Gln Phe Val Gln Lys Lys<br>                 245                  250                  255 | 1308 | |
| cca cca cgt gag aat ggc cat aag cag ata agt agc agt tca act gga<br>Pro Pro Arg Glu Asn Gly His Lys Gln Ile Ser Ser Ser Ser Thr Gly<br>260                    265                  270 | 1356 | |
| tgt ctc tct tct cca aat gct aca gta caa agc cct aag cat gag tgg<br>Cys Leu Ser Ser Pro Asn Ala Thr Val Gln Ser Pro Lys His Glu Trp<br>275                    280                  285 | 1404 | |
| aaa atc gtt gct tca gaa aag act tca aat aac act tac ttg tgc ctg<br>Lys Ile Val Ala Ser Glu Lys Thr Ser Asn Asn Thr Tyr Leu Cys Leu<br>290                    295                  300                  305 | 1452 | |
| gct gtg ctg gat ggt ata ttc tgt gtc att ttt ctt cat ggg aga aac<br>Ala Val Leu Asp Gly Ile Phe Cys Val Ile Phe Leu His Gly Arg Asn<br>                 310                  315                  320 | 1500 | |
| agc cca cag agc tca cca aca agt act cca aaa cta agt aag agt tta<br>Ser Pro Gln Ser Ser Pro Thr Ser Thr Pro Lys Leu Ser Lys Ser Leu<br>                 325                  330                  335 | 1548 | |
| agc ttt gag atg caa caa gat gag cta atc gaa aag ccc atg tct cct<br>Ser Phe Glu Met Gln Gln Asp Glu Leu Ile Glu Lys Pro Met Ser Pro<br>        340                  345                  350 | 1596 | |
| atg cag tac gca cga tct ggt ctg gga aca gca gag atg aat ggc aaa<br>Met Gln Tyr Ala Arg Ser Gly Leu Gly Thr Ala Glu Met Asn Gly Lys<br>355                    360                  365 | 1644 | |
| ctc ata gct gca ggt ggc tat aac aga gag gaa tgt ctt cga aca gtc<br>Leu Ile Ala Ala Gly Gly Tyr Asn Arg Glu Glu Cys Leu Arg Thr Val<br>370                    375                  380                  385 | 1692 | |
| gaa tgc tat aat cca cat aca gat cac tgg tcc ttt ctt gct ccc atg<br>Glu Cys Tyr Asn Pro His Thr Asp His Trp Ser Phe Leu Ala Pro Met<br>                 390                  395                  400 | 1740 | |
| aga aca cca aga gcc cga ttt caa atg gct gta ctc atg ggc cag ctc<br>Arg Thr Pro Arg Ala Arg Phe Gln Met Ala Val Leu Met Gly Gln Leu<br>                 405                  410                  415 | 1788 | |
| tat gtg gta ggt gga tca aat ggc cac tca gat gac ctg agt tgt gga<br>Tyr Val Val Gly Gly Ser Asn Gly His Ser Asp Asp Leu Ser Cys Gly<br>        420                  425                  430 | 1836 | |
| gag atg tat gat tca aac ata gat gac tgg att cct gtt cca gaa ttg<br>Glu Met Tyr Asp Ser Asn Ile Asp Asp Trp Ile Pro Val Pro Glu Leu<br>435                    440                  445 | 1884 | |
| aga act aac cgt tgt aat gca gga gtg tgt gct ctg aat gga aag tta<br>Arg Thr Asn Arg Cys Asn Ala Gly Val Cys Ala Leu Asn Gly Lys Leu<br>450                    455                  460                  465 | 1932 | |
| tac atc gtt ggt ggc tct gat cca tat ggt caa aaa gga ctg aaa aat<br>Tyr Ile Val Gly Gly Ser Asp Pro Tyr Gly Gln Lys Gly Leu Lys Asn | 1980 | |

-continued

```
                        470                     475                     480
tgt gat gta ttt gat cct gta aca aag ttg tgg aca agc tgt gcc cct         2028
Cys Asp Val Phe Asp Pro Val Thr Lys Leu Trp Thr Ser Cys Ala Pro
                485                     490                     495 ctt aac att cgg aga cac cag tct gca gtc tgt gag ctt ggt ggt tat         2076
Leu Asn Ile Arg Arg His Gln Ser Ala Val Cys Glu Leu Gly Gly Tyr
            500                     505                     510 ttg tac ata atc gga ggt gca gaa tct tgg aat tgt ctg aac aca gta         2124
Leu Tyr Ile Ile Gly Gly Ala Glu Ser Trp Asn Cys Leu Asn Thr Val
        515                     520                     525 gaa cga tac aat cct gaa aat aat acc tgg act tta att gca ccc atg         2172
Glu Arg Tyr Asn Pro Glu Asn Asn Thr Trp Thr Leu Ile Ala Pro Met
530                     535                     540                     545 aat gtg gct agg cga gga gct gga gtg gct gtt ctt aat gga aaa ctg         2220
Asn Val Ala Arg Arg Gly Ala Gly Val Ala Val Leu Asn Gly Lys Leu
                550                     555                     560 ttt gta tgt ggt ggc ttt gat ggt tct cat gcc atc agt tgt gtg gaa         2268
Phe Val Cys Gly Gly Phe Asp Gly Ser His Ala Ile Ser Cys Val Glu
                565                     570                     575 atg tat gat cca act aga aat gaa tgg aag atg atg gga cat atg act         2316
Met Tyr Asp Pro Thr Arg Asn Glu Trp Lys Met Met Gly His Met Thr
            580                     585                     590 tca cca agg agc aat gct ggg att gca act gta ggg aac acc att tat         2364
Ser Pro Arg Ser Asn Ala Gly Ile Ala Thr Val Gly Asn Thr Ile Tyr
        595                     600                     605 gca gtg gag gat tcg atg gca atg aat ttc tgaatacggc ggaagtctat          2414
Ala Val Glu Asp Ser Met Ala Met Asn Phe
610                     615 aaccttgagt caaatgaatg gagcccctat acaaagattt tccagtttta acgggtttaa       2474
gaccctctca aactaacagg cttagtgatg taattatggt tagcagaggt acacttgtga       2534
ataaagaggg tgggtgggga tagatgttgc taacagcaac acaaagcttt tgcatattgc       2594
atactattaa acatgctgta catactttt gggtttattt gggaaggaat gcaaagatga        2654
aggtctgttt gtgtactttt aagactttgg ttattttact ttttggaaaa gataaaccaa       2714
gaattgattg ggcacatcaa aaaaaaaaaa aaaaaaa                                2752
```

```
<210> SEQ ID NO 15
<211> LENGTH: 619
<212> TYPE: PRT
<213> ORGANISM: Homo sapiens

<400> SEQUENCE: 15

Met Ile Pro Asn Gly Tyr Leu Met Phe Glu Asp Glu Asn Phe Ile Glu
1               5                   10                  15

Ser Ser Val Ala Lys Leu Asn Ala Leu Arg Lys Ser Gly Gln Phe Cys
            20                  25                  30

Asp Val Arg Leu Gln Val Cys Gly His Glu Met Leu Ala His Arg Ala
        35                  40                  45

Val Leu Ala Cys Cys Ser Pro Tyr Leu Phe Glu Ile Phe Asn Ser Asp
    50                  55                  60

Ser Asp Pro His Gly Ile Ser His Val Lys Phe Asp Asp Leu Asn Pro
65                  70                  75                  80

Glu Ala Val Glu Val Leu Leu Asn Tyr Ala Tyr Thr Ala Gln Leu Lys
                85                  90                  95

Ala Asp Lys Glu Leu Val Lys Asp Val Tyr Ser Ala Ala Lys Glu Leu
            100                 105                 110
```

-continued

```
Lys Met Asp Arg Val Lys Gln Val Cys Gly Asp Tyr Leu Leu Ser Arg
        115                 120                 125
Met Asp Val Thr Ser Cys Ile Ser Tyr Arg Asn Phe Ala Ser Cys Met
    130                 135                 140
Gly Asp Ser His Leu Leu Asn Lys Val Asp Ala Tyr Ile Gln Glu His
145                 150                 155                 160
Leu Leu Gln Ile Ser Glu Glu Glu Phe Leu Lys Leu Pro Arg Leu
                165                 170                 175
Lys Leu Glu Val Met Leu Glu Asp Asn Val Cys Leu Pro Ser Asn Gly
            180                 185                 190
Lys Leu Tyr Thr Lys Val Ile Asn Trp Val Gln Arg Ser Ile Trp Glu
        195                 200                 205
Asn Gly Asp Ser Leu Glu Glu Leu Met Glu Glu Val Gln Thr Leu Tyr
    210                 215                 220
Tyr Ser Ala Asp His Lys Leu Leu Asp Gly Asn Leu Leu Asp Gly Gln
225                 230                 235                 240
Ala Glu Val Phe Gly Ser Asp Asp His Ile Gln Phe Val Gln Lys
                245                 250                 255
Lys Pro Pro Arg Glu Asn Gly His Lys Gln Ile Ser Ser Ser Thr
        260                 265                 270
Gly Cys Leu Ser Ser Pro Asn Ala Thr Val Gln Ser Pro Lys His Glu
        275                 280                 285
Trp Lys Ile Val Ala Ser Glu Lys Thr Ser Asn Asn Thr Tyr Leu Cys
    290                 295                 300
Leu Ala Val Leu Asp Gly Ile Phe Cys Val Ile Phe Leu His Gly Arg
305                 310                 315                 320
Asn Ser Pro Gln Ser Ser Pro Thr Ser Thr Pro Lys Leu Ser Lys Ser
                325                 330                 335
Leu Ser Phe Glu Met Gln Gln Asp Glu Leu Ile Glu Lys Pro Met Ser
                340                 345                 350
Pro Met Gln Tyr Ala Arg Ser Gly Leu Gly Thr Ala Glu Met Asn Gly
        355                 360                 365
Lys Leu Ile Ala Ala Gly Gly Tyr Asn Arg Glu Glu Cys Leu Arg Thr
        370                 375                 380
Val Glu Cys Tyr Asn Pro His Thr Asp His Trp Ser Phe Leu Ala Pro
385                 390                 395                 400
Met Arg Thr Pro Arg Ala Arg Phe Gln Met Ala Val Leu Met Gly Gln
                405                 410                 415
Leu Tyr Val Val Gly Gly Ser Asn Gly His Ser Asp Asp Leu Ser Cys
            420                 425                 430
Gly Glu Met Tyr Asp Ser Asn Ile Asp Asp Trp Ile Pro Val Pro Glu
        435                 440                 445
Leu Arg Thr Asn Arg Cys Asn Ala Gly Val Cys Ala Leu Asn Gly Lys
    450                 455                 460
Leu Tyr Ile Val Gly Gly Ser Asp Pro Tyr Gly Gln Lys Gly Leu Lys
465                 470                 475                 480
Asn Cys Asp Val Phe Asp Pro Val Thr Lys Leu Trp Thr Ser Cys Ala
                485                 490                 495
Pro Leu Asn Ile Arg Arg His Gln Ser Ala Val Cys Glu Leu Gly Gly
            500                 505                 510
Tyr Leu Tyr Ile Ile Gly Gly Ala Glu Ser Trp Asn Cys Leu Asn Thr
        515                 520                 525
Val Glu Arg Tyr Asn Pro Glu Asn Asn Thr Trp Thr Leu Ile Ala Pro
```

-continued

```
              530                 535                 540
Met Asn Val Ala Arg Arg Gly Ala Gly Val Ala Val Leu Asn Gly Lys
545                 550                 555                 560

Leu Phe Val Cys Gly Gly Phe Asp Gly Ser His Ala Ile Ser Cys Val
                565                 570                 575

Glu Met Tyr Asp Pro Thr Arg Asn Glu Trp Lys Met Met Gly His Met
            580                 585                 590

Thr Ser Pro Arg Ser Asn Ala Gly Ile Ala Thr Val Gly Asn Thr Ile
        595                 600                 605

Tyr Ala Val Glu Asp Ser Met Ala Met Asn Phe
    610                 615
```

<210> SEQ ID NO 16
<211> LENGTH: 47
<212> TYPE: PRT
<213> ORGANISM: Homo sapiens

<400> SEQUENCE: 16

```
Lys Leu Ile Ala Ala Gly Gly Tyr Asn Arg Glu Glu Cys Leu Arg Thr
1               5                   10                  15

Val Glu Cys Tyr Asn Pro His Thr Asp His Trp Ser Phe Leu Ala Pro
            20                  25                  30

Met Arg Thr Pro Arg Ala Arg Phe Gln Met Ala Val Leu Met Gly
        35                  40                  45
```

<210> SEQ ID NO 17
<211> LENGTH: 48
<212> TYPE: PRT
<213> ORGANISM: Homo sapiens

<400> SEQUENCE: 17

```
Gln Leu Tyr Val Val Gly Gly Ser Asn Gly His Ser Asp Asp Leu Ser
1               5                   10                  15

Cys Gly Glu Met Tyr Asp Ser Asn Ile Asp Asp Trp Ile Pro Val Pro
            20                  25                  30

Glu Leu Arg Thr Asn Arg Cys Asn Ala Gly Val Cys Ala Leu Asn Gly
        35                  40                  45
```

<210> SEQ ID NO 18
<211> LENGTH: 49
<212> TYPE: PRT
<213> ORGANISM: Homo sapiens

<400> SEQUENCE: 18

```
Lys Leu Tyr Ile Val Gly Gly Ser Asp Pro Tyr Gly Gln Lys Gly Leu
1               5                   10                  15

Lys Asn Cys Asp Val Phe Asp Pro Val Thr Lys Leu Trp Thr Ser Cys
            20                  25                  30

Ala Pro Leu Asn Ile Arg Arg His Gln Ser Ala Val Cys Glu Leu Gly
        35                  40                  45

Gly
```

<210> SEQ ID NO 19
<211> LENGTH: 47
<212> TYPE: PRT
<213> ORGANISM: Homo sapiens

<400> SEQUENCE: 19

```
Tyr Leu Tyr Ile Ile Gly Gly Ala Glu Ser Trp Asn Cys Leu Asn Thr
```

```
                1               5                  10                 15
Val Glu Arg Tyr Asn Pro Glu Asn Thr Trp Thr Leu Ile Ala Pro
                        20                  25                 30
Met Asn Val Ala Arg Arg Gly Ala Gly Val Ala Val Leu Asn Gly
                35                  40                  45
```

<210> SEQ ID NO 20
<211> LENGTH: 47
<212> TYPE: PRT
<213> ORGANISM: Homo sapiens

<400> SEQUENCE: 20

```
Lys Leu Phe Val Cys Gly Gly Phe Asp Gly Ser His Ala Ile Ser Cys
 1               5                  10                  15
Val Glu Met Tyr Asp Pro Thr Arg Asn Glu Trp Lys Met Met Gly His
                        20                  25                  30
Met Thr Ser Pro Arg Ser Asn Ala Gly Ile Ala Thr Val Gly Asn
                35                  40                  45
```

<210> SEQ ID NO 21
<211> LENGTH: 22
<212> TYPE: PRT
<213> ORGANISM: Homo sapiens

<400> SEQUENCE: 21

```
Lys Leu Tyr Gly Gly Leu Val Glu Tyr Asp Pro Trp Ala Pro Met Arg
 1               5                  10                  15
Ala Gly Val Ala Leu Gly
                20
```

<210> SEQ ID NO 22
<211> LENGTH: 19
<212> TYPE: PRT
<213> ORGANISM: Homo sapiens

<400> SEQUENCE: 22

```
Ala Ser Gln Gly Thr Lys Arg Ser Tyr Glu Gln Met Glu Thr Asp Gly
 1               5                  10                  15
Glu Arg Gln
```

<210> SEQ ID NO 23
<211> LENGTH: 8
<212> TYPE: PRT
<213> ORGANISM: Homo sapiens
<220> FEATURE:
<221> NAME/KEY: SITE
<222> LOCATION: (5)...(7)
<223> OTHER INFORMATION: Xaa=unknown amino acid residue

<400> SEQUENCE: 23

```
Thr Lys Arg Ser Xaa Xaa Xaa Met
 1               5
```

<210> SEQ ID NO 24
<211> LENGTH: 19
<212> TYPE: DNA
<213> ORGANISM: Artificial Sequence
<220> FEATURE:
<223> OTHER INFORMATION: oligonucleotide

<400> SEQUENCE: 24
gcaaagcagg agaaaccac                                              19

```
<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
gggtccatct gatagatatg agag                                          24

<210> SEQ ID NO 26
<211> LENGTH: 48
<212> TYPE: DNA/RNA
<213> ORGANISM: Artificial Sequence
<220> FEATURE:
<223> OTHER INFORMATION: primer
<221> NAME/KEY: modified_base
<222> LOCATION: all "n" positions
<223> OTHER INFORMATION: I

<400> SEQUENCE: 26
cuacuacuac uaggccacgc gtcgactact acgggnnggg nngggnng                48

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
tcctgatgtt gctgtagacg                                               20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
gcacgactag tatgatttgc                                               20

<210> SEQ ID NO 29
<211> LENGTH: 8
<212> TYPE: PRT
<213> ORGANISM: Homo sapiens

<400> SEQUENCE: 29

Thr Gly Ala Gly Ala Gly Cys Gly
 1               5

<210> SEQ ID NO 30
<211> LENGTH: 5
<212> TYPE: PRT
<213> ORGANISM: Homo sapiens

<400> SEQUENCE: 30

Tyr Ser Ala Ala Lys
 1               5

<210> SEQ ID NO 31
<211> LENGTH: 20
<212> TYPE: DNA
<213> ORGANISM: Artificial Sequence
<220> FEATURE:
```

<223> OTHER INFORMATION: oligonucleotide

<400> SEQUENCE: 31
cattcctctc tgttatagcc                                                     20

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
ccacctgcag ctatgag                                                        17

<210> SEQ ID NO 33
<211> LENGTH: 14
<212> TYPE: PRT
<213> ORGANISM: VSV

<400> SEQUENCE: 33

Lys Leu Gly Ile Ala Pro Pro Tyr Glu Glu Asp Thr Ser
1               5                   10

<210> SEQ ID NO 34
<211> LENGTH: 14
<212> TYPE: PRT
<213> ORGANISM: VSV

<400> SEQUENCE: 34

Lys Lys Met Gly Leu Pro Pro Tyr Asp Glu Ser Cys Pro
1               5                   10

<210> SEQ ID NO 35
<211> LENGTH: 14
<212> TYPE: PRT
<213> ORGANISM: Rabies virus

<400> SEQUENCE: 35

Asp Leu Trp Leu Pro Pro Pro Glu Tyr Val Pro Leu Lys Glu
1               5                   10

<210> SEQ ID NO 36
<211> LENGTH: 14
<212> TYPE: PRT
<213> ORGANISM: PIRY

<400> SEQUENCE: 36

Met Glu Trp Glu Ser Pro Pro Ser Tyr Asn Glu Ile Lys Ser
1               5                   10

<210> SEQ ID NO 37
<211> LENGTH: 14
<212> TYPE: PRT
<213> ORGANISM: Carp virus

<400> SEQUENCE: 37

Lys Ser Lys Gly Thr Pro Pro Thr Tyr Glu Glu Thr Leu Ala
1               5                   10

<210> SEQ ID NO 38
<211> LENGTH: 14
<212> TYPE: PRT
<213> ORGANISM: Ebola virus

-continued

```
<400> SEQUENCE: 38

Ile Leu Pro Thr Ala Pro Pro Glu Tyr Met Glu Ala Ile Tyr
1               5                   10

<210> SEQ ID NO 39
<211> LENGTH: 14
<212> TYPE: PRT
<213> ORGANISM: Marburg virus

<400> SEQUENCE: 39

Met Gln Tyr Leu Asn Pro Pro Pro Tyr Ala Asp His Gly Ala
1               5                   10

<210> SEQ ID NO 40
<211> LENGTH: 11
<212> TYPE: PRT
<213> ORGANISM: Homo sapiens
<220> FEATURE:
<221> NAME/KEY: SITE
<222> LOCATION: (2)
<223> OTHER INFORMATION: Xaa=unknown amino acid residue
<221> NAME/KEY: SITE
<222> LOCATION: (9)...(10)
<223> OTHER INFORMATION: Xaa=unknown amino acid residue

<400> SEQUENCE: 40

Ser Xaa Gly Thr Lys Arg Ser Tyr Xaa Xaa Met
1               5                   10

<210> SEQ ID NO 41
<211> LENGTH: 8
<212> TYPE: PRT
<213> ORGANISM: Homo sapiens
<220> FEATURE:
<221> NAME/KEY: SITE
<222> LOCATION: (5)...(7)
<223> OTHER INFORMATION: Xaa=unknown amino acid residue

<400> SEQUENCE: 41

Thr Lys Arg Ser Xaa Xaa Xaa Met
1               5

<210> SEQ ID NO 42
<211> LENGTH: 11
<212> TYPE: PRT
<213> ORGANISM: Homo sapiens

<400> SEQUENCE: 42

Cys Gly Asp Leu Arg Leu Thr Leu Leu Glu Leu
1               5                   10
```

IDENTIFICATION AND USE OF ANTIVIRAL COMPOUNDS THAT INHIBIT INTERACTION OF HOST CELL PROTEINS AND VIRAL PROTEINS REQUIRED FOR VIRAL REPLICATION

The present invention is a continuation-in-part of U.S. patent application Ser. No. 08/444,994, filed on May 19, 1995 and is entitled to and claims priority benefit to U.S. provisional application Serial No. 60/148,263, filed on Aug. 11, 1999, the entire contents of each of which is incorporated herein by reference in its entirety.

The work reflected in this application was supported, in part, by a grant from the National Institutes of Health, and the Government may have certain rights in the invention.

1. INTRODUCTION

The present invention relates to the identification of new cellular targets for viral intervention, the identification of antiviral compounds that act on the new targets, and the therapeutic use of such antiviral compounds.

2. BACKGROUND OF THE INVENTION

Replication of viruses can induce drastic changes in the infected host cell metabolism. The analysis of the replication cycle of viruses by molecular biological techniques has facilitated the identification and study of viral gene products that modulate and affect cellular functions (Knipe, 1996, in Fields Virology-1996, Fields, et al., eds., Raven Publishers, Philadelphia, Pa., p. 273–299).

2.1. Influenza a Viral Gene Products that Modulate host Cellular Functions

Influenza A virus is a negative strand RNA virus belonging to the orthomyxovinis family. The genome of the virus consists of 8 segments and encodes 10 polypeptides. Experimental evidence generated in the laboratory of Scholtissek indicates that the nucleoprotein (NP) is a major determinant of species specificity of influenza viruses (Scholtissek, et al., 1985, Virology 147: 287–294).

2.1.1. NP PROTEIN

Transcription and replication of influenza virus RNA takes place in the nucleus of the infected cell. Transcription and replication of influenza virus RNA requires four virus encoded proteins: the NP and the three components of the viral RNA-dependent RNA polymerase, PB1, PB2 and PA (Huang, et al., 1990, J. Virol. 64: 5669–5673). The NP is the major structural component of the virion that interacts with genomic RNA, and is required for antitermination during RNA synthesis (Beaton & Krug, 1986, Proc. Natl. Acad. Sci. USA 83:6282–6286). NP is also required for elongation of RNA chains (Shapiro & Krug, 1988, J. Virol. 62: 2285–2290) but not for initiation (Honda, et al., 1988, J. Biochem. 104: 1021–1026).

Phylogenetic analysis divides NP genes into two families: one containing NPs predominantly of avian origin, and one containing those of human origin (Bean, 1984, Virology 133: 438–442; Buckler-White & Murphy, 1986, Virology 155: 345–355; Gammelin, et al., 1989, Virology 170: 71–80; Scholtissek, et al., 1985, Virology 147: 287–294). The human virus A/HK/1/68 and viruses having genetically related NPs cannot rescue mutants of the avian virus A/FPV/Rostock/1/34 (FPV) with temperature sensitive (ts) defects in the NP following double infection of chicken embryo fibroblasts (CEF) at 40° C. (Scholtissek, et al., 1985, Virology 147: 287–294; Scholtissek, et al., 1978, Virology 91: 79–85). However, the human viruses that failed to rescue the ts mutants on CEF cells were able to do so on Madin-Darby canine kidney (MDCK) cells (Scholtissek, et al., 1978, Virology 91: 79–85). Additionally, A/HK/1/68 virus and A/FPV/Rostock/1/34 virus reassortants containing the A/HK/1/68 virus-derived NP replicate in MDBK cells (bovine kidney) but not in CEFs (Scholtissek, et al., 1978, Virology 91: 79–85). The host-specific rescue of FPV ts mutants and the host restriction of A/HK/1/68 virus reassortants suggest that a factor(s) of host origin, which differs between mammalian and avian cells, is responsible for this phenomenon, and that this factor may interact with the influenza A virus NP. However, no host protein(s) that interacts with NP during infection has previously been identified or characterized.

2.1.2. NS1 PROTEIN

The NS1 protein of influenza A viruses is known to modulate and affect cellular functions. The NS1 is the only non-structural protein of the virus and is abundantly expressed in infected cells (Lazarowitz, et al., 1971, Virology 46: 830–843).

Several regulatory finctions of the NS1 protein have been identified. The NS1 protein may influence multiple steps of gene expression including pre-mRNA splicing (Fortes, et al., 1994, EMBO J. 13: 704–712; Lu, et al., 1994, Genes Dev. 8: 1817–1828), nucleo-cytoplasmic transport of poly(A)-RNA (Fortes, et al., 1994, EMBO J. 13: 704–712; Qiu, Y., et al., 1994, J. Virology 68: 2425–2432) and translation (De La Luna, S., et al., 1995, J. Virol. 69: 2427–2433; Enami, K., et al., 1994, J. Virol. 68: 1423–1427). In addition, NS1 can block the activation of the double-stranded RNA (dsRNA) activated protein kinase (PKR), presumably due to its dsRNA binding activity (Lu, et al., 1995, Virology 214: 222–228). The activation of PKR results in a downregulation of translation and is part of the cellular antiviral defense mechanisms The NS1 protein may counteract this cellular response in order to synthesize high levels of viral proteins in the infected cell (Lu, et al., 1995, Virology 214: 222–228). These pleiotropic effects may singly or combined provide the molecular basis for the role that the NS 1 protein plays in determining the host range and virulence of influenza virus strains (Shimizu K., et al., 1983, Virology 124: 35–44; Treanor, J. J., etal., 1989, Virology 171: 1–9).

Despite these studies examining the activities of NS1 and its interactions with various RNAs, little is known about the cellular factors that are recognized by the NS1 protein and that may therefore be central to NS1 functions.

2.2. RHABDOVIRUS GENE PRODUCTS THAT MODULATE HOST CELLULAR FUNCTIONS

Viruses belonging to the Rhabdoviridae family cause disease in a wide variety of species including vertebrates, invertebrates, and plants (Wagner & Rose, 1996, In Fields, et al., (eds.), *Fields Virology*, 3rd edition, Lippincott-Raven Publishers, Philadelphia, pp. 1121–1135). Two prototypic members of the Rhabdoviridae family include vesicular stomatitis virus (VSV; genus=vesiculovirus) and rabies virus (genus=lyssavirus). Like influenza A virus, rhabdoviruses possess a negative-strand RNA genome. Rhabdoviruses replicate exclusively in the cytoplasm of infected cells, and derive their lipid envelope via budding through the cytoplasmic membrane (for review see Wagner & Rose, 1996, In Fields, et al., (eds.), *Fundamental Virology*, 3rd edition, Lippincott-Raven Publishers, Philadelphia, pp. 1121–1135).

2.2.1. MATRIX (M) PROTEIN

Many aspects of the replication process of rhabdoviruses remain unclear. The major structural protein of rhabdoviruses, the matrix (M) protein, is thought to play a key role in viral assembly and release (Chong & Rose, 1993, J. Virol., 67, 407–414; Chong & Rose, 1994, J. Virol., 68, 441–447; Kaptur, et al., 1995, Virology, 206, 894–903; Lenard, 1996, Virology, 216, 289–298; Lyles, et al., 1992, J. Virol., 66, 349–358; McCreedy & Lyles, 1989, Virus Res., 14, 189–205; Mebatsion, et al., 1996, Cell, 84, 941–951; Pal & Wagner, 1987, In, Wagner (ed.), *The Rhabdoviruses*. Plenum, New York, pp. 75–128; Newcomb, et al., 1982, J. Virol., 41, 1055–1062; Zakowski, et al., 1981, Biochemistry, 20, 3902–3907). When the M protein of VSV is expressed in mammalian cells or a baculovirus system in the absence of any other viral protein, M protein is released from the cells in the form of lipid vesicles by budding through the cytoplasmic membrane (Justice, et al., 1995, J. Virol., 69, 3156–3160; Li, et al., 1993, J. Virol., 67, 4415–4420). The N-terminal portion of the VSV M protein has been shown to be important for membrane localization, and thus the budding process (Chong & Rose, 1993, J. Virol., 67, 407–414; Chong and Rose, 1994, J. Virol., 68, 441–447; Lenard and Vanderoef, 1990, J. Virol., 64, 3486–3491; Ye, et al., 1994, J. Virol. 68, 7386–7396; Zakowski and Wagner, 1980, J. Virol., 36, 93–102). The precise mechanism of how M is released from cells and the potential function(s) of host proteins in the budding process remain unclear.

The role of the M protein in rhabdoviral assembly has been compared to that of the gag protein in retroviral assembly (Lenard, 1996, Virology, 216, 289–298). The gag protein of Rous sarcoma virus (RSV) and the M protein of VSV share the ability to associate with the cytoplasmic membrane, and to bud from cells independent of other viral proteins (Justice, et al., 1995, J. Virol., 69, 3156–3160; Li, et al., 1993, J. Virol., 67, 4415–4420; Wills, et al., 1994, J. Virol., 68, 6605–6618). In addition to the membrane association (MA) domain of RSV gag, a late (L) budding domain has been identified in the p2b protein of RSV gag and shown to play an essential role in the late stage of budding (Wills, et al., 1994, J. Virol., 68, 6605–6618).

Interestingly, a sequence in the RSV L domain (PPPY) matches the sequence of the consensus motif required for interacting with WW domains of cellular proteins (Chen and Sudol, 1996, Techniques in Protein Chemistry VII, 7, 3–12; Chen, et al., 1997, J. Biol. Chem., 272, 17070–17077; Macias, et al., 1996, Nature, 382, 646–649; Sudol, et al., 1995, J. Biol. Chem., 270, 14733–14741). While L domains have been identified in the gag proteins of other retroviruses, only the gag proteins of the oncoviruses appear to have the PPXY motif conserved (Gottlinger, et al., 1991, Proc. Natl. Acad. Sci. USA., 88, 3195–3199; Huang, et al., 1995, J. Virol., 69, 6810–6818; Parent, et al., 1995, J. Virol., 69, 5455–5460; Puffer, et al., 1997, J. Virol., 71, 6541–6546; Wills, et al., 1994, J. Virol., 68, 6605–6618). The recently described WW domain is (i) a highly structured, modular domain that mediates protein-protein interactions, (ii) present in a wide range of cellular proteins with unrelated functions, and (iii) functionally similar to, but structurally distinct from, Src homology-3 (SH3) domains (for review see Sudol, 1996, In Blundell, et al., (eds.) *Prog Biophys. Molec. Biol.*, Vol. 65, Elsevier Science Ltd., Great Britain, pp. 113–132). The biology of the WW domain and its interacting ligands have been implicated in playing a role in a number of disease states including Liddle's syndrome (a genetic form of hypertension), muscular dystrophy, and Alzheimer's disease (Bork and Sudol, 1994, Trends Biochem. Sci., 19, 531–533; Einbond and Sudol, 1996, FEBS Lett., 384, 1–8; Staub, et al., 1996, EMBO J., 15, 2371–2380; Sudol, 1996, In Blundell, et al., (eds.) *Prog. Biophys. Molec. Biol.*, Vol. 65, Elsevier Science Ltd., Great Britain, pp. 113–132). In addition, the WW domain has also been implicated in the biology of retroviral budding and assembly (Gamier, et al., 1996, Nature, 381, 744–745; Sudol, 1996, In Blundell, et al., (eds.) *Prog. Biophys. Molec. Biol.*, Vol. 65, Elsevier Science L td., Great Britain, pp. 113–132). Indeed, the L domain of RSV gag mentioned above has been shown recently to interact with the WW domain of the cellular Yes-kinase associated protein (YAP) (Garnier, et al., 1996, Nature, 381, 744–745; Sudol, 1994, Oncogene, 9, 2145–2152).

Thus, little is known about host cell functions that contribute to the intracellular replication of negative-strand RNA viruses such as influenza and rhabdoviruses. No cellular factors, or interactions between cellular factors and viral proteins, have been previously characterized that can be used as targets for therapeutic intervention.

3. SUMMARY OF THE INVENTION

The present invention relates to the identification of host cell proteins that interact with viral proteins required for virus replication, and high throughput assays to identify compounds that interfere with the specific interaction between the viral and host cell protein. Interfering compounds that inhibit viral replication can be used therapeutically to treat viral infection.

The invention is based, in part, on the Applicants' discovery of novel interactions between viral proteins such as NP and NS1 nfluenza proteins, the rhabdovirus M protein, and human host cell proteins or protein domains referred to herein as NPI-1, NPI-2, NPI-3, NPI-4, NPI-5, NPI-6, NS1I-1, NS1-BP, and cellular proteins containing WW domains, respectively. Host cell protein s such as NPI-1 and NS1I-1 may be accessory proteins required for replication of the viruses. Compounds that interfere with the binding of viral proteins with host cell proteins or protein domains, and that inhibit viral replication, can be useful for treating viral infection in vivo.

4. DESCRIPTION OF THE FIGURES

Figure 1B:
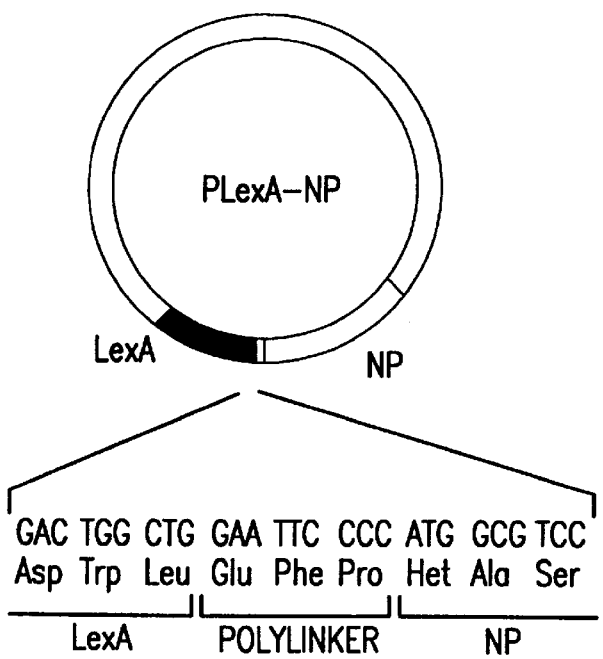

FIGS. 1A and 1B: The interactive trap system, as used in the identification of NP- and NS1-interacting proteins. FIG. 1A: R100 contains the reporter gene LexAop-LEU2 and a transcriptionally inactive LexA-NP fusion protein (left). Libra ry proteins are synthesized in R100 transformants in media containing galactose. If the library protein does not interact with the LexA-NP fusion protein, then the LEU2 gene is not transcribed (middle). If the library protein does interact with the LexA-NP fusion protein, then the LEU2 gene is transcriptionally active, and the cell forms a colony on leu⁻ medium (right). FIG. 1B: The pLexA-NP bait plasmid used in the interactive trap. The coding region of influenza A/PR/8/34 virus nucleoprotein (NP) was subcloned into the EcoRI and Sal I restriction sites of pEG202. This construction encodes a fusion protein which includes 202 amino acids of LexA and the entire coding region of NP (498 amino acids) separated by 3 amino acids encoded by polylinker sequences derived from the cloning process. The nucleotide sequence and amino acid sequence depicted correspond to SEQ ID NO: 1 and SEQ ID NO:2, respectively.

FIGS. 2A–2D: Nucleotide sequence of NPI-1 cDNA (SEQ ID NO:3)and the encoded polypeptide sequence (SEQ ID NO:4).

FIGS. 3A–3B: Comparison of the amino acid sequence of NPI-1 (SEQ ID NO:4) and the amino acid sequence of SRP1 (SEQ ID NO:5). Vertical lines indicate identity; colons and periods indicate conservative changes (Deveraux, et al., 1984, Nucl. Acids Res. 12: 387–395). 42 amino acid ARM repeats are aligned vertically according to Peifer, et al., 1994, Cell 76: 789–791. For a complete comparison of SRP1 to other ARM repeat containing proteins, see Peifer, et al., 1994, Cell 76: 789–791. The ARM consensus sequence is indicated at the bottom; "+" indicates K,R, or H; "−" indicates D or E; "~" indicates a gap. Since other residues are conserved within the repeats of NPI-1 and SRP1, a consensus sequence derived from only these two proteins is also shown.

Figure 4:
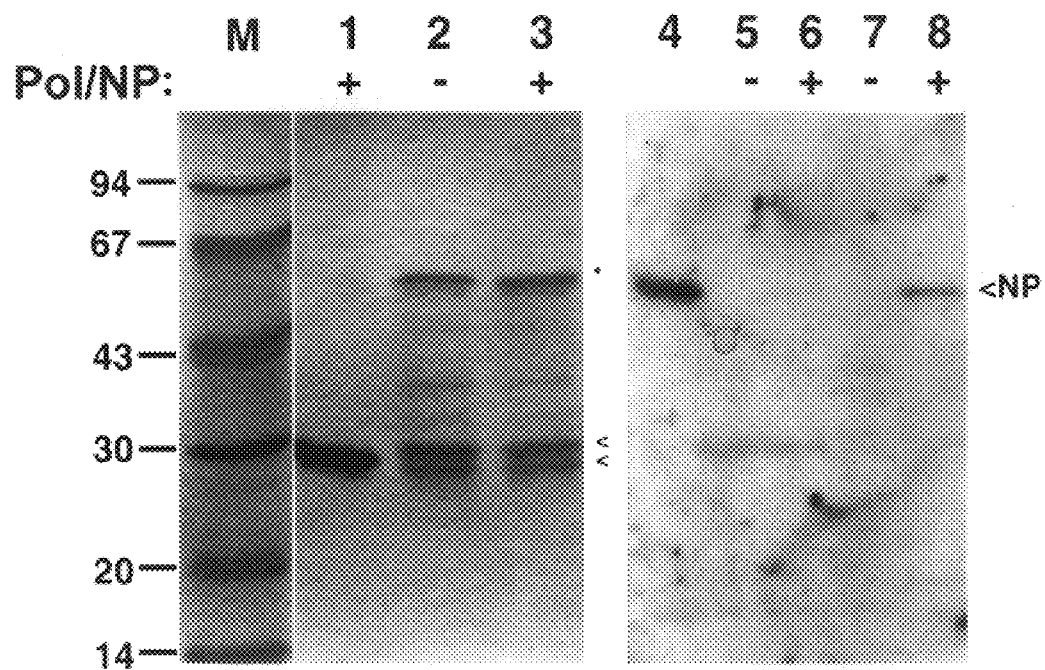

FIG. 4: GST-NPI-1 binds to NP in vitro. GST (lanes 1, 5, 6) and GST-NPI-1 (lanes 2, 3, 7, 8) were expressed in bacteria and precipitated from cell lysates on glutathione agarose beads. The complexed beads were then incubated with partially purified influenza virus NP and polymerase preparations (Pol/NP) as indicated. Precipitated proteins were fractionated on a 12.5% SDS polyacrylamide gel, and either stained with Coomassie blue (lanes 1 to 3), or immunoblotted using the monoclonal antibody HT103 directed against the viral nucleoprotein (lanes 4 to 8). Unprecipitated Pol/NP was separated in lane 4. M, protein molecular weight markers; *, GST-NPI-1 fusion protein; arrows indicate major fusion protein degradation products.

Figure 5:
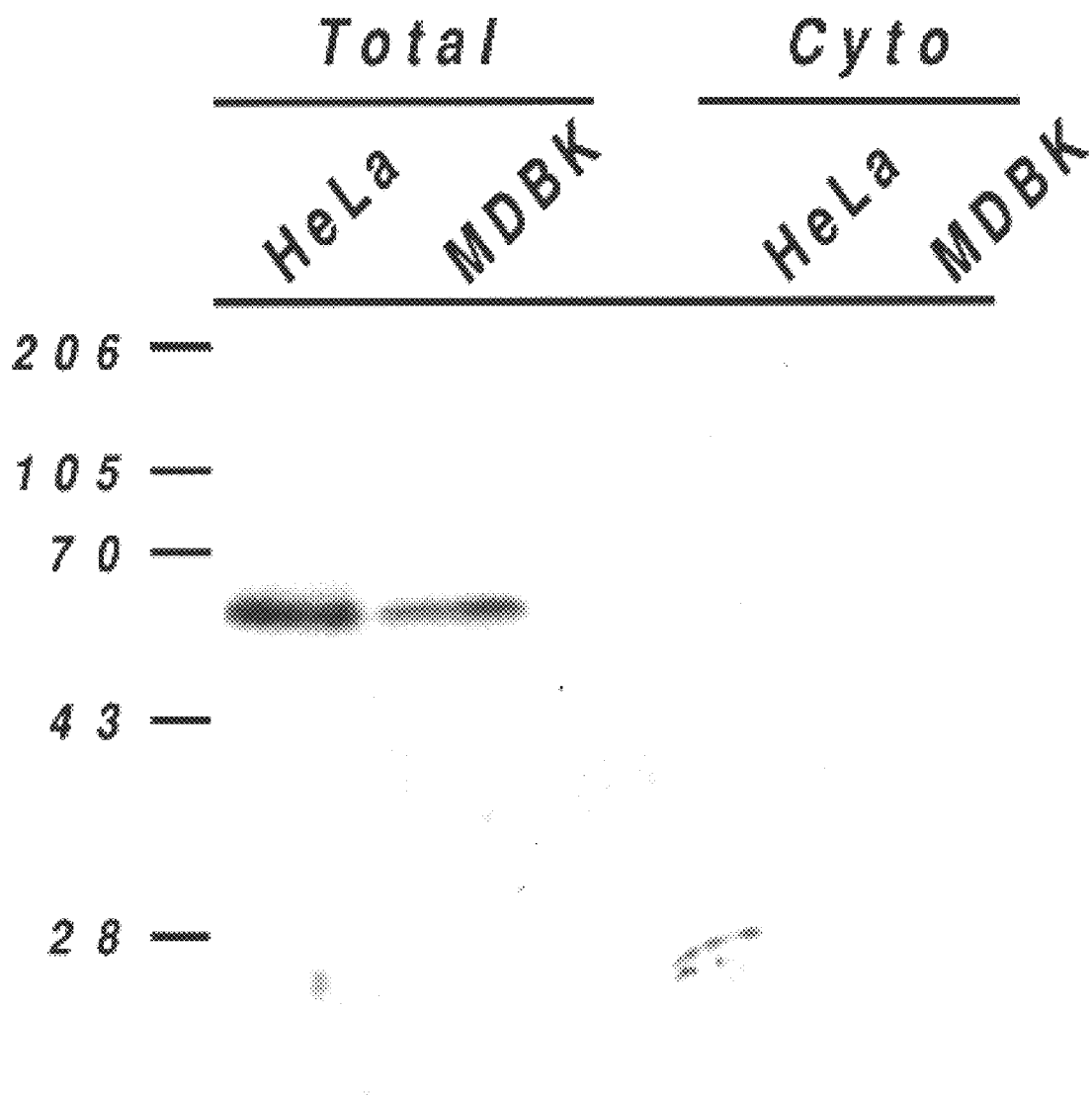

FIG. 5: Immunoblot of total cellular proteins using polyclonal rabbit sera against NPI-1. Total cell lysates and cytoplasmic cell extracts from HeLa and MDBK cell lines were separated by SDS-PAGE, transferred to nitrocellulose, immunoblotted with anti-NPI-1 sera, and developed by $^{125}$I-protein A. Each lane contains protein from $1 \times 10^5$ cells.

Figure 6:
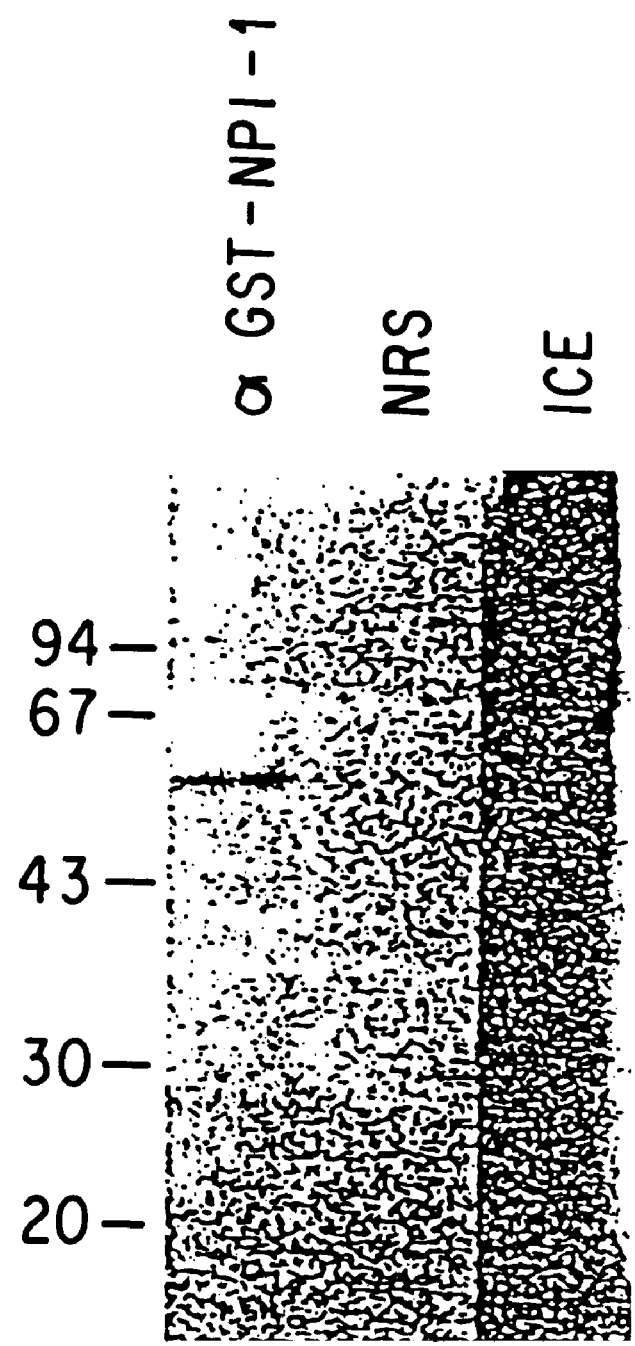

FIG. 6: NP is co-immunoprecipitated from influenza A virus infected cells by antisera against NPI-1. Infected HeLa cell proteins were labeled with $^{35}$S-methionine and $^{35}$S-cysteine, and total cell lysates were made as described in the text. Complexes of NPI-1 and NP were precipitated using anti-NPI-1 sera. Precipitated proteins were then fractionated by SDS-PAGE and detected by autoradiography.

FIGS. 7–11: Partial DNA sequences of isolated coding regions of five different proteins that interact withthe NP of influenza A, as detected using the interactive trap system in yeast. The proteins whose sequences are provided are as follows:

FIG. 7: Partial nucleotide sequence of NPI-2 (SEQ ID NO:6).

FIGS. 8A–8C: Partial nucleotide sequence of NPI-3 (SEQ ID NO:7) and the amino acid sequence encoded by the partial nucleotide sequence (SEQ ID NO:8).

FIG. 9: Partial nucleotide sequence of NPI-4 (SEQ ID NO:9).

FIG. 10: Partial nucleotide sequence of NPI-5 (SEQ ID NO:10).

FIG. 11: Partial nucleotide sequence of NPI-6 (SEQ ID NO:11).

FIGS. 12A–12D: Nucleotide sequence of the NS1I-1 gene (SEQ ID NO:12) and the encoded amino acid sequence of the NS1I-1 protein (SEQ ID NO:13). The sequence of 2572 bp was determined by dideoxy sequencing of two overlapping clones. The first clone, pK5, was isolated from the yeast library and contains the HeLa cell cDNA comprising nucleotide positions 791 to 2572. The second clone, pRACENS1I-1, resulted from the 5'RACE procedure used to obtain cDNA derived from the 5'-end of NS1I-1 mRNA, and comprises nucleotide positions 1 to 944.

Figure 13:
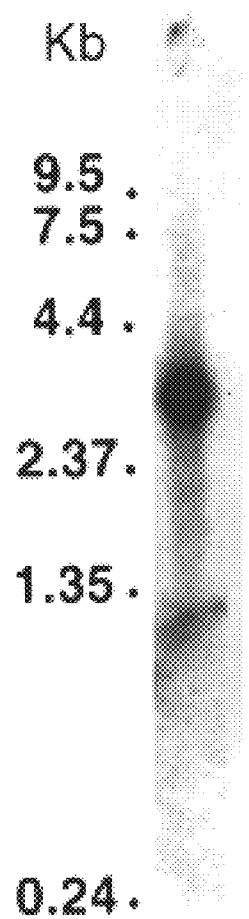

FIG. 13: Northern blot analysis of HeLa cell poly(A)-RNA using an NS1I-1-specific probe.

Figure 14:
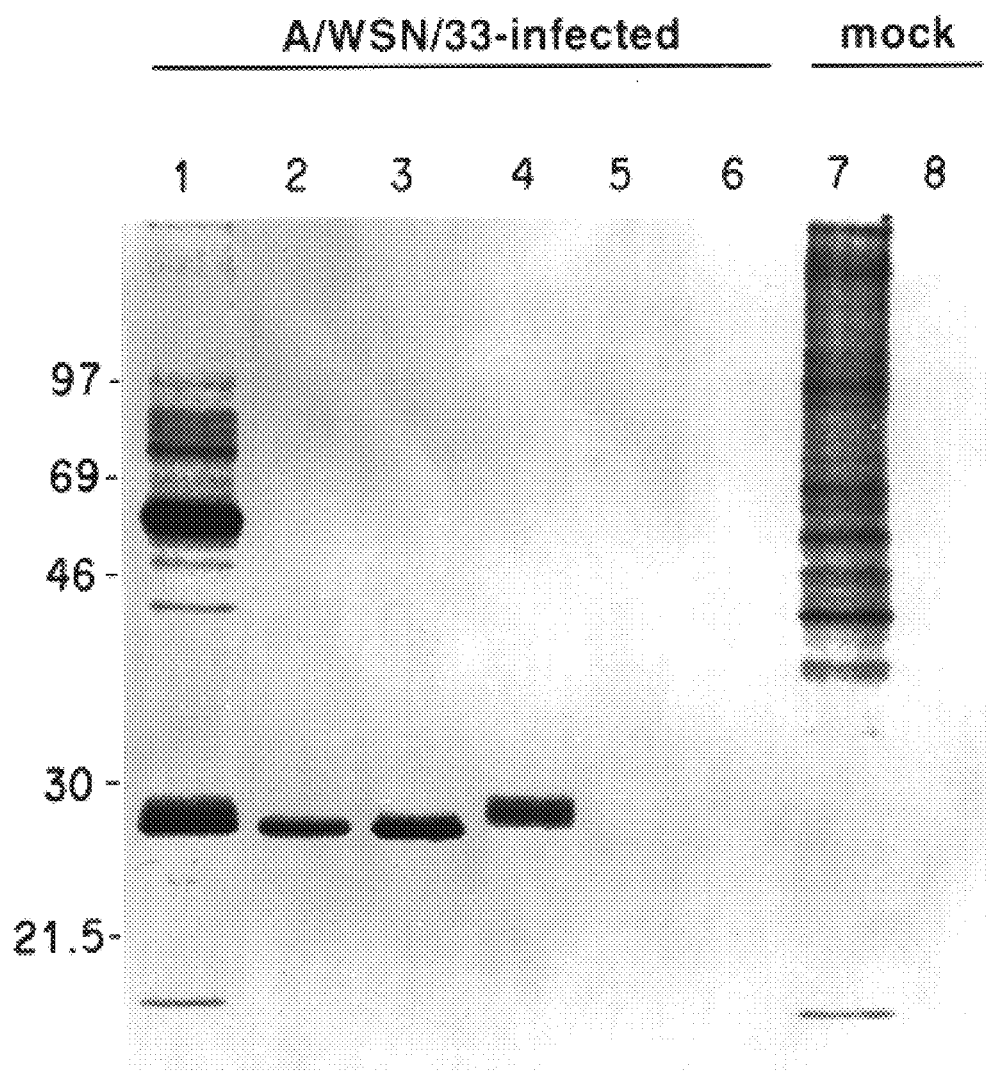

FIG. 14: Co-precipitation of NS1 protein from extracts of A/WSN/33-infected MDCK cells by GST-NS1I-1 and glutathione sepharose. Monolayers of MDCK cells were either infected with influenza A/WSN/33 virus at an m.o.i. of 10 or mock-infected, and labeled with $^{35}$S-methionine and cysteine from 5 to 6 hours p.i. Proteins were extracted and used for binding to glutathione sepharose coated with GST-NS1I-1 (lanes 3 and 8) or GST-protein (lane 6). As controls, extracts were immunoprecipitated with α-NS1 (lane 2), α-M1 (lane 4), or non-immune serum (lane 5). Proteins were analyzed by SDS gel electrophoresis and fluorography. Aliquots of the total extracts corresponding to 10 used for the glutathione agarose precipitations are shown (lanes 1 and 7). The positions of virus proteins and molecular weight markers are indicated to the left.

FIGS. 15A–15E: GST-NS1I-1 co-precipitates NS1 proteins of influenza A and B virus strains. Extracts of $^{35}$S-labeled MDCK cells infected with the influenza viruses A/duck/Alberta/76 (FIG. 15A), A/turkey/Oregon (FIG. 15B), A/Beijing/32/92 (FIG. 15C), A/Berkeley/1/68 (FIG. 15D), and B/Lee/40 (FIG. 15E) were prepared and used in precipitations of viral proteins by glutathione-sepharose coated with GST-NS1I-1 (lanes "GST-K5") or GST-protein (lanes "GST") as described in FIG. 14. In addition, viral proteins were immunoprecipitated using α-NS1-, α-M1- or non-immune serum (lanes "α-NS1", "α-M1", "NI", respectively). Analysis was by SDS gel electrophoresis and fluorography. Aliquots of the total extracts corresponding to 10 (FIGS. 15C and 15E) or 6.7 (FIGS. 15A, 15B, and 15D), respectively, are also shown (lanes "T"). The positions of viral proteins are indicated to the right.

FIGS. 16A–16C: Nucleotide sequence of NS1-BP cDNA (SEQ ID NO: 14) and derived amino acid sequence (SEQ ID NO: 15). The sequence of 2752 nucleotides was determined by sequencing of two overlapping clones. Nucleotides at positions +1038 to +2215 are derived from the HeLa cDNA-insert of the library plasmid p59-1. The 5'-end of the library cDNA is indicated by an arrow. Nucleotides −537 to +1037 were determined by sequencing cloned HeLa cDNA that was generated by 5'RACE. The open reading frame of 619 amino acids spans positions +1 to +1857. The deduced amino acid sequence is given in single letter codes. The stop codon is marked by an asterisk.

Figure 17:
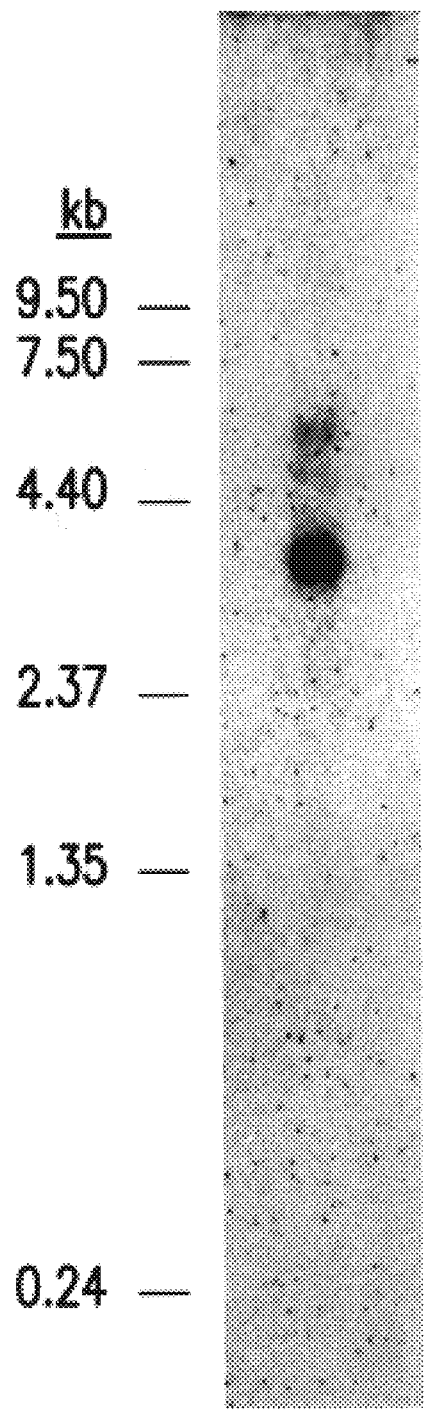

FIG. 17: Northern blot analysis of poly(A)-selected HeLa cell RNA with an NS1-BP-specific probe. 1 μg of HeLa cell poly(A)-RNA was separated by formaldehyde-agarose gel electrophoresis and immobilized on a nylon membrane. A $^{32}$P-labeled probe derived from p59-1 was used to detect NS1 -BP mRNA by hybridization. RNA size markers are indicated to the left.

FIG. 18: Alignment of the five tandem repeat elements of NS1-BP (SEQ ID NOS:16–20). The PILEUP program of the Genetics Computer Group (GCG) was used to align repetitive sequences between amino acids 368 and 607 of NS1-BP. The PRETTY program of GCG was used to determine a consensus sequence (SEQ ID NO:2 1). Conserved amino acids are shown in capital letters. Invariant positions are indicated by bold letters.

Figure 19:
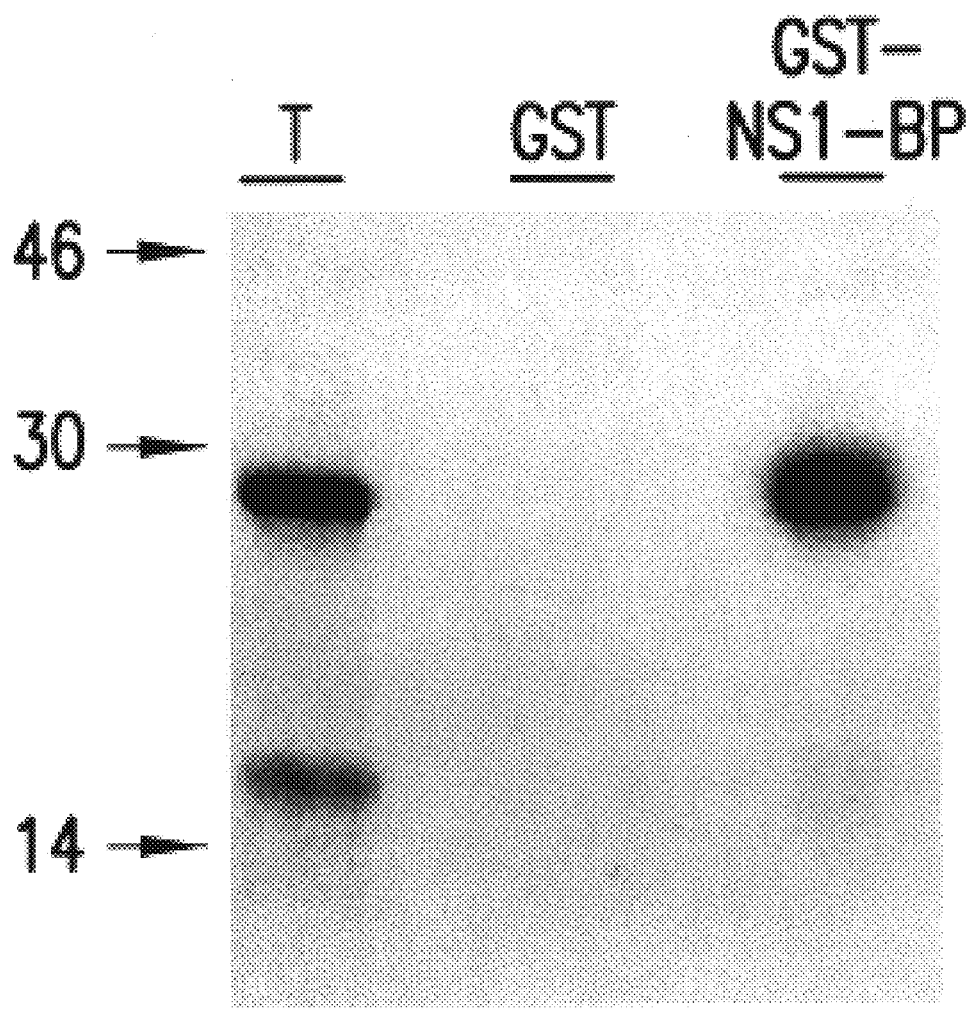

FIG. 19: Precipitation of $^{35}$S-labeled NS1 protein by GST-NS1 -BP fusion protein. Radiolabeled NS1 protein was synthesized in coupled transcription/translation reactions in the presence of $^{35}$S-methionine using pcDNA3-NS1 as a template. The NS1 protein was precipitated by glutathione Sepharose coated with GST (lane GST) or GST-NS1 -BP, which carries amino acids 347 to 619 of NS1-BP (lane GST-NS1-BP). The precipitates were analyzed by SDS polyacrylamide gel electrophoresis and autoradiography. A 10 aliquot of the total reaction was separated in parallel (T). The positions of molecular weight markers are indicated to the left.

Figure 20:
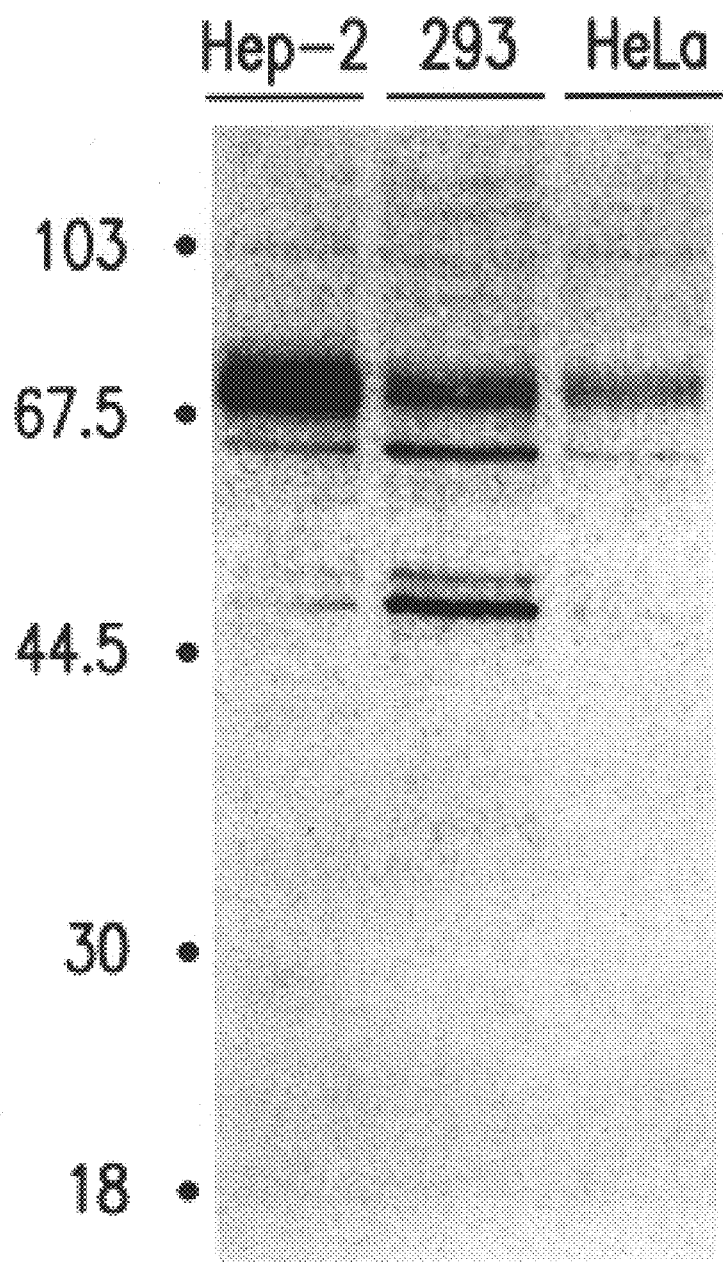

FIG. 20: Immunoblot analysis of NS1-BP. Confluent monolayers of Hep-2, 293 and HeLa cells were lysed in RIPA buffer. Soluble proteins from equivalent volumes of extract corresponding to $5\times10^4$ cells were separated by SDS gel electrophoresis, transferred to nitrocellulose membrane and probed with affinity-purified NS1-BP-specific antibodies. The positions of marker proteins are indicated to the left.

Figure 21:
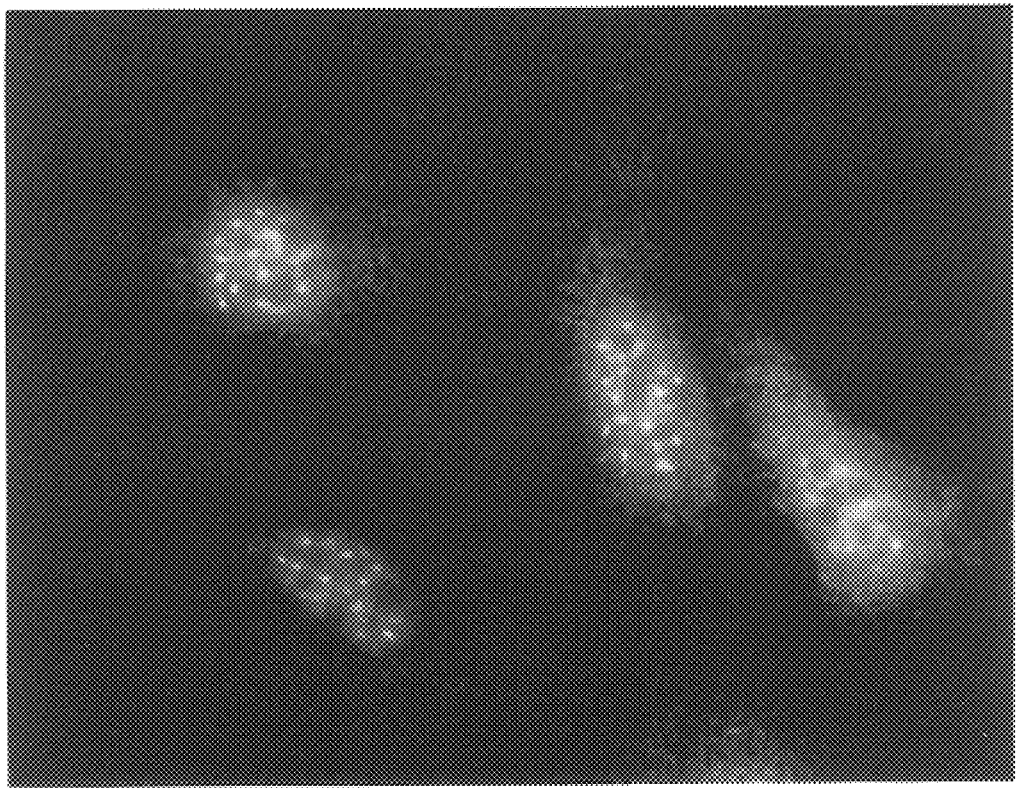

FIG. 21: Intracellular localization of NS1-BP as determined by indirect immunofluorescence analysis of HeLa cells. Subconfluent HeLa cells were fixed and stained with affinity-purified NS1-BP-specific rabbit antibodies followed by visualization using HTC-conjugated secondary antibodies.

Figure 22A:
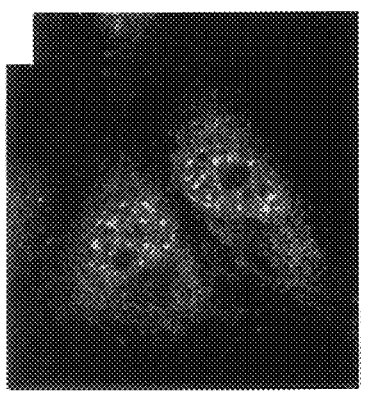
Figure 22B:
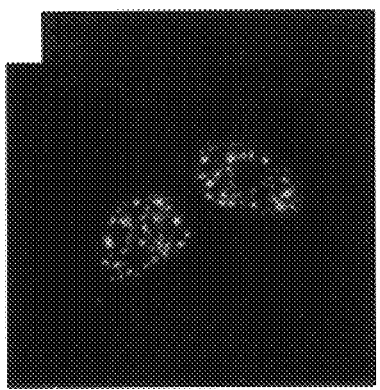
Figure 22C:
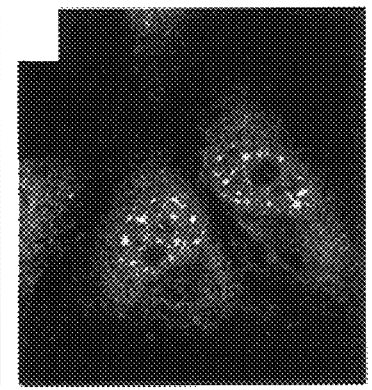
Figure 22D:
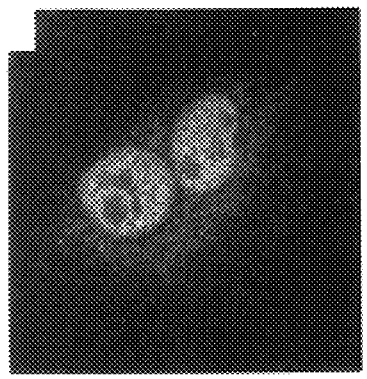
Figure 22E:
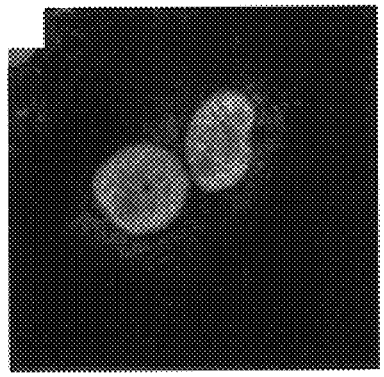
Figure 22F:
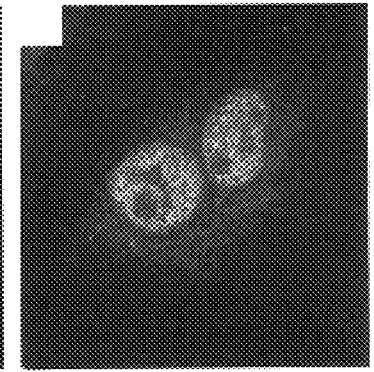
Figure 22G:
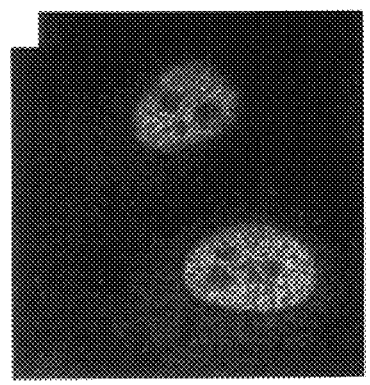
Figure 22H:
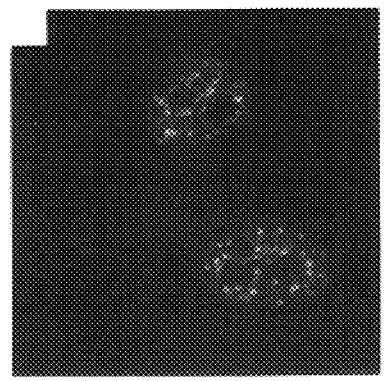
Figure 22I:
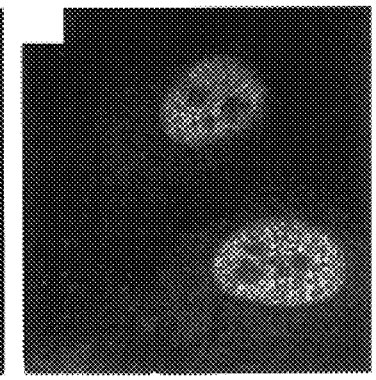

FIGS. 22A–22I: Intracellular distribution of the cellular NS1-BP, the SC35 protein and the viral NS1 protein in non-infected or influenza A virus infected HeLa cells. Confocal micrographs show non-infected (FIGS. 22A–22C) or influenza A/WSN/33 virus-infected HeLa cells at 10 hrs. p.i. (FIGS. 22D–22I). The intranuclear localization of NS1-BP was visualized by staining with NS1-BP-specific primary rabbit antibodies and FITC-conjugated secondary antibodies (FIGS. 22A, 22D, 22G). The cellular SC35 protein (FIGS. 22B and 22H) and the viral NS1 protein (FIG. 22E) were labeled by monoclonal mouse antibodies and visualized by Texas Red-conjugated anti-mouse IgG. Micrographs in the third column (FIGS. 22C, 22F and 22I) show confocal overlays of the FITC- and Texas Red-signals from the fields to the left.

Figures 23A, 23B:
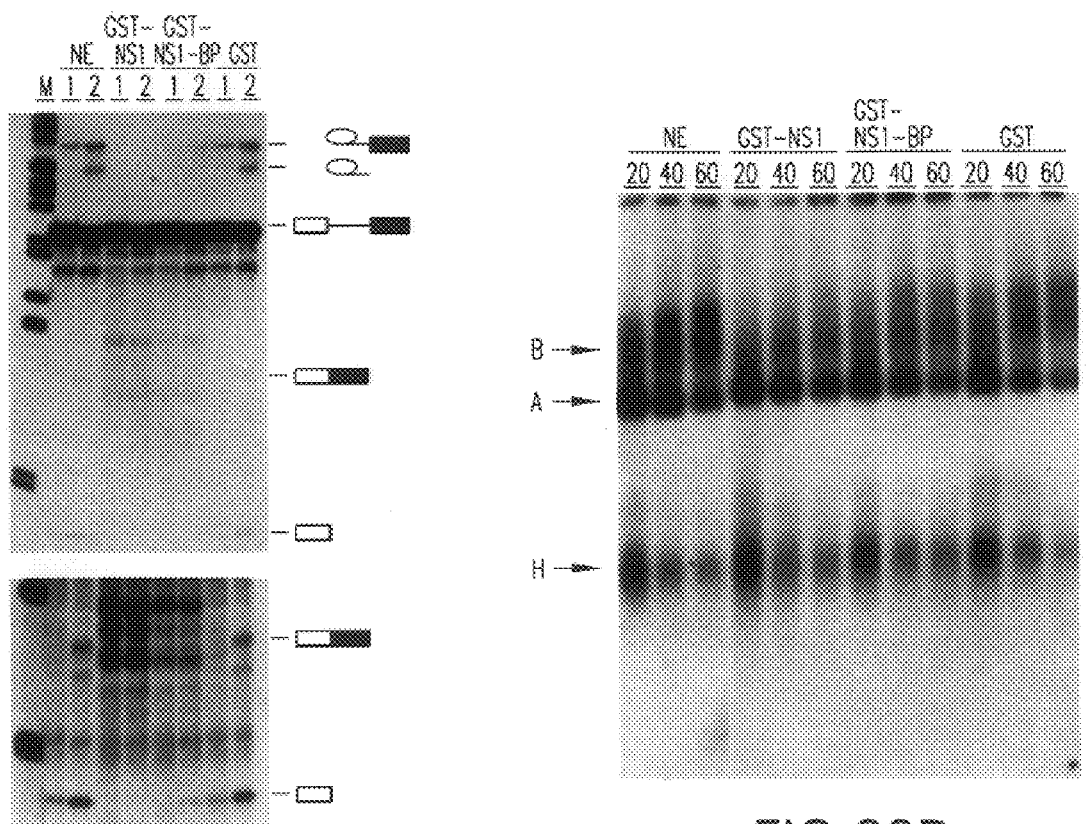

FIGS. 23A and 23B: Pre-mRNA splicing but not spliceosome assembly is inhibited by truncated NS1-BP. $^{32}$P-labeled MINX pre-mRNA was incubated in HeLa cell nuclear extract under splicing-compatible conditions in the absence (lanes NE) or presence of 80 ng/μl affinity-purified GST (lanes GST) or equimolar amounts of affinity purified GST-NS1 (lanes GST-NS1) or GST-NS1-BP fusion protein which carries amino acids 347 to 619 of NS1-BP (lanes GST-NS1-BP). (A) RNA analysis. RNA was purified from aliquots of the reactions after a one (lanes 1) or two hour incubation period (lanes 2) and analyzed by electrophoresis on denaturing 13 polyacrylamide-urea gels. The positions of the pre-mRNA, the intron-exon2 and exon1 intermediates, and the spliced mRNA and lariat products are indicated to the right. The lower part of the figure shows a longer exposure of the gel. M, $^{32}$P-labeled size marker DNA fragments. (B) Splicing complex analysis. Aliquots of the splicing reactions were taken after 20, 40 and 60 minutes and heparin was added to a final concentration of 1 mg/ml. The samples were analyzed by electrophoresis on a native agarose-polyacrylamide gel. The positions of the H-, A- and B-type splicing complexes (Konarska, M. M., et al., 1987. Cell 49: 763–774) are indicated on the left.

Figure 24A:
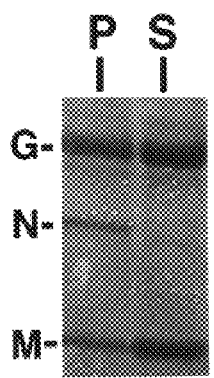
Figure 24B:
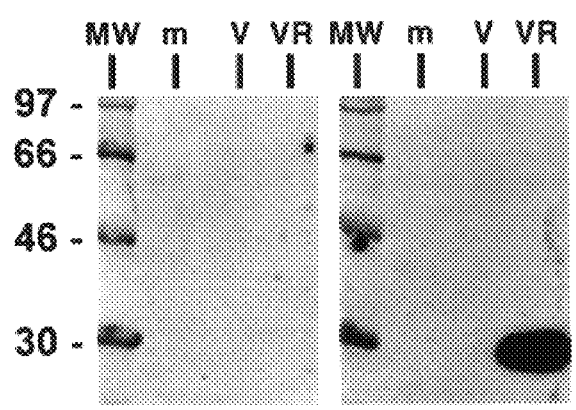
Figure 24C:
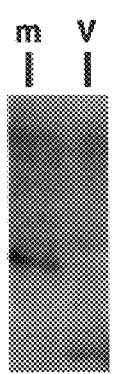

FIGS. 24A, 24B and 24C: Far-western analysis of VSV-infected cell extracts and VSV virions. A) Coomassie brilliant blue stain of VSV virion proteins (G=glycoprotein, N=nucleoprotein, and M=matrix protein) present within the pellet (P) and soluble (S) fractions. B) Identical nitrocellulose filters containing $^{14}$C-labeled protein standards (MW), mock-infected cell extracts (m), VSV (Ind.)-infected cell extracts (V), and the soluble fraction of purified VSV virions (VR). Filters were probed with either gst alone (left filter), or gstYAPWW1 (right filter). Cell extracts were prepared in RIPA buffer with 0.1 SDS. C) A longer exposure of lanes (m) and (V) from the right filter in FIG. 1B.

Figure 25:
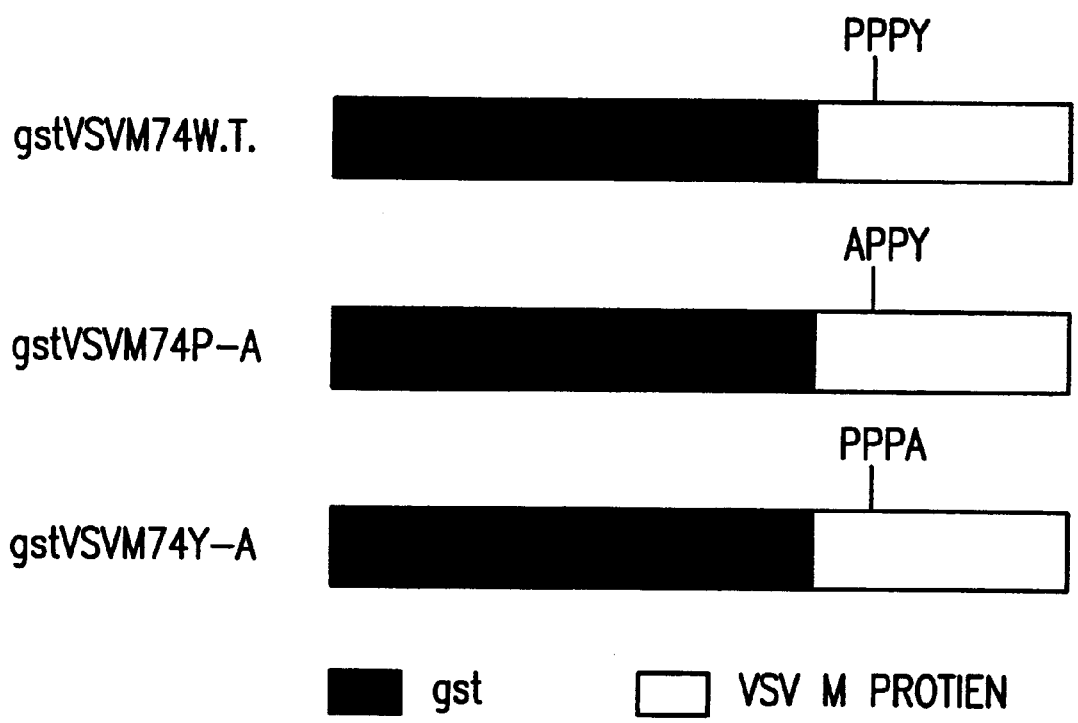

FIG. 25: Diagram of fusion proteins consisting of gst fused to the N-terminal 74 amino acids of VSV (Ind.) M protein. gstVSVM74WT contains a wild type PY motif. gstVSVM74P-A contains a single point mutation resulting in a proline (P) to alanine (A) change. gstVSVM74Y-A contains a single point mutation resulting in a tyrosine (Y) to alanine (A) change.

Figure 26A:
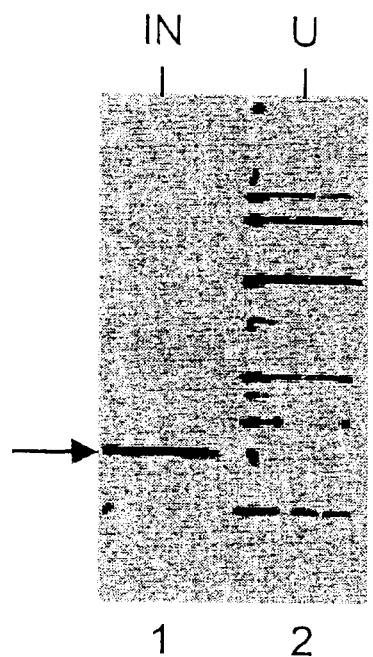
Figure 26B:
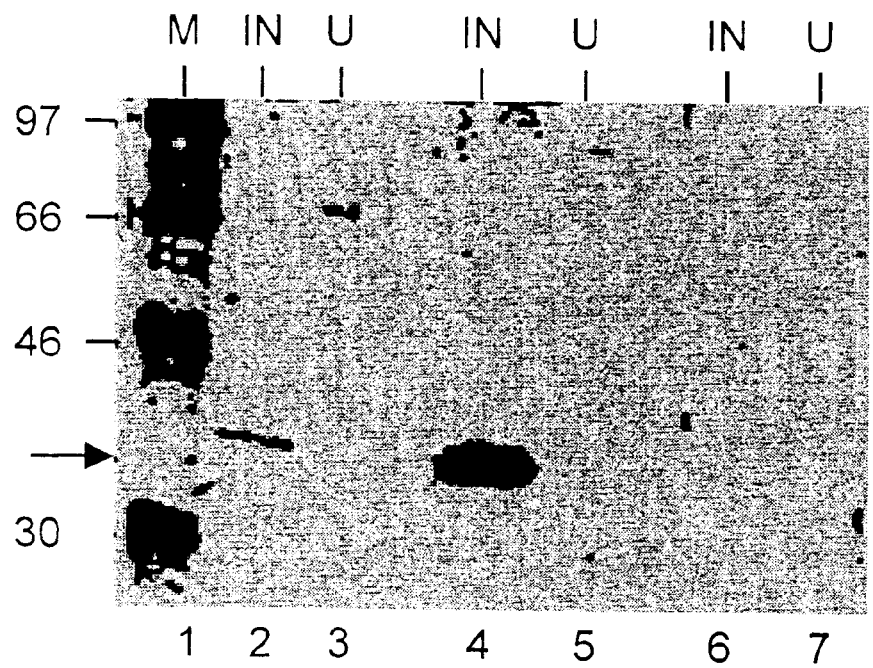

FIGS. 26A and 26B: Far-western analysis of gstVSVM74WT. A) Coomassie brilliant blue stain of bacterial cell extracts expressing gstVSVM74WT (indicated by the arrow) when grown under inducing (IN) conditions, and not expressing gstVSVM74WT when grown under noninducing (U) conditions. B) Three nitrocellulose filters containing the amount of protein seen in panel A, and probed withgstYAPWW2 (lanes 1, 2, and 3), gstYAPWW1 (lanes 4 and 5), and gst alone (lanes 6 and 7). M=$^{14}$C-labeled protein standards.

Figure 27A:
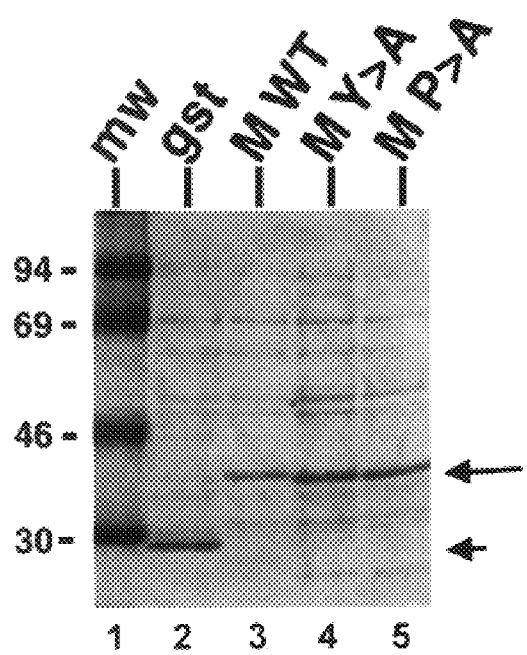
Figure 27B:
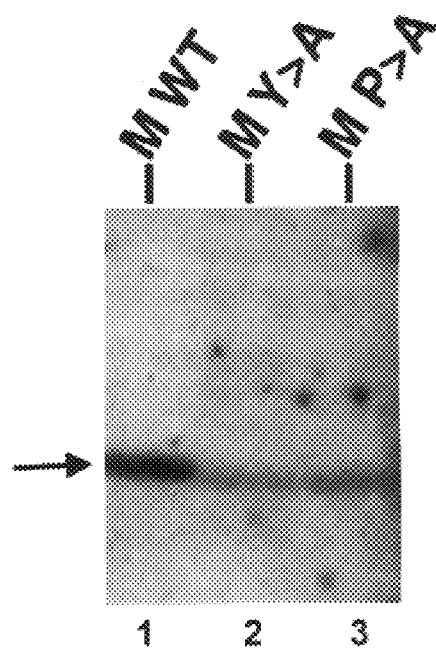

FIGS. 27A and 27B: Far-western analysis of wild type and mutant gst-VSVM fusion proteins. A) Coomassie brilliant blue stain of bacterial cell extracts expressing gst alone (lane 2, short arrow), gstVSVM74WT (lane 3), gstVSVM74Y-A (lane 4), and gstVSVM74P-A (lane 5). Lane 1 represents $^{14}$C-labeled protein standards (MW). The wild type fusion protein migrates slightly slower than the mutant proteins due to the presence of eight additional amino acids encoded by the polylinker region of this construct. B) Nitrocellulose filter containing identical amounts of protein as shown in panel A, and probed with gstYAPWW2. The intensity of the signals observed for gstVSVM74Y-A (lane 2) and gstVSVM74P-A (lane 3) is approximately 10 of that observed for gstVSVM74WT (lane 1).

Figure 28:
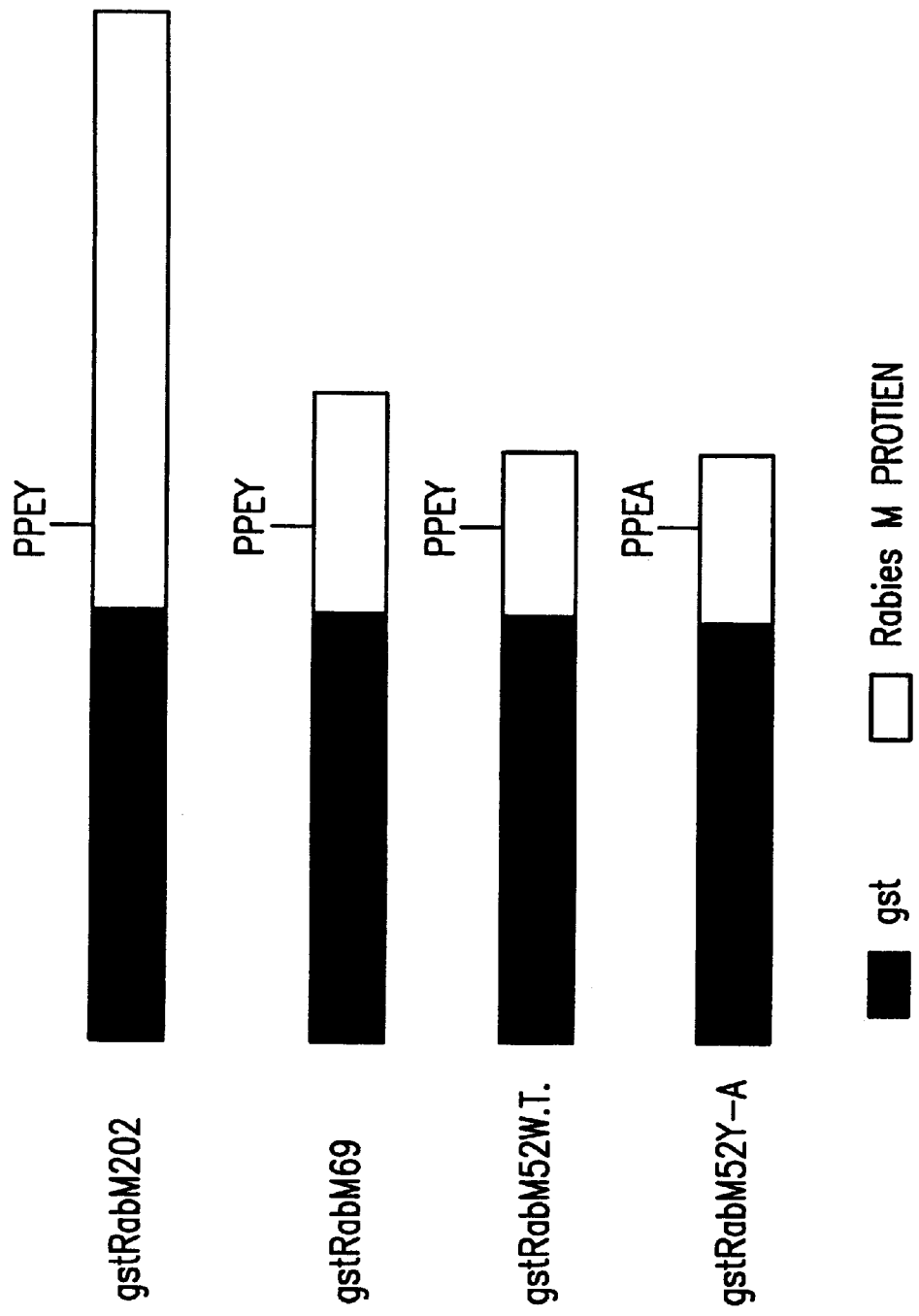

FIG. 28: Diagram of fusion proteins consisting of gst fused to amino acids 1–202 (full-length), 1–69, 1–52 (wild type), or 1–52 (Y-A; tyrosine to alanine mutation) of the rabies virus M protein. The designation of each of the fusion proteins is listed on the left. PPEY is the wild type sequence (E-glutamic acid).

FIGS. 29A, 29B and 29C: Far-western analysis of gst-rabies M fusion proteins. A) Duplicate nitrocellulose filters containing gstRabM69 (M1–69; lanes 1 and 3) and gstRabM202 (M202; lanes 2 and 4) were probed with either gst alone (lanes 1 and 2), or gstYAPWW2 (lanes 3 and 4). B) Coomassie brilliant blue stain of bacterial cell extracts expressing gstRabM52Y-A (Y-A; lane 1) or gstRabM52WT (WT; lane 2) indicated by the arrowhead. C) Identical amounts of gstRabM52Y-A and gstRabM52WT as seen in panel B were immobilized onto duplicate nitrocellulose filters and probed with either gst alone (lanes 1 and 2), or gstYAPWW2 (lanes 3 and 4).

Figure 30A:
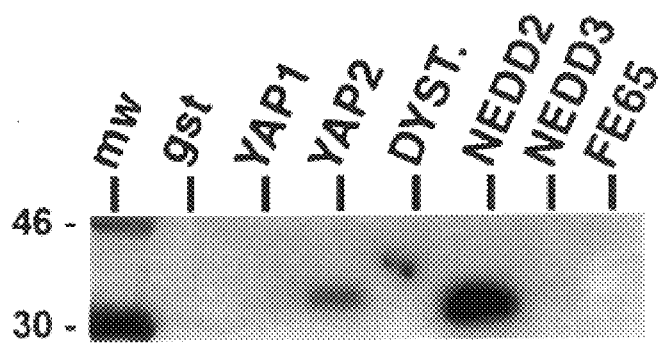
Figure 30B:
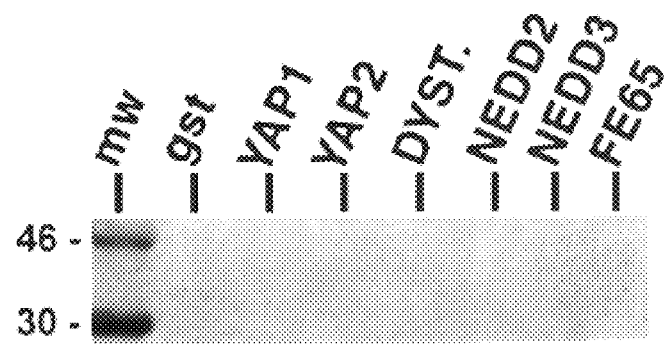
Figure 30C:
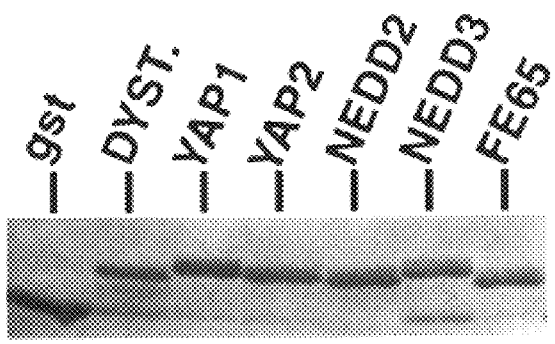

FIGS. 30A, 30B and 30C: Far-western analysis of gst-rabies M fusion proteins and a panel of gst-WW domain fusion proteins. Identical amounts of gst, gstYAPWW1 (YAP1), gstYAPWW2 (YAP2), gstDystrophinWW (DYST.), gstNEDD4WW2 (NEDD2), gstNEDD4WW3 (NEDD3) and gstFE65WW (FE65) were immobilized onto nitrocellulose and probed with either gstRabM52WT (Panel A), or gstRabM52Y-A (Panel B). MW=$^{14}$C-labeled protein standards. C) Coomassie brilliant blue stain of the gst-WW domain fusion proteins that were present on the filters in panels A and B.

Figure 31A:
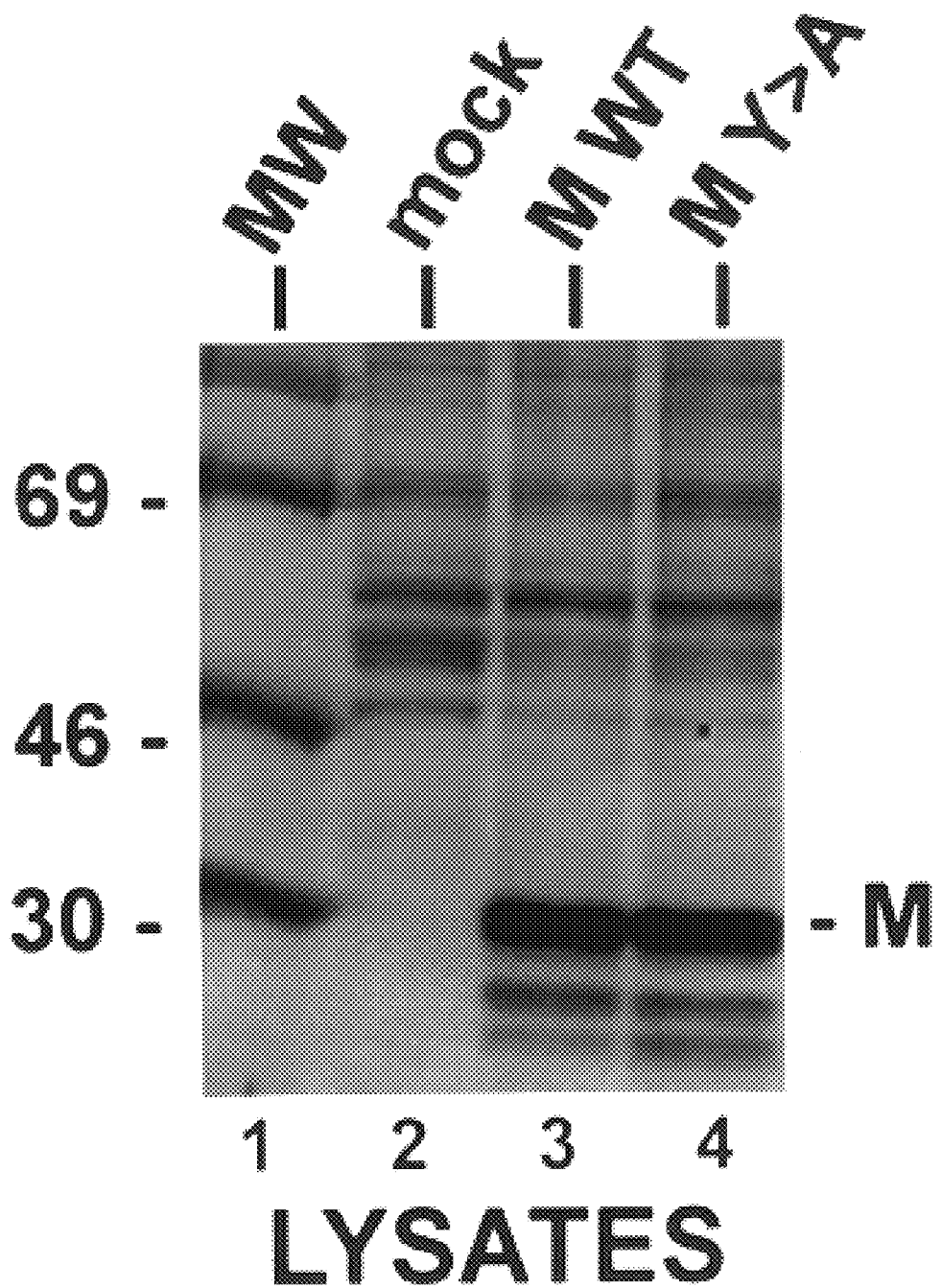

FIG. 31A: VSV M budding assay. Radiolabeled lysates from CV-1 cells receiving no DNA (mock, lane 2), T7VSVMWT DNA (MWT, lane 3), and T7VSVMY-A DNA (MY-A, lane 4) were immunoprecipitated with polyclonal antiserum against the M protein of VSV and fractioned by SDS-PAGE. The position of the M protein of VSV is indicated. MW=$^{14}$C-labeled protein standards.

Figure 31B:
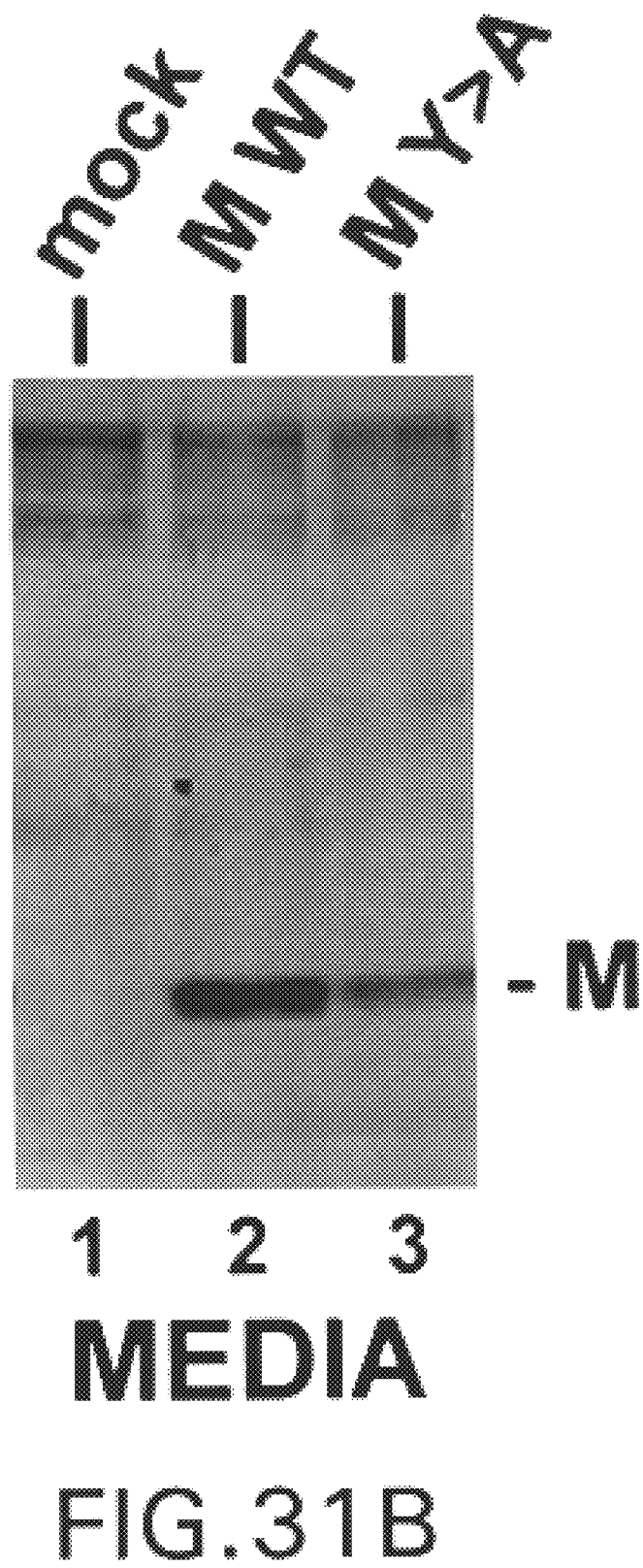

FIG. 31B: Radiolabeled proteins released into the media covering cells transfected with no DNA (mock, lane 1), T7VSVMWT DNA (lane 2), and T7VSVMY-A DNA (lane 3) were immunoprecipitated with polyclonal antiserum against the M protein of VSV and fractionated by SDS-PAGE. The relative migration of the M protein of VSV is indicated.

Figure 32A:
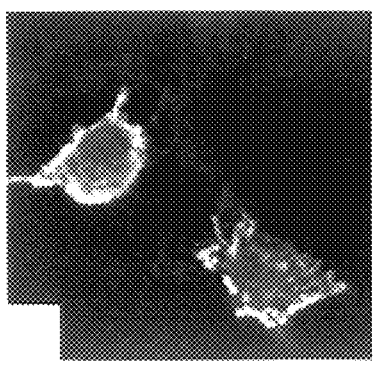
Figure 32B:
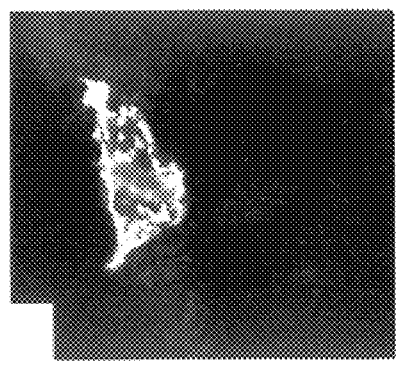
Figure 32C:
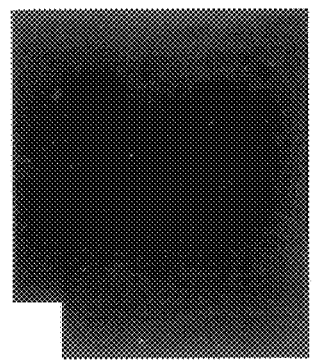

FIGS. 32A–32C: Indirect immunofluorescence and confocal microscopy of transfected CV-1 cells. A) CV-1 cells expressing wild type VSV M protein at 8 hours post-transfection. B) CV-1 cells expressing the VSV M protein containing a tyrosine (Y) to alanine (A) mutation within the PY motif at 8 hours post-transfection. C) untransfected CV-1 cells. Primary polyclonal antiserum (identical to that used in the experiment shown in FIG. 8) was directed against the M protein of VSV.

5. DETAILED DESCRIPTION OF THE INVENTION

The present invention relates to the identification of host cellular proteins that interact with viral proteins important to viral replication and infection; the identification of compounds that interfere with the specific interaction of the host cell and viral proteins; and the evaluation and use of such compounds as antivirals in the treatment of viral infections in animals, including humans.

The invention is described in this section and in the examples, below, for the identification and inhibition of interactions between human host cell proteins and viral proteins, including influenza virus and rhabdovirus proteins. For clarity of discussion, particular detail is provided for the isolation of five particular host cell proteins and/or protein domains. The first such host cell protein is nucleoprotein interactor 1 (NPI-1), a human cell protein that interacts with the influenza virus NP protein. The NPI-1 gene and protein, and the protein's interaction with NP protein are described in detail in the example in Section 6, below. Other host cell proteins that interact with the NP protein include, but are not limited to, NPI-2, NPI-3, NPI-4, NPI-5, and NPI-6, and are also described, below. The interactions between NP and the NPI-1 through NPI-6 host cell proteins provide novel targets for antiviral treatment and serve as excellent models for detailing the aspects of the invention. However, the principles may be analogously applied to the identification of other host cell proteins that interact with any of the four influenza virus proteins (PA, PB1, PB2, in addition to NP) required for viral RNA replication.

Particular detail is also provided in the examples in Sections 7 and 8, below, for the identification of human cell proteins that interact with the influenza virus NS1 protein. Section 7 describes the identification of nonstructural protein 1 interactor 1 (NS1I-1), a human cell protein that interacts with NS1. Section 8 describes the identification of nonstructural protein 1 binding protein (NS1-BP), a human cell protein that also interacts with NS1. These interactions provide novel targets for antiviral treatment.

As set forth in the example in Section 9, the present invention also contemplates identifying interactions between rhabdovirus proteins and host cell proteins. Section 9 describes the identification of cellular WW-domains as sites of interaction with the rhabdovirus matrix (M) protein. In a particular embodiment, the host cell protein is not a cell surface receptor protein.

The present invention further contemplates identifying interactions between host cell proteins and other viral proteins required for infection, including but not limited to, in the case of influenza virus, NEP, HA, NA, $M_1$, and $M_2$ proteins, or, in the case of rhabdoviruses, M protein, for example.

The principles may also be analogously applied to other RNA viruses both positive and negative stranded RNA viruses, both single and double stranded, including but not limited to single-stranded, positive-sense RNA viruses such as picornaviruses, caliciviruses, astroviruses, togaviruses, flaviviruses, coronaviruses, arteriviruses, and retroviruses; single-stranded, negative-sense RNA viruses such as paramyxoviruses (including parainfluenza viruses, measles virus, mumps virus, and respiratory syncytial virus), rhabdoviruses, filoviruses, orthomyxoviruses, orthomyxo-like viruses including Dhori insect virus, bunyaviruses, and arenaviruses; and double-stranded, positive-sense RNA viruses such as reoviruses and birnaviruses, as well as human immunodeficiency virus (HIV), members of the herpes virus family, and adenoviruses. The host cell proteins so identified may include completely novel proteins, or previously described proteins that have not yet been shown to interact with viral proteins.

Any method suitable for detecting protein-protein interactions may be employed for identifying novel viral-host protein interactions, and are considered within the scope of the present invention. For example, some traditional methods are co-immunoprecipitation, crosslinking and copurification through gradients or chromatographic columns. Newer methods result in the simultaneous identification of the genes coding for the protein interacting with a target protein. These methods include probing expression libraries with labeled target protein in a manner similar to antibody probing of λgt 11 libraries.

One such method that detects protein interactions in vivo, the yeast interactive trap system, was successfully used as described herein to identify the host cell proteins NPI-1 through NPI-6, NS1I-1, and NS1-BP described herein, and is described in detail for illustration only and not by way of limitation.

The host cell/viral protein interactions identified are considered targets for antiviral intervention. Assays, such as the ones described herein, can be used to identify compounds that interfere with such interactions. The compounds so identified that inhibit virus infection, replication, assembly, or release can be used as antivirals. In accordance with the invention, a given compound found to inhibit one virus may be tested for antiviral activity against a wide range of different viruses that have analogous dependencies on host cell proteins, including but not limited to single-stranded, positive-sense RNA viruses such as picornaviruses, caliciviruses, astroviruses, togaviruses, flaviviruses, coronaviruses, arteriviruses, and retroviruses; single-stranded negative-sense RNA viruses such as paramyxoviruses (including parainfluenza viruses, measles virus, mumps virus, and respiratory syncytial virus), rhabdoviruses, filoviruses, orthomyxoviruses, orthomyxo-like viruses including Dhori insect virus, bunyaviruses, and arenaviruses; and double-stranded, positive-sense RNA viruses such as reoviruses and birnaviruses, as well as human immunodeficiency virus (HIV), members of the herpes virus family, and adenoviruses.

Elucidation of the roles of the interacting proteins will lead to identifying other viruses as targets for intervention. For example, as described herein below, NPI-1 is important to the import of viral nucleic acid-protein complex into the nucleus of the host cell. Therefore, methods described below that disrupt this process, through interfering with the activity of NPI-1, for example, may be effective in treating viruses with nuclear phases. Such additional viruses include, but are not limited to, human immunodeficiency virus (HIV), members of the herpes virus family, and adenoviruses.

The various aspects of the invention are described in the subsections below with specific reference to host cell proteins that interact with the influenza viral proteins NP (host cell proteins NPI-1 through NPI-6) and NS1 (host cell proteins NS1I-1 and NS1-BP), and rhabdoviral M-protein (host cell proteins containing WW domains), with particular emphasis on host cell protein NPI-1; however, the invention is not limited to NPI-1 and encompasses any viral/host cell protein interactions as targets for therapeutic intervention.

5.1. IDENTIFICATION OF HOST CELL PROTEINS THAT INTERACT WITH VIRAL PROTEINS REQUIRED FOR REPLICATION

The gene for the host cell protein NPI-1 was cloned based on its ability to interact with the influenza A virus NP. The NPI-1 is the human homolog of the yeast protein SRP1. Interaction of NPI-1 and NP was demonstrated in yeast by the interactive trap system; in vitro coprecipitation of the NP with a bacterially expressed NPI-1 protein; and in infected cell extracts by coprecipitation of the NP with NPI-1, using anti-NPI-1 sera. The demonstration of this previously unknown interaction is illustrated in the working examples (see Section 6, infra). The data generated indicate that NPI-1 plays a role in the replication of influenza A viruses. NPI-1 is the first cellular protein characterized that interacts with a protein encoded by influenza viruses. This role, therefore, makes the inhibition of the NP-NPI-1 interaction an excellent target for antiviral therapy. It has not yet been demonstrated at what stage in the replication cycle NPI-1 functions. The NPI-1 could affect any of a number of NP functions which may include: (1) movement of the ribonucleoprotein complex (RNP) to the nucleus; (2) vRNA synthesis, including antiterrnination and elongation; (3) mRNA synthesis, including elongation, polyadenylation, and transport to the cytoplasm; and (4) exit of the RNP from the nucleus during virion assembly.

The fact that both NPI-1 and SRP1 interact with proteins involved in RNA synthesis implies that there may be fundamental similarities between cellular DNA-dependent transcription and influenza viral RNA-dependent RNA synthesis. Cellular factors, like NPI-1, may be shared by the viral and the cellular RNA synthesis machinery to perform similar functions. In addition, the NPI-1 may tether the viral RNP to areas of the nuclear matrix where splicing and polyadenylation of MRNA occur. It should be noted that although NPI-1 was isolated from HeLa cells, this cell line is not productively infected by influenza A virus. However, HeLa cells synthesize influenza viral RNAs and proteins (see FIG. 6, lane 3), and have previously been used to examine viral RNA synthesis (Beaton & Krug, 1986, Proc. Natl. Acad. Sci. USA 83:6282–6286).

The viral NP exists in two forms in the infected cell. One form is associated with ribonucleoprotein complexes (RNP), and the other is a free form (Shapiro & Krug, 1988, J. Virol. 62: 2285–2290). Pol/NP preparations used in coprecipitation experiments with NPI-1 were purified over cesium chloride/glycerol gradients (Honda, et al., 1988, J. Biochem. 104: 1021–1026), which dissociate and purify virion proteins away from vRNA. As shown herein, (FIG. 4, lane 3) the NP but not the polymerase proteins were detected oil Coomassie stained gels; however, coprecipitation of the viral polymerase proteins was not rigorously tested by immunoblot experiments. Only the NP was coprecipitated from infected HeLa cell extracts (FIG. 6) suggesting that it is free NP that is bound by NPI-1.

Only one host factor has been assigned a definitive function in the replication process of a negative strand RNA virus. The cellular casein kinase II has been shown to phosphorylate the phosphoprotein P of the vesicular stomatitis-virus (VSV) RNA-dependent RNA polymerase. This is a step that appears to be required-in order to activate the viral polymerase (Barik and Banerjee, 1992, Proc. Natl. Acad. Sci. USA 89: 6570–6574; Barik and Banerjee, 1992, J. Virol. 66: 1109–1118).

NPI-1 and SRP 1 are 50% identical and 81% conserved at the amino acid level. This is as a very high degree of conservation between proteins belonging to organisms as distantly related as humans and yeast, and suggests that the NPI-1/SRP1 performs a very basic function in the cell. NPI-1 and SRP1 have eight internal repeats, each of approximately 42-amino acids (FIG. 3). This repeat, termed the ARM motif, was originally identified in the Drosophila segment polarity gene armadillo (Riggleman, et al., 1989, Genes Dev. 3: 96–113), and it has been identified in a number of other proteins including β-catenin, plakoglobin, p120, APC and smGDS (Peifer, et al., 1994, Cell 76: 789–791, and references therein). Several ARM proteins are associated with cell adhesion structures. Armadillo and its homologues bind to the C-terminal cytoplasmic tail of cadherins, a calcium-dependent class of cell adhesion molecules (CAMs), linking the CAMs to the underlying cytoskeleton at cell-cell junctions (McCrea, et al., 1991, Science 254: 1359–1361). In contrast to the armadillo protein, SRP1 and NPI-1 appear to be localized to the nucleus. If NPI-1, like SRP1 (Yano, et al., 1992, Mol. Cell. Biol. 12: 5640–5651), is associated with the nuclear membrane, it is possible that NPI-1 functions to tether viral RNP to the nuclear membranes (Jackson, et al., 1982, Nature 296: 366–368). It should be noted that NPI-1 may be related to (or identical with) a nuclear protein that has been found to be involved in V(D)J ecombination (Cuomo, et al., 1994, Meeting abstract F015, Keystone Symposium on Recombination).

The carboxyl terminal 265 amino acids of the NPI-1, which were sufficient for interaction with the viral NP, contain four and one-half ARM repeats. Individual repeats, in general, are approximately 30 identical with the ARM consensus sequence. This is consistent with the degree of conservation in ARM repeats of other proteins (Peifer, et al., 1994, Cell 76: 789–791).

Using the same interactive trap system in yeast, five additional DNA sequences, NPI-2, NPI-3, NPI-4, NPI-5, and NPI-6 were isolated that partially encode proteins that interact with the NP of influenza A virus.

Also, using the yeast interactive trap system, DNA sequences encoding the NS1I-1 protein and the NS1-BP were identified based on the interaction between these proteins and the NS1 protein of influenza A virus. NS1I-1 protein is the human homolog of porcine 17β-estradiol dehydrogenase. Several proteins with a dehydrogenase function have recently been shown to be involved in post-transcriptional events of gene expression (Hentze, 1994, Trends Biochem. Sci. 19: 101–103). This supports an important functional role for the NS1I-1 interaction during the viral life cycle.

Using oligonucleotide primers and standard PCR protocols to introduce point mutations within selected protein motifs of the rhabdovirus M protein, followed by a budding assay, host cellular proteins containing WW domains that interact with viral M protein were identified (see Section 9).

The various proteins so identified are listed in Table I.

TABLE I

INTERACTING HOST CELL PROTEINS

| Host Cell Proteins | FIG. # | Comments |
|---|---|---|
| NPI-1 | FIG. 2 | Protein sequence, homologous to SRPI of yeast |
| NPI-2 | FIG. 7 | Identical to sequences of hnRNP C proteins (Lahiri and Thomas, 1986, Nucl. Acids Res. 14: 4077-4094) |
| NPI-3 | FIG. 8 | |
| NPI-4 | FIG. 9 | |
| NPI-5 | FIG. 10 | |
| NPI-6 | FIG. 11 | |
| NS1I-1 | FIG. 12. | Protein sequence, homologous to porcine 17β-estradiol dehydrogenase |
| NS1-BP WW domains | FIG. 16 | (See Section 8) |

Note:
Subsequent to Applicants' identification of NPI-3, NPI-4, and NPI-5, these sequences were described by other groups and designated Rch1, PC4, and BAT1, respectively.

The coding sequence for NPI-2 is identical to sequences coding for the previously identified hnRNP C proteins (Lahiri and Thomas, 1986, Nucl. Acids Res. 14: 4077–4094). The NPI-3, NPI-4, NPI-5, and NPI-6 coding sequences were unknown prior to their identification by Applicant. The coding sequences for NS1I-1 and NS1-BP are described in detail in the example in Sections 7 and 8, below. The WW domain was previously characterized by Sudol, 1996, In Blundell, et al., (eds.), *Prog. Biophys. Molec. Biol.*, Vol. 65, Elsevier Science Ltd., Great Britain, pp. 113–132, as detailed in Section 9, below.

The specific binding domains of the viral and host cell protein binding partners can be used in accordance with the invention as targets for therapeutic intervention or screening assays to identify inhibitory compounds. In addition, peptides corresponding to the binding site of the viral or host cell protein can be used as antiviral inhibitors by disrupting the binding between the binding partners. For example, peptides having amino acid sequences within the viral NP-NLS domain can be used to disrupt the interaction between NP and NPI-1, and thereby inhibit viral replication, as detailed in the Example in Section 10, below.

In one embodiment, such an inhibitory peptide comprises a 19 amino-acid sequence of an NP-NLS oligopeptide (Ala Ser Gln Gly Thr Lys Arg Ser Tyr Glu Gln Met Glu Thr Asp Gly Glu Arg Gln (SEQ ID NO:22); corresponding to amino acids 2–20 of NP). In another embodiment, the protein of the invention comprises amino acids 1–20 of NP. In another embodiment, the protein of the invention comprises a subsequence from 8–18 amino acids in length of the Ala Ser Gln Gly Thr Lys Arg Ser Tyr Glu Gln Met Glu Thr Asp Gly Glu Arg Gln (SEQ ID NO:22) 19-mer of the NP-NLS oligopeptide. Preferably, the protein of the invention comprises an 8 amino-acid sequence Thr Lys Arg Ser Xaa Xaa Xaa Met (SEQ ID NO:23), which corresponds to the conserved domain of an NP-NLS peptide. The invention contemplates a protein comprising the Ala Ser Gln Gly Thr Lys Arg Ser Tyr Glu Gln Met Glu Thr Asp Gly Glu Arg Gln (SEQ ID NO:22) 19-mer of the NP-NLS oligopeptide, or an 8–18 amino acid subsequence thereof, in which one or more of the following amino acids substitutions are made at the following positions:

Position 2: Ser→Thr
Position 3: Gln→Lys
Position 8: Ser→Pro
Position 10: Glu→Gly
Position 15: Asp→Gly
Position 17: Glu→Asp.

The invention also contemplates a protein of the invention comprising a subsequence of the Ala Ser Gln Gly Thr Lys Arg Ser Tyr Glu Gln Met Glu Thr Asp Gly Glu Arg Gln (SEQ ID NO:22) 19-mer of the NP-NLS oligopeptide in which position 19 (amino acid Gln) is deleted.

The invention contemplates, in addition to the DNA sequences disclosed herein, 1) any DNA sequence that encodes the same amino acid sequence as encoded by the DNA sequences shown in FIGS. 2, 7–12 and 16 any DNA sequence that hybridizes to the complement of the coding sequences disclosed herein (see FIGS. 2, 7–12, and 16) under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1 SDS at 68° C. (Ausubel, F. M., et al., eds., 1989, Current Protocols in Molecular Biology, Vol. 1, Green Publishing Associates, Inc., and John Wiley and Sons, Inc., New York, at p. 2.10.3) and encodes a finctionally equivalent gene product; and/or 3) any DNA sequence that hybridizes to the complement of the coding sequences disclosed herein (see FIGS. 2, 7–12, and 16) under less stringent conditions, such as moderately stringent conditions, e.g., washing in 0.2×SSC/0.1 SDS at 42° C. (Ausubel, F. M., et al., eds., 1989, Current Protocols in Molecular Biology, Vol. I, Green Publishing Associates, Inc., and John Wiley and Sons, Inc., New York, at p. 2.10.3), yet that still encodes a functionally equivalent gene product.

The invention also encompasses 1) DNA vectors that contain any of the coding sequences disclosed herein (see FIGS. 2, 7–12, and 16), and/or their complements (i.e., antisense); 2) DNA expression vectors that contain any of the coding sequences disclosed herein (see FIGS. 2, 7–12, and 16), and/or their complements (i.e., antisense), operatively associated with a regulatory element that directs the expression of the coding and/or antisense sequences; and 3) genetically engineered host cells that contain any of the coding sequences disclosed herein (see FIGS. 2, 7–12, and 16), and/or, their complements (ie., antisense), operatively associated with a regulatory element that directs the expression of the coding and/or antisense sequences in the host cell. Regulatory elements include but are not limited to inducible and non-inducible promoters, enhancers, operators and other elements known to those skilled in the art that drive and regulate expression. The invention includes fragments of any of the DNA sequences disclosed herein.

Once the host cell proteins are obtained, they can be used to detect interactions with proteins from other viruses, in accordance with the invention. The following descriptions are provided to illustrate this approach and not by way of limitation. Influenza B virus ribonucleoprotein complex was isolated and using a Western immunoblot assay, it was found that the cellular NPI-1 was associated with this complex. This result indicates that NPI-1, isolated based on its interaction with influenza A virus NP, also interacts with influenza B virus NP. Thus, compounds that inhibit NP-NPI-1 interactions in influenza A virus and thereby inhibit influenza A viral infection should be similarly effective as antivirals against influenza B virus.

Host cell genes that are homologous to those identified herein may be obtained by several methods. In some cases, different host cell proteins that share the property of interacting with the same viral protein, e.g. influenza A virus NP, may also share genetic homology. Thus, the genes identified through the interactive trap selection may be homologous to one another.

Once a host cell gene is identified in accordance with the invention, any homologous gene may be obtained using cloning methods well known to those skilled in the art, including but not limited to the use of appropriate probes to detect the homologous genes within an appropriate cDNA or gDNA (genomic DNA) library. (See, for example, Sambrook, et al., 1989, Molecular Cloning: A Laboratory Manual, Cold Spring Harbor Laboratories, which is incorporated by reference herein in its entirety.) This method is especially useful for obtaining proteins that may not share the property of binding to the same viral protein, but may nonetheless be genetically homologous.

Such homologous proteins may interact with proteins of viruses other than the virus used in the interactive trap. For example, a host cell gene whose product was detected through its interaction with an influenza A viral protein may be homologous to another gene whose product does not interact with influenza A virus, but which does interact with influenza B viral protein. To optimize the detection of such a homologous gene, cDNA libraries may be constructed from cells infected with a virus of interest. Besides influenza B virus, this procedure may be applied analogously to other viruses as well, including but not limited to single-stranded, positive-sense RNA viruses such as picornaviruses, caliciviruses, astroviruses, togaviruses,: flaviviruses, coronaviruses, arteriviruses, and retroviruses; single-stranded, negative-sense RNA viruses such as paramyxoviruses (including parainfluenza viruses, measles virus, mumps virus, and respiratory syncytial virus), rhabdoviruses, filoviruses, orthomyxoviruses, orthomyxo-like viruses including Dhori insect virus, bunyaviruses, and arenaviruses; and double-stranded, positive-sense RNA viruses such as reoviruses and birnaviruses, as well as human immunodeficiency virus (HIV), members of the herpes virus family, and adenoviruses.

5.2. SCREENING ASSAYS FOR COMPOUNDS THAT INTERFERE WITH THE INTERACTION OF HOST CELL AND VIRAL PROTEINS REQUIRED FOR VIRAL REPLICATION

The host cell protein and the viral protein that interact and bind are sometimes referred to herein as "binding partners".This term also includes peptide fragments, produced as described in the subsections below, comprising the binding domain of each respective protein. Any of a number of assay systems may be utilized. to test compounds for their ability to interfere with the interaction of the binding partners. However, rapid high throughput assays for screening large numbers of compounds, including but not limited to ligands (natural or synthetic), peptides, or small organic molecules are preferred. Compounds that are so identified to interfere with the interaction of the binding partners should be further evaluated for antiviral activity in cell based assays, animal model systems and in patients as described herein.

The basic principle of the assay systems used to identify compounds that interfere with the interaction between the viral and host cell proteins involves preparing a reaction mixture containing the viral protein and the host cell protein under conditions and for a time sufficient to allow the two proteins to interact and bind, thus forming a complex. In order to test a compound for inhibitory activity, the reaction is conducted in the presence and absence of the test compound, i.e., the test compound may be initially included in the reaction mixture, or added at a time subsequent to the addition of the viral and host cell protein; controls are incubated without the test compound or with a placebo. The formation of any complexes between the viral protein and the host cell protein is then detected. The formation of a complex in the control reaction, but not in the reaction mixture containing the test compound indicates that the compound interferes with the interaction of the viral protein and host cell protein.

The following two descriptions of assay systems used to identify compounds that interfere with the interaction between the viral and host cell proteins are given by way of illustration and not by way of limitation. In a first illustration, NP-NLS oligopeptide consisting of amino acids 2–10 of the NLS peptide was used to inhibit viral growth a thousand-fold in cultured MDBK cells. Thus, peptides that correspond to the NP-NLS target site of binding with NPI-1 can inhibit the interaction of NP with NPI-1 and can be used to treat influenza infection. In a second illustration, NP-NLS was found to bind NPI-1 at a domain of NPI-1 corresponding to amino acids 425–538 of NPI-1. These two illustrations demonstrate that each peptide binding partner (NP, NPI-1, NPI-2) or fragment thereof can be used for screening for compounds that interact with a binding domain and thereby interfere with or disrupt the binding interaction of NP with NPI-1 and/or NPI-3. Each peptide binding partner (NP, NPI-1, NPI-2) or fragment thereof can also be used directly to competitively interfere with or disrupt the binding interaction of NP with NPI-1 and/or NPI-3 and therefore, to treat influenza infection.

In one embodiment, an NP-NLS peptide is used to disrupt the binding interaction of NP with NPI-1 and/or NPI-3. Preferably an amino acid sequence ranging from 8–20 amino acids of the N-terminus of NP is used. Alternatively a 19-mer amino acid sequence (Ala Ser Gln Gly Thr Lys Arg Ser Tyr Glu Gln Met Glu Thr Asp Gly Glu Arg Gln (SEQ ID NO:22)) corresponding to amino acids 2–20 of the NP protein is used. In one embodiment, the peptide used to disrupt the binding interaction of NP with NPI-1 and/or NPI-1 comprises a 19 amino-acid sequence of an NP-NLS oligopeptide (Ala Ser Gin Gly Thr Lys Arg Ser Tyr Glu Gln Met Glu Thr Asp Gly Glu Arg Gln (SEQ ID NO:22); corresponding to amino acids 2–20 of NP). In another embodiment, the peptide used to disrupt the binding interaction comprises amino acids 1–20 of NP. In another embodiment, the peptide used to disrupt the binding interaction comprises a subsequence from 8–18 amino acids long of the Ala Ser Gln Gly Thr Lys Arg Ser Tyr Glu Gln Met Glu Thr Asp Gly Glu Arg Gln (SEQ ID NO:22) 19-mer of the NP-NLS oligopeptide. Preferably, the peptide used to disrupt the binding interaction comprises an 8 amino-acid sequence Thr Lys Arg Ser Xaa Xaa Xaa Met (SEQ ID NO:23), which corresponds to the conserved domain of an NP-NLS peptide. The invention contemplates a peptide that is used to disrupt the binding interaction comprising the Ala Ser Gln Gly Thr Lys Arg Ser Tyr Glu Gln Met Glu Thr Asp Gly Glu Arg Gln (SEQ ID NO:22) 19-mer of the NP-NLS oligopeptide, or an 8–18 amino acid subsequence thereof, in which one or more of the following amino acids substitutions are made at the following positions:

Position 2: Ser→Thr
Position 3: Gln→Lys
Position 8: Ser→Pro
Position 10: Glu→Gly
Position 15: Asp→Gly
Position 17: Glu→Asp.

The invention also contemplates a peptide that is used to disrupt the binding interaction comprising a subsequence of the Ala Ser Gln Gly Thr Lys Arg Ser Tyr Glu Gln Met Glu Thr Asp Gly Glu Arg Gln 19-mer of the NP-NLS oligopeptide in which position 19 (amino acid Gln) is deleted.

The assay components and various formats that may be utilized are described in the subsections below.

5.2.1. ASSAY COMPONENTS
5.2.1.1. PEPTIDES

The host cell protein and viral protein binding partners used as components in the assay may be derived from natural sources, e.g., purified from cells and virus, respectively, using protein separation techniques well known in the art; produced by recombinant DNA technology using techniques known in the art (see e.g., Sambrook, et al., 1989, Molecular Cloning: A Laboratory Manual, Cold Spring Harbor Laboratories Press, Cold Spring Harbor, N.Y.); and/or chemically synthesized in whole or in part using techniques known in the art; e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50–60). The composition of the synthetic peptides may be confirmed by amino acid analysis or sequencing; e.g., using the Edman degradation procedure (see e.g., Creighton, 1983, Proteins: Structures and Molecular Principles, W.H. Freeman & Co., N.Y., pp. 34–49).

The peptide fragments should be produced to correspond to the binding domains of the respective proteins. Any number of methods routinely practiced in the art can be used to identify and isolate the protein's binding site. These methods include but are not limited to mutagenesis of one of the genes encoding the protein and screening for disruption of binding in a co-immunoprecipitation assay, or mutagenesis of the host cell gene and selecting for resistance to viral infection. Compensating mutations in the viral gene can be selected that allow for viral grovth in this mutant host. Sequence analysis of the genes encoding the respective proteins will reveal the mutations that correspond to the region of the protein involved in interactive binding. Alternatively, one protein can be anchored to a solid surface using methods described in section 5.2.2. infra, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene for the protein is obtained, short gene segments can be engineered to express peptide fragments of the protein, which can then be tested for binding activity and purified or synthesized.

Whether produced by molecular cloning methods or by chemical synthetic methods, the amino acid sequence of the binding partners which may be used in the assays of the invention need not be identical to the reported sequence of the genes encoding them. The binding partners may comprise altered sequences in which amino acid residues are deleted, added, or substituted resulting in a functionally equivalent product.

For example, functionally equivalent amino acid residues may be substituted for residues within the sequence resulting in a change of sequence. Such substitutes may be selected from other members of the class to which the amino acid belongs; e.g., the nonpolar (hydrophobic) amino acids include alanine, leucine, isoleucine, valine, proline, phenylalanine, tryptophan, and methionine; the polar neutral amino acids include glycine, serine, threonine, cysteine, tyrosine, asparagine, and glutamine; the positively charged (basic) amino acids include arginine, lysine, and histidine; the negatively charged (acidic) amino acids include aspartic and glutamic acid.

One of the binding partners used in the assay system should be labeled, either directly or indirectly, to facilitate detection of a complex formed between the viral and host cell proteins. Any of a variety of suitable labeling systems may be used including but not limited to radioisotopes such as $^{125}I$, $^{131}I$, $^{35}S$ or $^{3}H$; enzyme labeling systems that generate a detectable colorimetric signal or light when exposed to substrate such as horseradish peroxidase, alkaline phosphatase, beta-galactosidase, and luciferase; and fluorescent labels such as umbelliferone, fluorescein, fluorescein isothiocyanate, rhodamine, dichlorotriazinylamine fluorescein, dansyl chloride and phycoerythrin.

5.2.1.2. LABELING, IMMOBILIZATION AND DETECTION OF PEPTIDES AND PROTEINS

Where recombinant DNA technology is used to produce the viral and host cell binding partners of the assay it may be advantageous to engineer fusion proteins that can facilitate labeling, immobilization and/or detection. For example, the coding sequence of the viral or host cell protein can be fused to that of a heterologous protein that has enzyme activity or serves as an enzyme substrate in order to facilitate labeling and detection. The fusion constructs should be designed so that the heterologous component of the fusion product does not interfere with binding of the host cell and viral protein.

5.2.1.3. LABELING WITH ANTIBODIES

Indirect labeling involves the use of a third protein, such as a labeled antibody, which specifically binds to one of the binding partners, ie., either the host cell protein or viral protein used. The term "antibody" or "antibodies" as used herein refers to immunoglobulin molecules and immunologically active portions of immunoglobulin molecules, i.e., molecules that contain an antigen binding site which specifically binds an antigen, such as to one of the binding partners, and does not bind other antigens in a sample. Antibodies include, but are not limited to, monoclonal antibodies, polyclonal antibodies, multispecific antibodies, human antibodies, humanized antibodies, chimeric antibodies, single chain Fv (scFv), single chain antibodies, anti-idiotypic (anti-Id) antibodies, F(ab) fragments, F(ab')$_2$ fragments, and epitope-binding fragments of any of the above.

The antibodies may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety oftechniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Antibodies may also be generated using various phage display methods known in the art. In phage display methods, functional antibody domains are displayed on the surface of a phage particles which carry the polynucleotide sequences encoding them. In a particular, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol Methods* 182:41–50(1995); Ames et al., *J. Immunol. Methods* 184:177–186(1995); Kettleborough et al., *Eur. J. Immunol.* 24:952–958 (1994); Persic et al., *Gene* 187 9–18 (1997); Burton et al., *Advances in Immunology* 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference; in its entirety.

Chimeric antibodies can be produced using any technique known to those of skill in the art. See e.g., Morrison, *Science* 229:1202 (1985); Oi et al., *BioTechniques* 4:214 (1986); Gillies et al., (1989) *J. Immunol. Methods* 125:191–202; U.S. Pat. Nos. 5,807,715; 4,816,567; and 4,816,397, which are incorporated herein by reference in their entirety. A chimeric antibody is a molecule in which different portions of the antibody are derived from different animal species, such as antibodies having a variable region derived from a murine monoclonal antibody and a human immunoglobulin constant region.

Human antibodies can be produced using any technique known to those of skill in the art. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, *Molecular Immunology* 28(4/5):489–498 (1991); Studnicka etal., *Protein Engineering* 7(6):805–814 (1994); Roguska. et al., PNAS 91:969–973 (1994)), and chain shuffling (U.S. Pat. No. 5,565,332).

Human antibodies can be made by a variety ofmethods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. For an overview of this technology for producing human antibodies, see Lonberg and Huszar (1995, *Int. Rev. Immunol.* 13:65–93). For a detailed discussion ofthis technology for producing human antibodies and human monoclonal antibodies and protocols for producing such antibodies, see, e.g, PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

5.2.2. ASSAY FORMATS

The assay can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the viral protein and host cell protein. On the other hand, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, one binding partner, e.g, either the viral protein or the host cell protein, is anchored onto a solid surface, and its binding partner, which is not anchored, is labeled, either directly or indirectly. In practice, microtiter plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds that inhibit complex or which disrupt preformed complexes can be identified.

In an alternate embodiment of the invention, a homogeneous assay can be used. In this approach, a preformed complex of the host cell and viral protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will reset in the generation of a signal above background. In this way, test substances that disrupt the viral protein-host cell protein interaction can be identified.

For example, in a particular embodiment for NPI-1, NPI-1 can be prepared for immobilization using recombinant DNA techniques described in section 5.2.1., supra. Its coding region can be fused to the glutathione-S-transferase (GST) gene using the fusion vector pGEX-5X-1, in such a manner that its binding activity is maintained in the resulting fusion protein. NP can be purified and used to raise a monoclonal antibody, specific for NP, using methods routinely practiced in the art and described above. This antibody can be labeled with the radioactive isotope $^{125}$I, for example, by methods routinely practiced in the art. In a heterogeneous assay, e.g., the GST-NPI-1 fusion protein can be anchored to glutathione-agarose beads. NP can then be added in the presence or absence of the test compound in a manner that allows NP to interact with and bind to the NPI-1 portion of the fusion protein. After the test compound is added, unbound material can be washed away, and the NP-specific labeled monoclonal antibody can be added to the system and allowed to bind to the complexed binding partners. The interaction between NP and NPI-1 can be detected by measuring the amount of radioactivity that remains associated with the glutathione-agarose beads. A successful inhibition of the interaction by the test compound will result in a decrease in measured radioactivity.

Alternatively, the viral binding partner, such as NS1, can be prepared for immobilization using recombinant DNA techniques described in section 5.2.1., supra. The NS1 coding region can be fused to the glutathione-S-transferase (GST) gene using a fusion vector such as pGEX-5X-1, in such a manner that its binding activity is maintained in the resulting fusion protein. A corresponding host cell binding partner, such as NS1-BP can be purified and used to raise an NS1-BP-specific monoclonal antibody which can be labeled with a radioactive isotope, using methods described below in section 5.2.1.3. In a heterogeneous assay, e.g., the GST-NS1 fusion protein can be anchored to glutathione-agarose beads. NSI-BP can then be added in the presence or absence of the test compound in a manner that allows NS1-BP to interact with and bind to the NS1 portion of the fusion protein. After the test compound is added, unbound material can be washed away, and the NS1-specific labeled monoclonal antibody can be added to the system and allowed to bind to the complexed binding partners. The interaction between NS1 and NS1-BP can be detected by measuring the amount of radioactivity that remains associated with the glutathione-agarose beads. A successful inhibition of the interaction by the test compound will result in a decrease in measured radioactivity.

In another particular embodiment, for NS1-BP, for example, a GST-NS1-BP fusion protein and NS1 (or conversely, a GST-NS1 fusion protein and NS1-BP) can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by measuring the radioactivity associated with the beads.

In another embodiment of the invention, these same techniques can be employed using peptide fragments that correspond to the binding domains of the viral and host cell proteins, respectively, in place of one or both of the full length proteins. These binding domains can be identified, as described in section 5.2.1., supra. For example, and not by way of limitation, NS1-BP can be anchored to a solid material as described above in this section by making a GST-NS1-BP fusion protein and allowing it to bind to glutathione agarose beads. NS1 can be labeled with a radioactive isotope, such as $^{35}S$, and cleaved with a proteolytic enzyme such as trypsin. Cleavage products can then be added to the anchored GST-NS1-BP fusion protein and allowed to bind. After washing away unbound peptides, labeled bound material, representing the NS1 binding domain, can be eluted, purified, and analyzed for amino acid sequence by methods described in section 5.2.1., supra. Peptides so identified can be produced synthetically or fused to appropriate facilitative proteins using recombinant DNA technology, as described in section 5.2.1., supra.

In accordance with the invention, a given compound found to inhibit one virus may be tested for general antiviral activity against a wide range of different viruses that have analogous dependencies on host cell proteins. For example, and not by way of limitation, a compound that inhibits the interaction of influenza virus NS1 with NS1-BP by binding to the NS1 binding site can be tested, according to the assays described in section 5.3. infra, against other viruses, particularly those that have similar proteins, e.g., parainfluenza viruses.

5.3. ASSAYS FOR ANTIVIRAL ACTIVITY

Any of the inhibitory compounds that are identified in the foregoing assay systems may be tested for antiviral activity.

5.3.1. VIRAL GROWTH ASSAYS

The ability of an inhibitor identified in the foregoing assay systems to prevent viral growth can be assayed by plaque formation or by other indices of viral growth, such as the $TCID_{50}$ or growth in the allantois of the chick embryo. In these assays, an appropriate cell line or embryonated eggs are infected with wild-type influenza virus, and the test compound is added to the tissue culture medium either at or after the time of infection. The effect of the test compound is scored by quantitation of viral particle formation as indicated by hemagglutinin (HA) titers measured in the supernatants of infected cells or in the allantoic fluids of infected embryonated eggs; by the presence of viral plaques; or, in cases where a plaque phenotype is not present, by an index such as the $TCID_{50}$ or growth in the allantois of the chick embryo, or with a hemagglutination assay.

An inhibitor can be scored by the ability of a test compound to depress the HA titer or plaque formation, or to reduce the cytopathic effect in virus-infected cells or the allantois of the chick embryo, or by its ability to reduce viral particle formation as measured in a hemagglutination assay.

An inhibitor can also be scored by the ability of a test compound to decrease the amount of a viral protein, e.g., rhabdovirus M protein, released from cells in a functional budding assay, such as the one described in Justice, et al., 1995 (J. Virol., 69, 3156–3160) and used in the experiments described in the example in section 9.1.5 infra).

5.3.2. ANIMAL MODEL ASSAYS

The ability of an inhibitor to prevent replication of viruses such as picornaviruses, caliciviruses, astroviruses, togaviruses, flaviviruses, coronaviruses, arteriviruses, retroviruses, paramyxoviruses (including parainfluenza viruses, measles virus, mumps virus, and respiratory syncytial virus), rhabdoviruses, filoviruses, orthomyxoviruses, orthomyxo-like viruses including Dhori insect virus, bunyaviruses, and arenaviruses; and double-stranded, positive-sense RNA viruses such as reoviruses and bimaviruses, as well as human immunodeficiency virus (HIV), members of the herpes virus family, and adenoviruses, can be assayed in animal models that are natural or adapted hosts or transgenic hosts for the virus. Such animals may include mammals such as pigs, ferrets, mice, monkeys, horses, and primates, or birds. As described in detail in Section 5.5 infra, such animal models can be used to determine the $LD_{50}$ and the $ED_{50}$ in animal subjects, and such data can be used to derive the therapeutic index for the inhibitor of the viral/host cell protein interaction.

5.4. INHIBITORY COMPOUNDS

Inhibitory compounds identified in the foregoing screening assays which may be used in accordance with the invention may include but are not limited to, polypeptides, peptides, peptidomimetics, antibodies, nucleic acids (e.g, RNA and DNA), and small organic or inorganic molecules and other drugs.

Preferably, the inhibitory compounds have a molecular weight of less than 2000 Daltons, more preferably less than 1500 Daltons, even more preferably less than 1000 Daltons, and most preferably, less than 700 Daltons.

Peptides having an amino acid sequence corresponding to the domain of the host cell protein that binds to the viral protein may be used to compete with the native viral protein and, therefore, may be useful as inhibitors in accordance with the invention. Similarly, peptides having an amino acid sequence corresponding to the domain of the viral protein that binds to the host cell protein may be used. Such peptides may be synthesized chemically or produced via recombinant DNA technology using methods well known in the art (e.g., Creighton, 1983, Proteins: Structures and Molecular Principles, W. H. Freeman & Co., N.Y., pp. 34–49; Sambrook, et al., 1989, Molecular Cloning: A Laboratory Manual, Cold Spring Harbor Laboratories Press, Cold Spring Harbor, N.Y.). If desired, nonclassical amino acids or chemical amino acid analogs can be introduced as a substitution or addition into such a peptide. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids. Further, peptides can be chemically modified by any chemical modification techniques known to those of skill in the art, including but not limited to specific chemical cleavage by cyanogen bromide, trypsin, chymotrypsin, papain, V8 protease, NaBH₄; acetylation, formylation, oxidation, reduction; metabolic synthesis in the presence of tunicamycin; etc. The peptides may be isolated and purified by standard methods including chromatography (e.g. ion exchange, affinity, and sizing column chromatography), centrifugation, differential solubility, or by any other standard technique for the purification of peptides. Lipofectin or liposomes may be used to deliver the peptides to cells.

Alternatively, antibodies that are both specific for the binding domains of either the host cell or viral proteins and interfere with their interaction may be used. Such antibodies may be generated using standard techniques described in Section 5.2.1., supra, against the proteins themselves or against peptides corresponding to the binding domains of the proteins. Such antibodies include but are not limited to polyclonal, monoclonal, Fab fragments, single chain antibodies, chimeric antibodies, etc. Where whole antibodies are used, internalizing antibodies are preferred. However, lipofectin may be used to deliver the antibody or a fragment of the Fab region which binds to the viral or host cell protein epitope into cells. Where fragments of the antibody are used, the smallest inhibitory fragment that binds to the target protein's binding domain is preferred.

5.5. PHARMACEUTICAL PREPARATIONS AND METHODS OF ADMINISTRATION

The identified compounds that inhibit viral replication can be administered to an animal, preferably a mammal and most preferably a human at therapeutically effective doses to treat, prevent or inhibit viral infection. A therapeutically effective dose is the amount of a compound sufficient to inhibit or reduce viral replication, the amount compound sufficient to induce or enhance an immune response to the virus, or the amount of a compound sufficient to result in amelioration of symptoms of viral infection. In a preferred aspect, the compound administered to treat, prevent or inhibit viral infection is substantially purified (e.g., substantially free from substances that limit its effect or produce undesired side-effects).

Toxicity and therapeutic efficacy of such compounds can be determined by standard pharmaceutical procedures in cell cultures or experimental animals, e.g., for determining the $LD_{50}$ (the dose lethal to 50 of the population) and the $ED_{50}$ (the dose therapeutically effective in 50 of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal infection, or a half-maximal inhibition) as determined in cell culture. Such information can be used to more accurately determine usefuldoses in humans. Levels in plasma may be measured, for example, by high performance liquid chromatography. Suitable doses for antibodies range from 0.1 mg/kg to 100 mg/kg of body weight (generally 10 mg/kg to 20 mg/kg), and suitable doses for peptides or polypeptide range from about 0.001 to 30 mg/kg body weight.

Various delivery systems are known and can be used to administer a compound, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429–4432), construction of a nucleic acid as part of a retroviral or other vector, etc. Methods of introduction include but are not limited to intratumoral, intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g gelatin for use in an inhaler or insufflator may be formulated containing a powder mix of the compound and a suitable powder base such as lactose or starch.

In a specific embodiment, the compound can be delivered in a vesicle, in particular a liposome (see Langer, *Science* 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In a specific embodiment, the compound can be delivered in a controlled release system. In one embodiment, a pump may be used (see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989). In another embodiment, polymeric materials can be used (see Medical Applications of Controlled Release, Langer and Wise (eds.), CRC Pres., Boca Raton, Fla. (1974); Controlled Drug Bioa vailability, Drug Product Design and Performance, Smolen and Ball (eds.), Wiley, New York (1984); Ranger and Peppas, *J Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the compound is a nucleic acid encoding a polypeptide or peptide, the nucleic acid can be administered in vivo to promote expression of its encoded peptide or polypeptide, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, *Proc. Natl. Acad. Sci. USA* 88:1864–1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The compounds can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.5.1. INTRACELLULAR DELIVERY OF PHARMACEUTICAL PREPARATIONS

The identified compounds that inhibit viral replication may be administered intracellularly to a patient at therapeutically effective doses to treat viral infection. In one embodiment, an oligopeptide of the invention is targeted directly to the cytoplasm and/or nucleus of a cell. In a specific embodiment, the targeting system employed is a penetratin or "trojan peptide" targeting system (Derossi, et al., 1998, Trends Cell Biol. 8:84–87).

The trojan peptide targeting system employs a fusion protein created using standard methods of recombinant polypeptide technology. The fusion protein comprises an oligopeptide sequence to be internalized fused to a trojan peptide internalization vector, e.g., penetratin-1 or Antennapedia homeodomain (Antp-HD). The oligopeptide "cargo" and the trojan peptide vector may be coupled by several methods including, but not limited to, 1) chemical synthesis and coupling in which the cargo and the trojan vector are synthesized separately and attached through a disulfide bond; 2) chemical synthesis in tandem in which a peptidic cargo is synthesized in tandem with a trojan vector; and 3) an in vitro recombination approach in which fusion peptides comprising the third helix of Antp-HD, a tag (e.g., myc) and a cargo are expressed in *E. coli and purified (Derossi, et al., 1998, Trends Cell Biol. 8:84–87).

The trojan peptide targeting system may be used to target internalization of fusion proteins of at least 100 amino acids, and possibly longer, depending on the structure of the cargo. Preferably, the fusion proteins are preincubated with small

6. EXAMPLE: THE IDENTIFICATION OF NPI-1 AND ITS INTERACTION WITH INFLUENZA NUCLEOPROTEIN

The yeast interactive trap system was used to identify a cellular protein which interacts with the nucleoprotein of influenza A viruses. This protein, nucleoprotein interactor 1 (NPI-1) is the human homologue of the yeast protein SRP1. SRP1 was previously identified as a suppressor of temperature-sensitive RNA polymerase I mutations (Yano, et. al., 1992, Mol. Cell. Biol. 12:5640–5651). A full length cDNA clone of NPI-1 was generated from HeLa cell poly A+ RNA. The viral NP, which had been partially purified from influenza A/PR/8/34 virus-infected embryonated eggs, could be coprecipitated from solution by glutathione agarose beads complexed with a bacterially expressed glutathione-S-transferase (GST)-NPI-1 fusion protein, confirming the results of the yeast genetic system. Antisera raised against NPI-1 identified a 65 kDa polypeptide from total cellular extracts of both HeLa and MDBK cells. In addition, the viral nucleoprotein was co-immunoprecipitated from influenza A/WSN/33 virus-infected HeLa cells by antisera directed against NPI-1, demonstrating an interaction of these two proteins in infected cells, and suggesting that NPI-1 plays a role during influenza virus replication.

6.1. MATERIALS AND METHODS

6.1.1. YEAST, BACTERIA AND PLASMIDS

Yeast strain EGY48 (Mata trpl ura3 his3 LEU2::pLEXAop6-LEU2) (Zervos, et al., 1993, Cell 72: 222–232) and plasmids pEG202, pSH18–34, and pRFHM1 and the HeLa cell cDNA library constructed in pJG4–5 (Gyuris, et al., 1993, Cell 75: 791–803) were previously described. Similar versions of these plasmids and this yeast host strain are available commercially from Clontech as part of a two fusion protein system. pLexA-NP was constructed by subcloning the cDNA of influenza-A/PR/8/34 NP as a LexA translational fusion gene into pEG202 (FIG. 1). Yeast strains constructed as part of these studies are described in Table 2. *Escherichia coli* MH3 (trpC araD lacXhsdR galU galK) and W31005 were previously described (Hall, et al., 1984, Cell 36: 1057–1065).

6.1.2. SELECTION OF NP INTERACTORS

An interactive trap selection was performed essentially as has been previously described (Gyuris, et al., 1993, Cell 75: 791–803; Zervos, et al., 1993, Cell 72: 222–232). Strain R100 was transformed by the HeLa cDNA library using the lithium acetate method (Ito, et al., 1983, J. Bacteriol. 153: 163–168). $2 \times 10^6$ primary yeast transformants were selected on twelve $25 \times 25$ cm$^2$ his$^-$trp$^-$ glucose plates, pooled and stored at $-70°$ C. Library transformants were selected for leu+ phenotype on his$^-$leu$^-$-galactose plates; the efficiency of plating was approximately $10^{-4}$ leu+ colonies per galactose+ colony. Plasmid DNA was isolated from leu+ library transformants as described by Hoffman and Winston (Hoffman & Winston, 1987, Gene 57: 267–272) and introduced into MH3 cells by electroporation. Library plasmids were selected by plating the transformation mix on 1×A+amp+glucose plates (Miller, 1972, Experiments in Molecular Genetics, Cold Spring Harbor Laboratory Press, Cold Spring Harbor, N.Y.).

cDNAs were analyzed by checking the specificity of interaction with the NP. Each isolated plasmid was introduced into strains RI101 and R 102. These strains harbor pSH18–34, a reporter plasmid encoding β-galactosidase with a GAL1 promoter transcriptionally controlled from upstream LexA binding sites. Strain R102 was used as a negative control for NP-specificity of cloned cDNAs. It contains pRFHM1, which encodes LexA fused to a transcriptionally inert fragment of the *Drosophila melanogaster* bicoid protein. β-Galactosidase activity was assayed on nitrocellulose replicas of the colonies by freeze fracturing the cells and incubating in buffer containing 5-bromo-4-chloro-3-indolyl-β-D-galactoside (X-gal) (Miller, 1972, Experiments in Molecular Genetics, Cold Spring Harbor Laboratory Press, Cold Spring Harbor, N.Y.). Plasmids which conferred both a leu+ and β-gal+ phenotypes in the presence of pLexA-NP but not in the presence of pRFHM1 were saved for further study.

6.1.3. CLONING OF THE 5' TERMINUS OF NPI-1

The 5' terminus of NPI-1 was cloned by rapid amplification of cDNA ends ("RACE") by the method of Frohman (Frohman, 1990, in PCR Protocols: A Guide to Methods and Applications, Innis, et. al., eds., Academic Press Inc., San Diego, p. 28–38; Frohman, et al., 1988, Proc. Natl. Acad. Sci. USA 85: 8998–9002). Reverse transcription of 1 μg of poly A+ HeLa cell RNA was performed using the NPI-1 specific oligonucleotide 5'GCAAAGCAGGAGAAAC-CAC3' (SEQ ID NO:24). First strand cDNA was tailed with dCTP by terminal transferase. PCR amplification of the reverse transcription product was performed with the nested NPI-1 primer 5'GGGTCCATCTGATAGATATGAGAG3' (SEQ ID NO:25) and the 5' RACE anchor primer 5' CUAC-UACUACUAGGCCACGCGTCGACTAC-TACGGGIIGGGIIGGGIIG3' (SEQ ID NO:26; Gibco/BRL). The PCR product was subcloned into pGEM-T (Promega) and was sequenced by standard protocols. 5'RACE products from three independent experiments were cloned and sequenced in order to avoid errors introduced by PCR.

6.1.4. BACTERIAL EXPRESSION AND PURIFICATION OF GST-NPI-1

The NPI-1 cDNA derived from a HeLa cDNA library was subcloned into the EcoRI and XhoI restriction endonuclease sites of the glutathione-S-transferase fusion vector pGEX-5X-1 (Pharmacia) to generate the plasmid pGST-NPI-1. Protein was induced from bacterial expression plasmids in W31005 cells with isopropyl-β-D-galactopyranoside according to standard protocols (Smith & Johnson, 1988, Gene 67: 31–40). Bacteria were pelleted 4 h after induction, washed in ice cold phosphate buffered saline (PBS), and resuspended in one-tenth culture volume PBS+1 Triton X-100. Bacteria were lysed on ice with four 15 s pulses in a Raytheon sonicator at an output setting of 1 amp. Insoluble material was pelleted at 50,000×g for 30 min in a Beckman TL-100.3 rotor.

GST-NPI-1 and GST were purified from bacterial lysates on glutathione-agarose beads (Sigma Chemical Corporation.). Beads were swelled according to the manufacturer's instructions and equilibrated in PBS. Typical binding reactions were done in 500 μl of PBS/0.1 Triton X-100, and included 50 μl bacterial lysate and 10 μl of a 50 slurry of glutathione-agarose beads. Binding reactions were incubated for 5 min at room temperature on a rotating wheel. Beads were collected by centrifugation for 5 s in a microfuge, and were washed three times in PBS.

6.1.5. NP BINDING ASSAY

To assay binding of NP to GST-NPI-1/bead complexes typical reactions were performed in 500 μl of ice cold PBS+0.05 Nonidet P-40 and contained washed GST-NPI- 1/bead complexes and 10 μg partially purified influenza virus polymerase and nucleoprotein preparations (Pol/NP). Virus was prepared from embryonated eggs infected by influenza A/PR/8/34 virus and POL/NP preparations were purified as previously described (Enami, et al., 1990, Proc. Natl. Acad. Sci. USA 87: 3802–3805; Parvin, et al., 1989, J. Virol. 63: 5142–5152). NP was bound for 1 h at 4° C. on a rotating wheel. Beads werecollected by centrifugation for 5 s in a microfuge, and were washed three times in PBS+0.05 NP-40. Washed beads were resuspended in 50 μl SDS sample buffer (Sambrook, et al., 1989, Molecular Cloning: A Laboratory Manual, Cold Spring Harbor Laboratories Press, Cold Spring Harbor, N.Y.), boiled for 5 min, and pelleted in a microfuge. 10 μl of each supernatant was separated by electrophoresis on a 12.5 SDS-polyacrylamide gel. Gels were either stained with Coomassie blue or processed for immunoblot analysis. NP was detected by immunoblotting with the monoclonal antibody HT103.

6.1.6. ANTISERA AND IMMUNOBLOTTING

Polyclonal rabbit antisera against NPI-1 was generated by immunization of a female NZY Rabbit (Buckshire Farms) with 200 μg of purified GST-NPI-1 in complete Freund's adjuvant, followed by two boosts of 100 μg in incomplete Freund's adjuvant at three week intervals. The specificity of antisera was demonstrated by immunoblot analysis of GST-NPI-1 in bacterial lysates. Immunoblots were performed by standard methods (Harlow and Lane, 1988, Antibodies: A Laboratory Manual, Cold Spring Harbor Laboratories Press, Cold Spring Harbor, N.Y.). Sera were used at a dilution of 1:1000.

6.1.7. VIRUSES AND CELLS

Total cell lysates from HeLa and MDBK cells were generated by direct lysing of cells in SDS-sample buffer, followed by shearing of chromosomal DNA by passage through a 21 ga. syringe. Cytoplasmic extracts were generated by lysing cells in ice cold NP-40 lysis buffer (10 mM Tris-Cl, pH 8.0; 100 mM NaCl; 1 mM EDTA; 1 mM DTT; 1 Nonidet P-40; 1 mM 4-(2-aminoethyl) benzenesulfonylfluoride-hydrochloride (Pefabloc)). After 10 min on ice nuclei were removed by centrifugation. Proteins were separated by SDS-PAGE, transferred to nitrocellulose and visualized by immunoblotting.

To generate infected cell lysates containing metabolically labeled proteins 4×10$^6$ HeLa cells were infected with influenza A/WSN/33 virus at a multiplicity of 10 for 45 min at 37° C. Infection was allowed to proceed in DMEM+0.1 BSA for 5 h at which time cells were labeled with 50 μCi $^{35}$S-methionine+50 μCi $^{35}$S-cystine in MEM-cys-met for 1 h. Extracts were prepared by resuspending infected cells in 650 μl ice cold NP-40 lysis buffer followed by two 15 s pulses in a Raytheon sonicator to disrupt nuclei. Insoluble cell debris was removed by centrifugation at 100,000×g in a TL-100.3 Beckman rotor. 5 μl anti-NPI-1 sera was incubated on ice for 1 h with 100 μl infected cell lysates. Immune complexes were precipitated from solution by incubation with Sepharose-4B linked protein G beads (Sigma Chemical Co.) for 1 h. Beads were collected by centrifugation, washed three times in NP-40 lysis buffer, and resuspended in SDS-sample buffer. Precipitated proteins were separated by SDS-PAGE and visualized by autoradiography.

6.2. RESULTS

6.2.1. ISOLATION OF NPI-1

The interactive trap was used to identify proteins which specifically interact with the influenza A virus nucleoprotein (NP). The interactive trap is one of several genetic systems recently developed which uses the modular nature of transcription activators to detect protein:protein interactions (Chien, et al., 1991, Proc. Natl. Acad. Sci. USA 88: 9578–9582; Dalton & Treisman, 1992, Cell 68: 597–612; Durfee, et al., 1993, Genes Dev. 7: 555–569; Gyuris, et al., 1993, Cell 75: 791–803; Vojtek, et al., 1993, Cell 74: 205–214; Zervos, et al., 1993, Cell 72: 222–232). The interactive trap consists of three components: (1) a reporter gene that has no basal transcription; (2) a fusion protein which contains a LexA DNA binding domain that is transcriptionally inert; and (3) proteins encoded by an expression library, which are expressed as fusion proteins containing an activation domain (FIG. 1A). Interaction of the LexA fusion protein and the fusion protein containing the activation domain will constitute a bimolecular transcriptional activator which, in this case, will confer the ability to grow on media lacking leucine (Gyuris, et al., 1993, Cell 75: 791–803; Zervos, et al., 1993, Cell 72: 222–232). In the absence of this interaction the leu2 gene is not transcribed.

The NP gene of influenza A/PR/8/34 virus was subcloned as a translational fusion gene with the LexA gene into pEG202 to generate pLexA-NP (FIG. 1B). Strain R100 (Table II), which contains pLexA-NP, was transformed with a HeLa cell cDNA library constructed in pJG4–5. pJG4–5 contains an activation domain under control of a GAL1 promoter (Gyuris, et al., 1993, Cell 75: 791–803).

TABLE II

YEAST STRAINS USED

| Strains | Genotype |
| --- | --- |
| EGY48 | Mata trp1.ura3.his3 LEU2::pLEXAop6-LEU2 |
| R100 | EGY48, pLexA-NP(TRP1) |
| R101 | EGY48, pLexA-NP, pSH18-34(HIS3) |
| R102 | EGY48, pRFHM1(TRP1), pSH18-34 |

Library plasmids were rescued from 100 leu+ colonies. Reproducibility of the interaction of the NP with the encoded library proteins was tested by transforming library plasmids into strain R101. Transformants were screened for galactose-dependent β-galactosidase activity and growth on media lacking leucine. Specificity for NP was analyzed by checking the ability of library plasmids to confer growth on leu$^-$ media and β-galactosidase activity in connection with a different LexA fusion plasmid, pRFHM1, encoding a fragment of the Drosophila melanogaster bicoid protein. Twenty-three library plasmids were confirmed to encode NP-interactive proteins. Twelve identical 2.1 kbp clones encoded the carboxy terminal fragment of a protein termed nucleoprotein interactor 1 (NPI-1). Partial DNA sequencing showed that NPI-1 is the human homologue of the yeast SRP1 gene (infra).

6.2.2. CLONING AND SEQUENCING OF THE NPI-1 cDNA

The 2.1 kbp NPI-1 cDNA in pJG4–5 was sequenced by standard protocols. The 5'cDNA terminus of the NPI-1 gene was cloned by 5'RACE. cDNAs from 3 independently derived NPI-1 5'RACE products were cloned and sequenced. Nucleotide and derived amino acid sequences of NPI-1 are shown in FIG. 2. The sequence reveals a 2.9 kbp cDNA which encodes a protein of 527 amino acids with a calculated molecular weight of 58,754 Da and a pI=4.74. The carboxyl terminal 265 amino acids were encoded by the interactive trap library plasmid and interact with the viral NP.

Comparison of the deduced amino acid sequences in the GenBank and EMBL databases using the FASTA and TFASTA programs (Deveraux, et al., 1984, Nucleic Acids Res. 12:387–395) demonstrated that NPI-1 is the human homologue of the *Saccharomyces cerevisiae* protein SRP1 (Yano, et al., 1992, Mol. and Cell. Biol. 12: 5640–5651). SRP1 was cloned as an allele-specific suppressor of ts mutations in the zinc-binding domain of the A190 subunit of RNA polymerase I. The amino. acid sequence is highly conserved between NPI-1 and SRP1: 50% identity and 81% similarity at the amino acid level. The amino terminus of NPI-1 has a potential nuclear localization signal (Chelsky, et al., 1989, Mol. Cell. Biol. 9:2487–2492); amino acids 25 to 49 are rich in arginine, and contain a stretch of four consecutive arginines at amino acids 28 to 31. NPI-1, like SRP 1, contains a series of 8 consecutive ARM motifs, which are 42 amino acid protein subsequences originally identified in the Drosophila armadillo protein (Peifer, et al., Cell 76: 789–791, 1994; Yano, et al., 1992, Mol. and Cell. Biol. 12: 5640–5651) (FIGS. 3A–3B).

6.2.3. NPI-1 BINDS TO NP IN VITRO

In order to demonstrate that the NPI-1 binds to the viral NP, the NPI-1 cDNA fragment (amino acids 262 to 527) was subcloned into the bacterial expression vector pGEX-5X-1 yielding a glutathione S-transferase fusion gene. The expressed fusion protein was purified from bacterial lysates on glutathione agarose beads. NP, which had been partially purified with the viral polymerase from influenza A/PR/8/34 virus was specifically precipitated from solution by glutathione agarose beads complexed with GST-NPI-1 (FIG. 4). The NP band migrates slightly faster than that of the GST-NPI-1 fusion protein. The identity of this protein was confirmed by immunoblot analysis using the anti-NP monoclonal antibody HT103 (FIG. 4, lane 8).

6.2.4. IMMUNODETECTION OF NPI-1 IN CELL EXTRACTS

Rabbit antisera raised against GST-NPI-1 were used to identify a polypeptide from total cellular extracts of both HeLa and MDBK cells with an apparent molecular weight of 65 kDa (FIG. 5). The molecular weight predicted from the derived amino acid sequence of the CDNA is slightly smaller (59 kDa). A lower amount of NPI-1 was present in the cytoplasmic fraction-generated by lysis of cells in the presence of NP-40 than in the total cellular extract suggesting that most of NPI-1 is located in the nucleus (FIG. 5). This is consistent with results localizing the NPI-1 homologue SRPI to the nucleus of yeast cells by immunofluorescence (Yano, et al., 1992, Mol. and Cell. Biol. 12: 5640–5651). Localization of NPI-1 to a particular intracellular compartment by immunofluorescence experiments has not been possible due to the high background fluorescence of the antisera preparations used.

6.2.5. NPI-1 INTERACTS WITH NP IN INFECTED CELLS

Since NP formed a complex with NPI-1 in vitro, whether NP and NPI-1 form a complex in infected cells was examined. NP was specifically coimmunoprecipitated from extracts of influenza A/WSN virus infected HeLa cells by antisera directed against NPI-1 (FIG. 6). This demonstrates an interaction of the viral NP and the cellular NPI-1 during influenza A virus infection.

7. EXAMPLE

THE IDENTIFICATION OF NS1I-1 AND ITS INTERACTION WITH INFLUENZA NS1 PROTEIN

In the example described below, the yeast interactive trap system was used to identify a human protein, NS1I-1 (NS1-interactor-l), from a HeLa cell cDNA library on the basis of its binding to NS1 of influenza A virus. NS1I-1 is shown herein to be recognized not only by NS1 proteins from five human and avian influenza A strains, but also by NS1 of influenza B virus. Surprisingly, NS1I-1 is homologous to a steroid dehydrogenase isolated from pigs (Leenders, et al., 1994, Eur. J. Biochem. 222: 221–227). Several proteins with a dehydrogenase function have recently been shown not only to have enzymatic activity but also to be involved in post-transcriptional events of gene-expression (Hentze, 1994, Trends Biochem. Sci. 19: 101–103). This strong conservation supports an important functional role of the NS1I-1 interaction during the viral life cycle.

7.1. MATERIALS AND METHODS

7.1.1. YEAST *E. COLI* STRAINS, AND PLASMIDS

Manipulations of nucleic acids, *Escherichia coli* and yeast followed essentially standard procedures as described elsewhere (Ausubel, et al., 1992, Current Protocols in Molecular Biology, Green Publishing Associates, Inc., and John Wiley & sons, Inc., New York). The yeast strains EGY40 (Mata irpl ura3 his3) and EGY48 (Mata trpl ura3 his3 LEU2::pLEX-Aop6-LEU2) as well as plasmids pEG202, pRFHM1, and pSH18–34, and the HeLa cell cDNA constructed in pJG4–5 have been described (Gyuris, et al., 1993, Cell 75: 791–803; Zervos, et al., 1993, Cell 72: 222–232). *E. coli* strains used for cloning and expression were MH3 (trpC araD lacX hsdR galU galK), DH5α (F⁻Φ80dlacZΔM 15 Δ(lacZY–argF) U169 deoR recA1 endA1 hsdR17($r_K$–$m_K$+) supE44λ-thi-gyrA96 relA1), and BL26 (F⁻ompT hsdS$_B$($r_B^-$m$_B^-$) gal dcm). pLexA-NS1 was constructed by subcloning the cDNA of the NS segment of influenza virus A/PR/8/34 downstream of the LexA gene in pEG202. pGEX-NS1I-1 was constructed by subcloning the HeLa cDNA-insert of library plasmid pK5 as an EcoRI/XboI-fragment into pGEX-5X-l (Pharmacia). DNA-oligonucleotides used were: GSP-I, 5'-dTCCTGATGTTGCTGTAGACG-3' (SEQ ID NO:27), GSP-II, 5'-dGCACGACTAGTATGATTTGC-3' (SEQ ID NO:28), and the 5'RACE anchor primer (BRL), 5'-dCUACUACUACUAGGCCACGCGTCGACTACTA CGGGIIGGGIIGGGIIG-3' (SEQ ID NO:26).

7.1.2. IDENTIFICAFION OF NS1-INTERACTORS

The interactive trap selection was performed essentially as described for NPI-1 in Section 6.1.2, above. The selection strain was constructed by transforming EGY48 with the bait plasmid pLexA-NS1 and the lacZ-reporter plasmid pSH18–34. Expression of lacZ from pSH18–34 is transcriptionally controlled by a GAL1 promoter and LexA-dependent operator sites. A HeLa cell cDNA library was introduced into the selection strain using the lithium acetate method (Ito, et al., 1983, J. Bacteriol. 153: 163–168). Primary transformants were selected on trp⁻his⁻ura⁻ glucose plates. 1×10⁶ cells representing 3.3×10⁵ independent transformants were plated on 150 mm trp⁻his⁻ura⁻leu⁻-galactose plates to select for clones expressing NS1-interacting proteins. Viable cells were replica-transferred to a nitrocellulose filter and assayed for β-galactosidase activity using 5-bromo-4-chloro-3-indolyl β-D-galactoside (X-gal) as described (Ausubel, et al., 1992, Current Protocols in Molecular Biology, Green Publishing Associates, Inc., and John Wiley & sons, Inc., New York). Positive clones were tested in a second round of selection by replica plating onto X-gal trp⁻his⁻ura⁻ galactose plates. Plasmid DNA was isolated from yeast clones expressing β-galactosidase activity only on galactose plates and library plasmids were recovered by transformation into *E. coli* MH3 as described in Section 6.1.2, above. The specificity of the isolated plasmids was tested by co-transformation with pLexA-NS1 or pRFHM1 into EGY40 harboring pSH18–34. pRFHM1 expresses an unrelated LexA-bicoid fusion protein. The resulting strains were assayed for β-galactosidase activity on X-gal trp⁻his⁻ura⁻ plates containing glucose or galactose. Plasmids that induced β-galactosidase only in the presence of galactose and only in conjunction with pLexA-NS1 were considered to encode true interacting proteins.

7.1.3. CLONING OF NS1I-1 5'-END cDNA

Cloning of cDNA derived from the 5'-end of NS1I-1 mRNA followed a RACE-procedure (rapid amplification of cDNA ends) (Frohman, et al., 1988, Proc. Natl. Acad. Sci. USA 85: 8998–9002) using a 5'RACE-kit (BRL). First strand CDNA was synthesized from 1 µg of HeLa cell poly(A)-RNA hybridized to 2.5 pmol NS1I-1-specific oligonucleotide GSP-1 using reverse transcriptase. The cDNA was tailed at the 5'-end with dC by terminal transferase. The product was used as a template for the amplification of a 5'RACE-product by PCR using a nested oligonucleotide GSP-II and an anchor primer provided by the kit. The resulting fragment was subcloned in pGEM-T (Promega) to form pRACENS1I-1, and sequenced by the standard dideoxy method. The NCBI-search was conducted using Fasta, Tfasta. Sequence comparison was conducted using Bestfit.

7.1.4. NORTHERN BLOT ANALYSIS

1 µg of HeLa cell poly(A)-RNA was separated on a 1 agarose-fornaldehyde gel, transferred to a nylon membrane (Nytran, Amersham), and UV-crosslinked. The RNA was hybridized to a $^{32}$P-labeled, NS1I-1 specific probe derived form a fragment (corresponding to positions +791 to +1745) of the original pK5 library isolate as described (Ausubel, et al., 1992, Current Protocols in Molecular Biology, Green Publishing Associates, Inc., and John Wiley & sons, Inc., New York).

7.1.5. VIRUSES, CELLS, AND EXTRACTS

Influenza strains A/WSN/33 (H1N1), A/Berkeley/1/68 (H2N2), A/Beijing/32/92 (H3N2), A/duck/Alberta/76 (N12N5), A/turkey/Oregon/71 (H7N5), and B/Lee/40 were grown in the allantoic cavity of 10 days old embryonated chicken eggs. Confluent monolayers of Madin Darby canine kidney-(MDCK)-cells were infected with influenza viruses at an m.o.i. of 10 for one hour in 35 mm dishes. Infection was continued at 37° C. (influenza A viruses) or 35° C. (influenza B/Lee/40) for 5 hours in MEM-medium containing 0.1 bovine serum albumin. Cells were labeled with 100 µCi of $^{35}$S-methionine and $^{35}$S-cysteine (ICN) per dish for one hour in MEM-met⁻cys⁻medium. Cells were washed and scraped in ice-cold phosphate buffered saline (PBS). Cells from one dish were lysed with 500 µl NET-N buffer (10 mM Tris/HCl pH 8.0, 1 mM EDTA, 150 mM NaCl, 0.05 Nonidet P 40) and two 30 second pulses in a Raytheon sonicator at a setting of 1A. Lysates were centrifuged for 10 minutes at 20,000 rpm in a TL100.3 rotor. The supernatants were used for precipitation of proteins.

7.1.6. EXPRESSION OF GST-NS1I-1 FUSION PROTEIN IN E. COLI AND PRECIPITATION OF VIRAL PROTEINS FROM CELL EXTRACTS

NS1I-1 was expressed in E. coli BL26 from pGEX-NS1I-1 as a GST (glutathione-S-transferase)-NS1I-1 fusion protein with a predicted molecular weight of 77 kDa. Production of GST-NS1I-1 was induced using isopropyl-β-D-galactopyranoside essentially as described (Smith & Johnson, 1988, Gene 67: 31–40). GST-NS1I-1 was adsorbed from bacterial lysates to glutathione sepharose beads (Pharmacia) as recommended by the manufacturer. Beads-were washed three times with PBS to remove contaminating proteins. 10 µl of glutathione sepharose coated with GST-NS1I-1 fusion protein was rotated with 100 µl extract of virus-infected MDCK-cells (see above) in 750 µl NET-100 buffer (20 mM Hepes, pH 8.0, 100 mM NaCl, 0.5 mM DTT) for 90 minutes at 4° C. The beads were washed three times with PBS/0.05 NP-40 and precipitated proteins were analyzed by SDS-gel electrophoresis and autoradiography. In parallel reactions, viral proteins were immunoprecipitated from 50 µl of infected cell extracts using 5 µl of anti-NS1 or anti-M1 antiserum and protein A agarose as described (Harlow and Lane, 1988, Antibodies: A Laboratory Manual, Cold Spring Harbor Laboratories Press, Cold Spring Harbor, N.Y.). As a negative control, GST protein was expressed in BL26 from pGEX-5X-1 and used the same way in the co-precipitation assay.

7.2. RESULTS

7.2.1. ISOLATION OF NS1-INTERACTING FACTORS

The yeast interaction trap system (Gyuris, et al., 1993, Cell 75: 791–803; Zervos, et al., 1993, Cell 72: 222–232) was used to identify cellular proteins that interact with the non-structural protein NS1 of influenza A virus. A LexA-NS1 fusion protein was used as bait to screen library in which HeLa cell cDNAs were expressed as fusions with an acidic transcription activation domain (Gyuris, et al., 1993, Cell 75: 791–803, #159). Colonies were selected, in which either of two reporter genes, LEU2 and lacZ, were activated by the cDNA-encoded proteins. This double selection scheme was used to increase the stringency, because in an initial screen a high proportion of candidates scored negative in subsequent genetic tests. The library plasmids were isolated from the selected clones.

The binding specificity of the encoded fusion proteins was tested by assaying the activation of a lacZ-reporter gene encoded on pSH18–34. Expression of β-galactosidase from this plasmid is transcriptionally controlled by LexA-specific operator sites. The isolated library plasmids were co-transformed with pLexA-NS1 or pRFHM1 into EGY40 harboring pSH18–34. pRFHM1 expresses a LexA-bicoid fusion protein and was used as a non-specific operator-binding control. The resulting strains were assayed for β-galactosidase activity specifically on X-gal plates containing galactose, but not glucose. From 3.3×10⁵ independent library transformants, three plasmids were isolated that induced galactose-specific activation of the lacZ reporter gene only in combination with pLexA-NS1. Sequence analysis indicated that the three plasmids were each derived from different cellular cDNAs.

7.2.2. CLONING AND SEQUENCE ANALYSIS OF NS1I-1

One of the isolated plasmids, pK5, was analyzed further. It carried a cDNA-insert of 1781 bp with an open reading frame of 1413 nucleotides followed by 368 nucleotides of a potentially untranslated region (FIGS. 12A–12D). The cDNA terminated with an oligo(A)-tract and had a consensus poly(A)-site at positions 2526–2531. Northern blot analysis of HeLa cell poly(A)-RNA using a NS1I-1-specific probe detected one single transcript of about 3.0 kb suggesting that the pK5 insert represented an incomplete CDNA (FIG. 13). The remaining NS1I-1 cDNA was cloned by a 5'RACE procedure (Frohman, et al., 1988, Proc. Natl. Acad. Sci. USA 85: 8998–9002). Four independent clones were sequenced that differed only in length at the very 5'-end. The longest 5'RACE product, contained in pRACENS1I-1, extended the NS1I-1 sequence for 893 nucleotides upstream totaling in a cDNA of 2674 bp (FIGS. 12A–12D). The sequence has one long open reading frame encoding a protein of 735 amino acids with a predicted molecular mass of 79.5 kDa and a pI of 9.06. The putative ATG-start codon is located 103 nucleotides downstream of the 5'-end and is in the context of a sequence consistent with its being a translational start (Kozak, 1989, J. Cell Biol. 108: 229–241).

Sequence comparisons through the EMBL- and Genbank databases using the FASTA- and TFASTA-analysis programs revealed that NS1I-1 is highly homologous to porcine 17β-estradiol dehydrogenase (Leenders, et al., 1994, Eur. J. Biochem. 222: 221–227). The two cDNAs are 86 identical on the nucleic acid level. The encoded proteins are 84 identical and are 92 similar when allowing for conserved amino acid substitutions. NS1I-1 cDNA also shows strong homology to ten human cDNA fragments that have been isolated as expressed sequence tags, as revealed by a BLAST-analysis of the NCBI-database (fragments are between 134 to 556 bp in length). These cDNAs were derived from different tissues including liver, spleen, brain, adipose tissue, and adrenals tissue indicating a broad expression of NS1I-1 in the body.

The encoded NS1I-1 protein features two conserved sequence motifs of the short-chain alcohol dehydrogenase family (Persson, et al., 1991, Eur. J. Biochem. 200: 537–543). Specifically, amino acids 15 to 22 (TGAGAGCG; SEQ ID NO:29) are similar to the potential co-factor binding site, and residues 163 to 167 (YSAAK; SEQ ID NO:30) correspond to a short stretch that has been suggested to participate in catalysis (Chen, et al., 1993, Biochemistry 32: 3342–3346). The presence of the tri-peptide AKL at the carboxy-terminus was also noted. Similar tri-peptide motifs have been found to serve as targeting signals for import into microbodies (for a review, see de Hoop & Ab, 1992, Biochem. J. 286: 657–669). However, the presence of this signal does not automatically direct a protein to these organelles (de Hoop & Ab, 1992, Biochem. J. 286: 657–669).

7.2.3. NS1I-1 BINDS NS1 PROTEIN FROM EXTRACTS OF INFLUENZA A VIRUS INFECTED CELLS

In order to confirm a physical interaction between NS1I-1 protein and NS1 expressed in influenza virus infected cells, a co-precipitation assay was performed as similarly described in Section 6.2.3, above, for NPI-1. A glutathione-S-transferase (GST)-NS1I-1 fusion gene was constructed and expressed in *E. coli* GST-NS1I-1 fusion protein from bacterial lysate was absorbed to the affinity matrix glutathione agarose and purified from contaminating bacterial proteins. The immobilized fusion protein was used to bind and precipitate $^{35}$S-labeled proteins from extracts of MDCK cells infected with human influenza A/WSN/33 viruses (FIG. 14). The NS1 protein of this strain is 98 identical to its counterpart from A/PR/8/34 used in the yeast interaction screen. Aliquots of the same extract were used to in parallel reactions to immunoprecipitate influenza virus proteins NS1 and M1. The precipitated proteins were analyzed by SDS-gel electrophoresis and visualized by fluorography. FIG. 14 shows, that GST-NS1I-1 efficiently precipitated a protein band co-migrating with immunoprecipitated NS1 protein from infected cell extract (compare lanes 2 and 3). This interaction was specific for NS1I-1 since no proteins were detected in precipitates using GST only (lane 6). In addition, no proteins were precipitated by GST-NS1I-1 from mock-infected cells (lane 8), showing that a virus induced protein was recognized by NS1I-1. This experiment confirmed, that NS1I-1 interacts specifically with the NS1 protein of influenza A virus.

If this interaction is important for the viral life-cycle one would expect it to be conserved. Consequently, the binding of NS1I-1 to NS1 proteins from other influenza A strains should be detectable despite of their considerable variation in the primary structure (Baez, et al., 1981, Virology 113: 397–402; Ludwig, et al., 1991, Virology 183: 566–577). Therefore the interaction between NS1I-1 and NS1 was examined using the same co-precipitation assay described above, with extracts from cells infected with different influenza A and B virus strains.

Figure 15A:
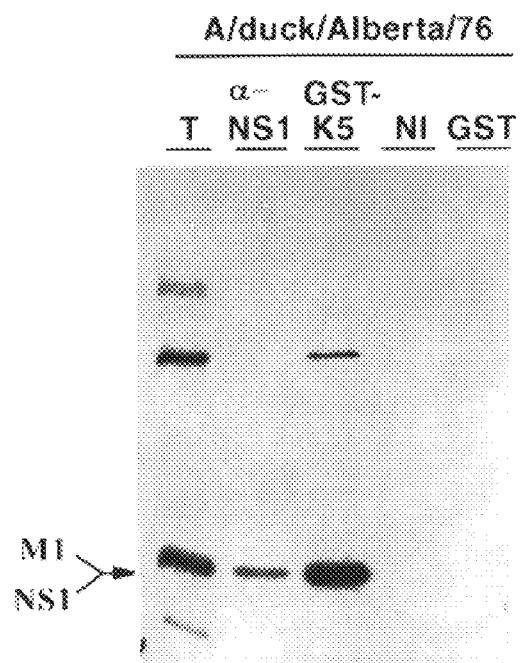
Figure 15B:
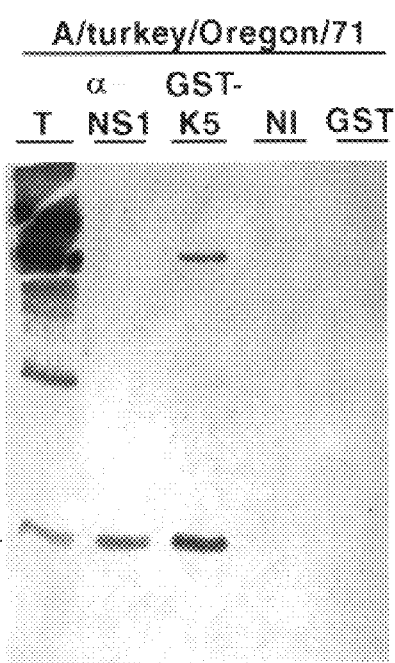
Figure 15C:
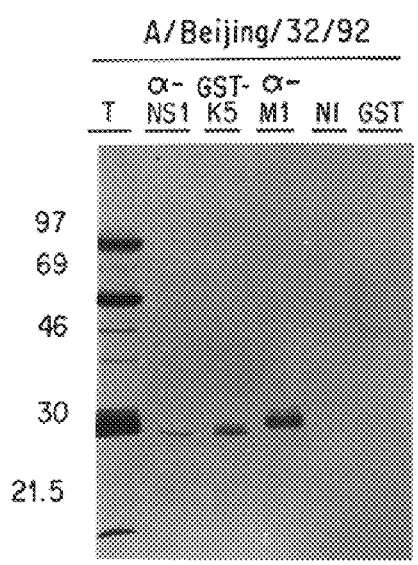
Figure 15D:
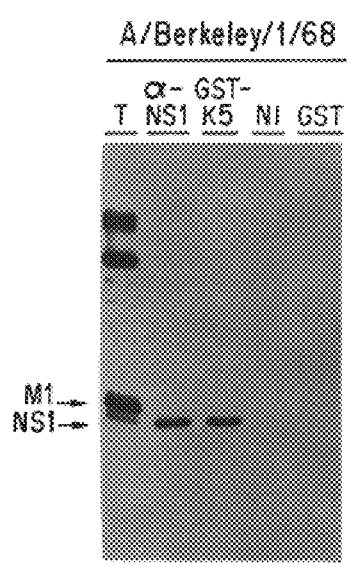
Figure 15E:
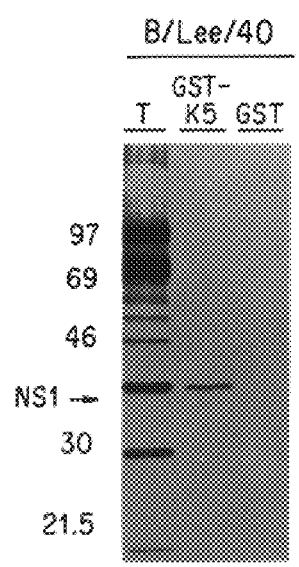

Mutations accumulate in the NS1 gene at a steady rate over time (Buonagurio, et al., 1985, Science 232: 980–982). Thus, the time-span between the isolation of two strains is reflected in the sequence variation of its NS1 proteins (Ludwig, et al., 1991, Virology 183: 566–577; Buonagurio, et al., 1985, Science 232: 980–982). NS1I-1 binding to NS1 proteins from two recently isolated human influenza A strains A/Beijing/32/92 and A/Berkeley/1/68 was examined. As can be seen in FIGS. 15C and 15D, respectively, NS1 proteins fron both strains were specifically precipitated (FIGS. 15C and 15D, lanes "GST-K5"). A low immunoprecipitation efficiency of NS1 protein from the Beijing-strain (FIG. 15C) was reproducibly observed. The NS1 proteins ofAJBerkeley/1/68 and A/WSN/33 are 90.8 identical to each other. The NS1 sequence of A/Beijing/32/92 is not known.

The following analyses were conducted to examine whether GST-NS1I-1 is also recognized by the more divergent NS1 proteins of the avian influenza strains Aduck/Alberta/76 and A/turkey/Oregon/71. The NS1 proteins of these strains are 66.5 and 63.6 identical, respectively, to A/WSN/33. Significantly, NS1 of A/turkey/Oregon/71 is only 124 amino acids in length, lacking most of the carboxy-terminal half of other NS1 proteins, which consist of 207 to 237 amino acids (Norton, et al., 1987, Virology 156: 204–213). Nevertheless, precipitation of a protein band co-migrating with NS1 from both strains was observed (FIGS. 15A and 15B, lanes "GST-K5"). The NS1 and M1 proteins of A/duck/Alberta/76 could not be separated by the gel system used. Significant amounts of nucleoprotein in the GST-NS1I-1 precipitates of these avian strains were reproducibly detected for undetermined reasons.

Finally, the co-precipitation assay was used to test the human influenza B virus B/Lee/40. Surprisingly, GST-NS1I-1 precipitated specifically the influenza B virus NS1 protein, although it is only 20.6 identical to NS1 from A/WSN/33 (FIG. 15, Panel E, lane "GST-K5 "). Taken together, the binding of GST-NS1I-1 to NS1 proteins expressed by several influenza A and B virus stains could be demonstrated, despite the great divergence of their primary structures. This result strongly supports an important function of this interaction during the viral life cycle, and indicates that the NS1I-1 interaction is an excellent target for antiviral intervention.

8. EXAMPLE

THE IDENTIFICATION OF NS1-BINDING PROTEIN (NS1-BP) AND IT INTERACTION WITH INFLUENZA NS1 PROTEIN

In the example described below, the yeast interactive trap system (Gyuris, et al., 1993, Cell 75: 791–803; Zervos, et al., 1993. Cell 72: 223–232) was used to screen for cellular proteins that interact with the NS1 protein and to identify and characterize a human 70 kDa protein, termed NS1-binding protein (NS1-BP), which interacts with the non-structuial NS1 protein of the influenza A virus. The genetic interaction was confirmed by the specific coprecipitation of the NS1 protein from solution by a GST-NS1-BP fusion protein and glutathione Sepharose in vitro. NS1-BP contains an N-terminal BTB/POZ domain and five kelch-like tandem repeat elements of 50 amino acids.

In non-infected cells, affinity-purified antibodies localized NS1-BP in discrete nuclear domains which are enriched in spliceosome assembly factor SC35, a pre-mRNA splicing factor. This suggests an association of NS1-BP with the cellular splicing apparatus. However, in influenza A virus-infected cells, NS1-BP relocalized throughout the nucleoplasm and appeared distinct from the SC35 domains which suggests that NS1-BP f3nction may be disturbed or altered. The addition of a truncated NS1-BP mutant protein inhibited pre-mRNA splicing in HeLa cell nuclear extracts in vitro, possibly as the result of a dominant-negative effect on the endogenous protein, but it did not inhibit spliceosome assembly. These results suggest a role for NS1-BP in pre-mRNA splicing and support a model in which the NS1/NS1-BP interaction has a role in mediating the splicing-inhibitory effect of the NS1 protein.

8.1. MATERIALS AND METHODS 8.1.1. VIRUSES, CELLS AND EXTRACTS

Influenza A/WSN/33 virus was grown in the allantoic cavity of 10-day-old embryonated chicken eggs. HeLa, Hep-2 and 293 cells were passaged in Dulbecco's modified Eagle's tissue culture medium (D-MEM) containing 10 fetal calf serum. For immunoblot analysis, confluent cell monolayers grown in 35 mm dishes were lysed in RIPA buffer containing 150 mM NaCl, 1.0 Nonidet P-40, 0.5 deoxycholate, 0.1 sodium dodecyl sulfate, 50 mM Tris/HCl, pH8.0. Lysates were clarified by centrifugation for 10 min at 13,000 g and supernatants were used for immunoblot analysis.

8.1.2. YEAST STRAINS, E. COLI STRAINS AND PLASMIDS

E. coli strains used for cloning and expression were MH3 (trpC araD lacX hsdR galU galK), DH5 (F⁻ Φ8odlacZΔM15 Δ(lacZYA–argF)U169 deoR recA1 endA1 hsdR17($r_K^-m_K^+$) supE44λ⁻thi-1 gyrA96 relA1), BL26 (F⁻ ompT hsd$S_B$ ($r_B^-m_B^-$) gal dcm) and XL1 Blue recA1 endA1 gyrA96 thi-1 hsdR17 supE44 rel A1 lac {F' pro AB lacIqZΔM15 TnlO (Tet$^{\vee}$)}. Saccharomyces cerevisiae EGY48 (Mata trp1 ura3 his3 LEU2::pLEX-Aop6-LEU2), plasmids pSH18–34, pRFHM1 and the HeLa cell cDNA expression library constructed in pJG4–5 were kindly provided by R. Brent (Harvard Medical School) and have been described previously (Gyuris, et al., 1993, Cell 75: 791–803; Zervos, et al., 1993, Cell 72: 223–232). The constructions of plasmids pLexA-NS1, pcDNA3-NS1 and pGEX-NS1 have been described elsewhere (Wolff, et al., 1996, J. Virol. 70: 5363–5372). SP6-MNX (Zilimann, et al., 1988, Mol. Cell. Biol. 8: 814–821) was used as a template for transcription of synthetic pre-mRNA. Construction of plasmids followed standard cloning procedures (Ausubel, et al., 1992, Current protocols in molecular biology. John Wiley & Sons, New York). Plasmid pGEX-NS1-BP was made by subcloning the HeLa cDNA from the library plasmid (see below) into pGEX-SX-1 (Pharmacia). The bacterial expression plasmids pGEX-NS1-BP-REP and pMAL-NS1-BP-REP were generated by inserting NS1-BP cDNA corresponding to amino acids 1–368 (nucleotide positions 1 to 1104) between the EcoRI/XhoI-sites of pGEX-5X-1 (Pharnacia) and the EcoRI/SalI-sites of pMAL-c2 (New England Biolabs), respectively.

8.1.3. IDENTIFICATION AND ISOLATION OF NS1-INTERACTING cDNA CLONES USING THE YEAST INTERACTION TRAP

The yeast interaction trap was used to identify and to isolate HeLa cell cDNAs encoding NS1 binding factors as was previously described (Wolff, et al., 1996, J. Virol. 70: 5363–5372). In brief, EGY48 was transformed with the bait plasmid pLexA-NS1 and the lacZ reporter plasmid pSHl18–34. Subsequently, this strain was transformed with a plasmid library, in which HeLa cell cDNAs were conditionally expressed as fusions with an acidic activation domain from a GAL1 promoter. $3.3 \times 10^5$ primary transformants were screened for interaction as determined by their ability to grow on minimal synthetic medium in the absence of leucine and to activate the lacZ reporter gene specifically on plates containing galactose but not glucose. The library plasmid p59-1 was isolated from one selected clone by transformation in E. coli MH3 as described elsewhere (O'Neill, et al., 1994, Virology 206: 116–125). The specificity of the interaction was examined by retransformation of p59-1 into EGY48-harbouring pSH18–34 together with pLexA-NS1 or with pRFHM1, which expresses an unrelated fusion of LexA with the bicoid protein of D. melanogaster. p59-1 activated the lacZ reporter gene specifically in the presence of galactose in combination with pLexA-NS1, but not with pRFHM1. p59-1 was sequenced using a standard chain termination protocol.

8.1.4. CLONING OF NS1-BP 5'-END cDNA cDNA corresponding to the 5'-end of NS1-BP mRNA was obtained by a 5'-RACE (rapid amplification of cDNA ends) procedure using a 5'RACE kit (Gibco-BRL). 2.5 pmol of the specific DNA oligonucleotide 59GSP1 (dCATTCCTCTCTGTTATAGCC (SEQ ID NO:31), corresponding to positions 1123 to 1142 of NS1-BP cDNA) was hybridized to 1 µg of HeLa poly(A)⁺-RNA to prime first strand cDNA synthesis by M-MLV reverse transcriptase. The cDNA was tailed with dC using terminal transferase. The product was used as a template to amplify double stranded cDNA by PCR with the nested primer 59GSP2 (dCCACCTGCAGCTATGAG (SEQ ID NO:32), positions 1108 to 1124) and the 5'RACE anchor primer. The resulting product was subcloned into pGEM-T (Promega) to generate pGEM-NS1-BP-5'RACE plasmids. The NS1-BP cDNA was sequenced by the standard dideoxy method.

8.1.5. NORTHERN BLOT ANALYSIS

1 µg of HeLa cell poly(A)⁺-RNA was electrophoresed on a 1 agarose-formaldehyde gel, transferred onto a Nytran (Amersham) nylon membrane and immobilized by UV-crosslinking. A $^{32}$P-labeled NS1-BP-specific probe comprising positions 1038 to 2215 was used to detect NS1-BP MRNA by hybridization as described (Ausubel, et al., 1992, Current protocols in molecular biology. John Wiley & Sons, New York).

8.1.6. CO-PRECIPITATION OF NS1 PROTEIN WITH GST-NS1-HP BY GLUTATHIONE SEPHAROSE

NS1-BP (amino acids 347–619) was expressed from pGEX-NS1-BP as a glutathione-S-transferase (GST) fusion protein in E. coli BL26. Synthesis of GST-NS1-BP was induced by addition of 1 mM isopropyl-β-D-galactopyranoside (IPTG). Bacterial cell lysate containing the GST-NS1-BP fusion protein was adsorbed to glutathione Sepharose (Pharmacia) according to the protocol supplied by the manufacturer. Contaminating proteins were removed by three washes with phosphate-buffered-saline (PBS). NS1 protein was synthesized and labeled with [$^{35}$S]-methionine in coupled 50 µl transcription/translation reactions (Promega-TNT, Promega) programmed with pcDNA3-NS1. The translation reaction was mixed with 10 µl coated glutathione Sepharose beads in 750 µl of HN100 buffer (20 mM Hepes, pH8.0, 100 mM NaCl, 0.01 Nonidet P40 [NP-40]) for 2 h at 4° C. The beads were washed three times with PBS/ 0.01 NP-40 and the precipitated proteins were separated by SDS gel electrophoresis and visualized by autoradiography.

8.1.7. ANTI-NS1-BP-SERUM AND IMMUNOBLOT ANALYSES

The GST-NS1-BP-REP fusion protein carrying amino acids 1–368 of NS1-BP was expressed in E. coli BL26 transformed with pGEX-NS1-BP-REP and affinity-purified on glutathione Sepharose resin (Pharmacia) as recommended by the manufacturer. A six month old female rabbit was immunized with 400 μg purified GST-NS1-BP-REP fusion protein in complete Freund's adjuvant followed by booster injections of 250 μg fusion protein in incomplete adjuvant at a four week interval NS1-BP-specific antibodies were purified from serum by affinity-chromatography using an antigen-resin. For the construction of this matrix, a MAL-NS1-BP-REP fusion protein in which the maltose-binding protein of E. coli was fused to amino acids 1–368 of NS1-BP was expressed in E. coli XL1-Blue cells and affinity-purified on an amylose affinity column (New England Biolabs). The MAL-NS1-BP-REP fusion protein was immobilized on CNBr-activated Sepharose (Pharmacia) and the resulting resin was used for the affinity-purification of NS1-BP-specific antibodies as described elsewhere (Harlow, et al., 1988, Antibodies: A Laboratory Manual, Cold Spring Harbor Laboratory, Cold Spring Harbor, N.Y.). The purified antibodies were diluted 1:200 for immunoblot experiments using standard procedures (Harlow, et al., 1988, Antibodies: A Laboratory Manual, Cold Spring Harbor Laboratory, Cold Spring Harbor, N.Y.).

8.1.8. INDIRECT IMMUNOFLUORESCENCE MICROSCOPY

HeLa cells were grown to 50 confluency on glass cover slips in D-MEM containing 10 fetal calf serum. Where indicated, cells were infected at a multiplicity of 10 with influenza A/WSN/33 virus diluted in PBS for one hour at 37° C. Infection was continued under tissue culture medium at 37° C. Cells were processed for immunofluorescence analysis by fixation in 2.5 methanol-free formaldehyde (Polysciences Inc.) diluted in PBS and permeabilization of cells in 0.1 Triton X-100 was done as described (Wolff, et al., 1996, J. Virol. 70: 5363–5372). Cells were stained with primary antibodies diluted in PBS-3 bovine serum albumin. Affinity-purified anti-NS1-BP antibodies and the NS1-specific monoclonal antibody IA7 (a kind gift of Jonathan Yewdell, National Institutes of Health) were used at 1:100 dilutions. The anti-SC35 antibody (Fu, et al., 1990, Nature 343: 437–441) was purchased from Pharmingen Inc. and used at a dilution of 1:1000. The cells were washed and incubated with fluorescein isothiocyanate (FITC)-conjugated sheep anti-rabbit immunoglobulin G (IgG) and/or Texas Red-conjugated goat anti-mouse IgG. Subsequently, the coverslips were washed and mounted in MOWIOL 4–88 (Calbiochem) as described (Harlow, et al., 1988, Antibodies: A Laboratory Manual. Cold Spring Harbor Laboratory, Cold Spring Harbor, N.Y.). For conventional immunofluorescence analysis, cells were viewed on a Zeiss Axiovert 100 fluorescence microscope using a 63× objective and photographs were captured by a CF8/10× video camera (Kappa GmBH). A Zeiss LSM 410 Invert microscope equipped with a 100× objective lens was used for confocal laser scanning microscopy. Digitized images were pseudo-colored using PHOTOSHOP® software (Adobe Systems Inc.).

8.1.9. SPLICEOSOME ASSEMBLY AND SPLICING OF A $^{32}$P-LABELLED PRE-mRNA IN THE PRESENCE OF GST PROTEINS

GST GST-NS1 and GST-NS1-BP fusion proteins were expressed in E. coli BL26 and affinity-purified on glutathione Sepharose (Pharmacia) columns as recommended by the manufacturer. GST proteins were eluted with 20 mM glutathione in 50 mM Tris/HCl, pH 8.0, dialyzed versus buffer D (20 mM Hepes, pH 8.0, 100 mM KCl, 20 glycerol, 0.2 nM EDTA, 0.5 mM DTT) and stored at −80° C. The purity of the prepared proteins was tested by SDS gel electrophoresis and staining by Coomassie Blue. HeLa cell nuclear extract was prepared as described (Dignam, et al., 1983, Nucleic Acids Res. 11: 1475–1489). $^{32}$P-labelled MINX pre-mRNA was synthesized as described (Wolff, et al., 1992, EMBO J. 11: 345–359). In a typical splicing reaction 4 ng of pre-mRNA were incubated in a 100 μl volume containing 40 HeLa cell nuclear extract, 3.2 mM MgCl$_2$, 0.5 mM ATP, 20 mM creatine phosphate, 60 mM KCl. 8 μg of GST or equimolar amounts of GST fusion proteins were added where indicated and the reactions were incubated at 30° C. The formation of splicing complexes was analyzed after treatment with heparin (1 mg/ml) by electrophoresis on native acrylamide/agarose gels (Nelson, et al., 1988, Genes Dev. 2: 319–329). For RNA analysis, splicing products were purified and analyzed by electrophoresis on denaturing 13 acrylamide-urea gels.

8.1.10. SEQUENCE COMPARISONS

The NS1-BP cDNA and its derived amino acid sequence were compared to the GenBank and EMBL databases using the FASTA and TFASTA software (Deveraux, et al., 1984, Nucleic Acids Res. 12: 387–395). The PILEUP and PRETTY programs of the Genetics Computer Group (University of Madison, Wisconsin) were used to align the repeat elements of NS1-BP and to create a consensus sequence.

8.2. RESULTS

8.2.1. ISOLATION OF NS1 BINDING FACTORS

The yeast interaction trap system (Gyuris, et al., 1993, Cell 75: 791–803: Zervos, et al., 1993, Cell 72: 223–232) was used to identify cellular proteins that bind to the NS1 protein of the influenza A virus (Wolff, et al., 1996, J. Virol. 70: 5363–5372). A constitutively expressed LexA-NS1 fusion protein was used to screen a HeLa cell cDNA plasmid library, in which cDNA-encoded proteins were conditionally expressed as translational fusions with an acidic activation domain from a GAL1 promoter. Expression of the acidic domain fusion proteins is induced in the presence of galactose and repressed by glucose. 3.3×10$^5$ primary yeast transfoimants were screened for the galactose-dependent activation of LEU2 and lacZ reporter genes, which are regulated by LexA-specific operator sites. Three library plasmids were isolated from selected transformants that reproduced the interacting phenotype upon retransformation with pLexA-NS1, but not with the control plasmid pRFHM 1. The analysis of the human cDNA isolated through one of these library plasmids, p59-1, which encodes a novel human protein, NS1-BP is described in the following subsections.

8.2.2. CLONING AND ANALYSIS OF NS1-BP cDNA p59-1 had a 1.2 kb cDNA insert containing one long open reading frame of 819 bp followed by 338 bp of an untranslated region that terminated in a run of 20 adenosines (FIGS. 16A–16C). Northern blot analysis of HeLa cell poly(A)-RNA was used to determine if the size of the isolated HeLa cDNA corresponded to a complete copy of NS1-BP mRNA. A $^{32}$P-labeled NS1-BP-specific probe hybridized mainly to an RNA species of approximately 3.1 kb in size (FIG. 17). This result suggested that p59-1 carried an incomplete copy of NS1-BP mRNA. A 5'RACE (rapid amplification of cDNA ends) procedure to generate cDNA derived from the 5'- end of NS1-BP mRNA was employed. The RACE-products were subcloned and six resulting plasmid clones were isolated and sequenced. The longest 5'RACE clone extended the NS1-BP cDNA to a total of 2752 bp (FIGS. 16A–16C). Sequence analysis revealed the presence of one long open reading frame of 1857 nucleotides that encodes a 619 amino acid protein with a predicted molecular mass of 69.7 kDa. The initiator ATG codon of the open reading frame is in a sequence context which is compatible with being a translational start site (Kozak, 1989, J. Cell Biol. 108: 229–241). Analysis of the sequence of NS1-BP revealed the presence of five imperfect repeat elements of 47–49 amino acids at the C-terminal region between amino acids 368 to 607 (FIG. 18). These tandem repeats are 18 to 41 identical to each other and five positions are invariant between domains.

The cDNA and the deduced amino acid sequence of NS1-BP were compared to sequences in the GenBank and EMBL databases using the FASTA and TFASTA algorithms (Deveraux, et al., 1984, Nucleic Acids Res. 12: 387–395). Two regions of NS1-BP were identified which had homology to other proteins. First, the N-terminal ~120 amino acids of NS1-BP are homologous to the BTB (bric-a-brac, tramtrack, broad complex)/POZ (poxviruses and zinc fingers) domain that was identified in several zinc finger proteins known to act as transcriptional regulators (Bardwell, et al., 1994, Genes Dev. 8: 1664–1677; Zollmann, et al., 1994, Proc. Natl. Acad. Sci. USA 91: 1071–7–10721). Second, the five tandem repeats located between NS1-BP residues 368 and 607 are homologous to the 50 amino acid kelch motif that was originally found in the Drosophila Kelchprotein (Bork, et al., 1994, J. Mol. Biol. 236: 1277–1282; Xue, et al., 1993, Cell 72: 681–693). The Kelch protein is a component of the intercellular ring canals in the Drosophila egg chamber. Its function is required for the development of fertile oocytes since mutations in the kelch gene can cause a sterile phenotype in females (Xue, et al., 1993, Cell 72: 681–693). Interestingly, the Kelch protein also contains a predicted BTB/POZ domain. In total, the NS1-BP is 31 identical in amino acid sequence to Kelch.

Several other proteins were identified which have both kelch and BTB/POZ domains. These include the murine ENC-1 protein which is specifically expressed in the nervous system (Hernandez, et al., 1997, J. Neurosci 17: 3038–3051), human and bovine calicin, components of the mammalian sperm head (von Bülow, et al., 1995, Exp. Cell. Res. 219: 407–413), the predicted product of the human KIAAO132 gene (Nagase, et al., 1995, DNA Res. 2:167–174) and the proteins encoded by genes of vaccinia virus (A55R, C2L, and F3L) (Goebel, et al., 1990, Virology 179: 247–266), the Shope fibroma virus (T6, T8 and T9) (Upton, et al., 1990, Virology 179: 618–631), variola major virus (D16L, C7L, J6R, B20R) (Massung, et al., 1994, Virology 201: 215–240) and swine pox virus (C4L, C13L) (Massung, et al., 1993, Virology 197: 511–528). The functions of the viral gene products are not known. Several cellular kelch-repeat proteins containing no BTB/POZ domains were found, including the α- and β-scruin proteins which are expressed in the sperm of the horseshoe crab *L. polyphemus* (Way, et al., 1995, J. Cell Sci. 108: 3155–3162; Way, M., et al., 1995. J. Cell Biol. 128: 51–60), the products of the mouse intracisternal A particle-promoted placenta (MIPP) gene (Chang-Yeh, et al., 1991, Nucl. Acids Res. 19: 3667–3672) and the spe26 gene of *C. elegans* (Varkey, et al., 1995, Genes Dev. 9:1074–1086).

8.2.3. THE NS1 PROTEIN BINDS TO NS1-BP IN VITRO

To confirm the interaction of NS1 and the NS1-BP in vitro, binding assays were erformed. NS1-BP cDNA isolated through the library plasmid in the interaction trap screen (corresponding to NS1-BP amino acids 347–619) was fused to the glutathione-S-transferase (GST) gene in a bacterial expression vector. GST-NS1-BP fusion protein was expressed in *E. coli* and adsorbed to glutathione Sepharose beads. As a control, glutathione Sepharose eads were prepared that were complexed with GST protein alone. The NS1 protein was synthesized in vitro and labeled with $^{35}$S-methionine through coupled transcription/translation reactions in reticulocyte lysates. The coated glutathione Sepharose beads were incubated with the radiolabeled NS1 protein. The NS1 protein was efficiently precipitated by the GST-NS1-BP fusion protein, but not by GST (FIG. 19, lanes GST, GST-NS1-BP). This result confirms the yeast two hybrid data and shows that the viral NS1 protein can also physically interact with the cellular NS1-BP.

8.2.4. NS1-BP IS CONCENTRATED IN INTRA-NUCLEAR DOMAINS ENRICHED IN SPLICING FACTORS

Polyclonal rabbit antibodies were raised against recombinant NS1-BP and used to analyze the concentration and intracellular localization of NS1-BP in mammalian cells. Immunoblot analyses of the human epithelial-derived Hep-2, 293 and HeLa cell lines by NS1-BP-specific antibodies detected a protein doublet band with a molecular mass of about 70 kDa (FIG. 20). This is the predicted size for a protein derived from the NS1-BP open reading frame. Two minor protein bands migrating at 65 kDa and 50 kDa were stained at variable intensity and may correspond to NS1-BP break-down products. NS1-BP-specific antibodies were affmity-purified from immune serum and used for immunofluorescence analysis. In HeLa cells, a punctate nuclear staining pattern that excluded the nucleoli was observed (FIG. 21). In addition, a weak diffuse staining of the cytoplasm was reproducibly seen. The nuclear staining of NS1-BP was similar in appearance to the 'speckled' pattern that was obtained by immunofluorescence staining of cells with antibodies directed against factors involved in pre-mRNA splicing (Spector, et al., 1991, EMBO J. 10: 3467–3481). The speckle domains correspond ultrastructurally to interchromatin granules and perichromatin fibrils and are enriched in splicing snRNPs and non-snRNP splicing factors like SC35 and other SR proteins (reviewed by Spector, 1993, Annu. Rev. Cell Biol. 9: 265–315). To determine how the NS1-BP localization relates to speckle domains HeLa cells were double immunostained with NS1-BP-specific antibodies and a monoclonal antibody raised against the spliceosome assembly factor SC35 which is a known component of speckle domains (Fu, et al., 1990, Nature 343: 437441). Confocal laser scanning microscopy demonstrated that the dot-like nuclear NS1-BP signal colocalized with the SC35 signal (FIG. 22 A–C). The concentration of multiple proteins involved in pre-mRNA rocessing in these nuclear regions suggests an important role of this compartment for cellular RNA biogenesis (Singer, et al., 1997. Cell 91: 29.1–294). The accumulation of NS1-BP in the same compartment suggests that NS1-BP may be a component of the cellular splicing machinery.

8.2.5. NS1-BP RELOCALIZES TO THE ENTIRE NUCLEOPLASM IN INFLUENZA A VIRUS-INFECTED CELLS

The viral NS1 protein accumulates in the nucleus of cells infected with influenza A virus (Greenspan, et al., 1988, J. Virol. 62: 3020–3026, Young, et al., 1983, Proc. Natl. Acad. Sci. USA 80: 6105). Hence, experiments were performed that examined whether the speckled nuclear localization of the cellular NS1-binding protein would be affected in virus-infected cells expressing the NS1 protein. Influenza A virus-infected cells were double immunostained with antibodies directed against the NS1-BP and the viral NS1 or the cellular SC35 protein, respectively (FIGS. 22A–22I). As expected, the NS1 protein localized predominantly to the nucleoplasm with some additional nucleolar signal (FIG. 22E). For the NS1-BP staining, a remarkable change was observed after infection by influenza virus. The cellular NS1-BP was no longer found concentrated in the nuclear speckles, but was instead distributed throughout the nucleoplasm. Its distribution pattern was similar to that of the viral NS1 protein except that there was no nucleolar signal (FIGS. 22D and 22F). This redistribution of NS1-BP was observed in a few cells as early as four hours post infection. With ongoing infection, most of the cells expressing the viral NS1 protein had an NS1-BP staining pattern similar to the one shown in FIG. 22D. The intensity of the nuclear NS1-BP signal appeared to increase slightly in infected cells. However, no increase in the amount of NS1-BP in virus-infected cells by immunoblotting (data not shown) was detected. This suggests that NS1-BP epitopes are more easily accessible to antibodies in the nuclei of infected cells.

The intranuclear relocalization of NS1-BP in infected cells raised the question of whether the distribution of other proteins that normally localize to speckles would also change. Gross redistribution of proteins might occur if speckles break down during influenza virus infection. However, the staining of virus-infected cells with anti-SC35 antibody at 10 hours post infection (FIG. 22H) showed only a small change of the normal pattern. The average size of the speckles appeared to be slightly decreased with a concomitant increase in the number of these domains. Essentially the same observation was made in a previous study that examined the distribution of splicing factors in influenza A virus-infected cells (Fortes, et al., 1995, J. Gen. Virol. 76: 1001–100). These findings suggest that the redistribution of NS1-BP to the nucleoplasm in infected cells is not merely a consequence of speckle disintegration. The cellular NS1-BP may therefore be relocalized via the binding to the viral NS1 protein. The intracellular relocalization is likely to have an impact on NS1-BP finction in virus-infected cells.

8.2.6. A TRUNCATED NS1-BP PROTEIN INHIBITS PRE-mRNA SPLICING AT A STEP AFTER SPLICEOSOME ASSEMBLY

It has been demonstrated that the NS1 protein can inhibit pre-mRNA splicing in vivo and in vitro (Fortes, et al., 1994, EMBO J. 13: 704–712; Lu, et al., 1994, Genes Dev. 8:1817–1828). The block in splicing was assigned to a step after the assembly of spliceosomes, but before the first catalytic event (Lu, et al., 1994; Genes Dev. 8:1817–1828). It was hypothesized that the binding of the NS1 protein to a cellular protein(s) whose function is essential for splicing, leads to the observed block in splicing. Given the intranuclear colocalization of the NS1-binding protein with well-known factors of the mRNA splicing apparatus, the role of NS1-BP in pre-mRNA splicing was analyzed through the use of in vitro splicing assays using HeLa cell nuclear extracts. A truncated NS1-BP in form of a GST-NS1-BP fusion protein was used as a potential dominant-negative inhibitor of the endogenous NS1-BP. Such a strategy has previously been employed to examine a functional role of a protein in RNA splicing (Yuryev, et al., 1996, Proc. Natl. Acad. Sci. USA 93: 6975–6980).

The splicing of a $^{32}$P-labeled pre-mRNA in HeLa cell nuclear extracts was analyzed in the presence of GST-NS1-BP, GST-NS1 or control GST protein (FIG. 23). The formation of heparin-resistant splicing complexes in the same reactions by native gel electrophoresis was also examined. In the control reaction, the intron lariat-exon2 splicing intermediate was easily detected after a one hour incubation. At the two hour time point the accumulation of spliced MRNA and the intron lariat was observed (FIG. 23A, lanes NE). Native gel electrophoresis showed that both A- and B-type spliceosomes were formed normally at 20, 40 and 60 minutes with a higher proportion of radiolabeled mRNAs shifting into B complex bands at later time points (FIG. 23B, lanes NE). The A complex contains U2 snRNP and the B complex, which represents the fully assembled spliceosome, the U2, U4/U6 and US snRNPs (Konarska, et al., 1987, Cell 49: 763–774). The addition of GST protein to nuclear extract did not change the splicing of the pre-mRNA nor did it interfere with the assembly of spliceosomes (FIG. 23A and B, lanes GST). However, no splicing intermediates or products accumulated in the presence of equimolar amounts of affinity-punfied GST-NS1 protein (FIG. 23A, lanes GST-NS1). This effect was not due to a defect in spliceosome assembly, because both A- and B-type complexes assembled, although B bands formed at a slightly reduced rate (FIG. 23B, lanes GST-NS1). Interestingly, an almost identical result was obtained in splicing reactions complemented with the same concentration of purified GST-NS1-BP. There were no splicing products detectable after one hour incubation and only trace amounts of the exon 1 and intron lariat-exon2 splicing intermediates were detected at the two hour time point (FIG. 23A and B, lanes GST-NS1-BP). The RNP gel analysis showed that the formation of B-type splicing complexes occurred in the presence of GST-NS1-BP (FIG. 23B, lanes GST-NS1-BP and GST-NS1). This result demonstrates that the truncated NS1-BP protein blocks a cellular activity required for the first step of pre-mRNA splicing as does the viral NS1 protein. The observed splicing inhibition by the truncated NS1-BP is likely to be the result of a dominant-negative effect. on the splicing function of the endogenous wild-type protein.

8.3. DISCUSSION

The NS1 is the only non-structural protein of influenza A viruses that is expressed in infected cells. Although the NS1 protein has been implicated in several different processes including pre-mRNA splicing, mRNA transport and translation, little is known about specific cellular factors that are recognized by NS1. Since NS1 has pleiotropic effects, it may interact with a variety of proteins in infected cells thereby affecting different steps of cell metabolism. For example, NS1 appears to be an auxiliary (virulence) factor that plays a crucial role in inhibiting interferon-mediated antiviral responses of the host. Genetically engineered influenza A virus lacking the NS1 gene show impaired ability to replicate in normal host cells with functional interferon-defense systems, but are able to replicate in interferon-deficient host cells. The role of NS1 in the interferon-mediated response makes NS1/host cell protein interactions excellent targets for therapeutic intervention.

In order to identify such cellular proteins, the yeast interaction trap was used, as described supra, to screen a human CDNA expression library using a LexA-NS1 fusion protein as bait. NS1-I (NS1-interactor) which is a cytoplasmic 55 kDa protein that binds to the divergent NS1 proteins expressed by influenza A and B viruses has been previously characterized (Wolff, et al., 1996, J. Virol. 70: 5363–5372). NS1-I is derived from the precursor protein of a 17β-estradiol dehydrogenase and its binding to NS1 may have a function in modulating steroid hormone levels in virus-infected cells (Wolff, et al., 1996. J. Virol. 70: 5363–5372). This example demonstrates the identification ofthe NS1-binding protein, NS1-BP, through its specific interaction with the NS1 protein. This interaction was confirmed by the use of an in vitro binding assay. The NS1 protein co-precipitated with a GST-NS1-BP fusion protein, but not with GST alone demonstrating that NS1 also physically binds to NS1-BP.

The analysis of the primary structure of the NS1-BP identified two regions with considerable homology to known proteins. The amino-terminal 120 amino acids of NS1-P are homologous to the BTB/POZ domain originally identified in a group of proteins that primarily regulate transcription (Bardwell, et al., 1994, Genes Dev. 8: 1664–1677; Zollmann, et al., 1994, Proc. Natl. Acad. Sci. USA 91: 10717–10721). This includes the human proto-oncogenes LAZ3/BCL6 and PLZF and the Drosophila Tramtrack, GAGA and Broad Complex proteins (for a review, see Albagli, et al., 1995 Cell Growth Diff. 6:1193–1198). It has been shown that the isolated BTB/POZ domains of bric a brac (bab), ZID, LAZ3/BCL6 and Kelch can mediate homo- and/or heterodimerization suggesting that BTB/POZ domains are a conserved protein-protein interaction motif (Bardwell, et al., 1994, Genes Dev. 8: 1664–1677; Chen, et al., 1995, Mol. Cell. Biol. 15: 3424–3429; Dhordain, et al., 1995, Oncogene 11: 2689–2697; Dong, et al., 1996, Proc. Natl. Acad. Sci. 93: 3624–3629; Robinson, et al., 1997, J. Cell. Biol. 138: 799–810). In the case of the bab protein, the first 51 amino acids of the BTB/POZ domain were found to be sufficient for dimerization (Chen, et al., 1995, Mol. Cell. Biol. 15: 3424–3429). Another function of this module may be protein targeting to specific nuclear domains, since the appearance of ZID, LAZ3/BCL6 and hZF5 proteins in 'nuclear dots' depended on the integrity of their BTB/POZ domains (Bardwell, et al., 1994, Genes Dev. 8: 1664–1677; Chen, et al., 1995, Mol. Cell. Biol. 15: 3424–3429; Dhordain, et al., 1995, Oncogene 11: 2689–2697; Dong, et al., 1996, Proc. Natl. Acad. Sci. 93: 3624–3629; Sugiura, et al., 1997, Biochem. Biophys. Acta 1352: 23–26).

The human CDNA isolated through the interaction trap encoded amino acids 347 to 619 of NS1-BP, which suggests that this region contains the binding site for the NS1 protein. This part of the NS1-BP almost entirely consists of five imperfect repeats of 47–49 amino acids that are homologous to the kelch repeat motif (Bork, et al., 1994, J. Mol. Biol. 236: 1277–1282). Based on phylogenetic sequence comparisons it was suggested that kelch repeats take on a conserved three-dimensional fold that was previously identified in procaryotic and eucaryotic enzymes (Bork, et al., 1994, J. Mol. Biol. 236: 1277–1282). A high resolution x-ray diffraction analysis for one of these enzymes, galactose oxidase of *D. dendroides*, revealed that each repeat element folds into a blade-like domain of four-stranded antiparallel β sheets. The blade-like domains are circularly arranged resulting in a β propeller structure (Ito, et al., 1991, Nature 350: 87–90). The sequence homology suggests that the five repeats of NS1-BP may also adopt a similar three-dimensional fold.

In spite of the conservation on the sequence level, kelch repeats appear to have diverged functions in the homologous proteins. In galactose oxidase of *D. dendroides*, the kelch repeat fold contains the catalytic center of the enzyme (Ito, et al., 1991, Nature 350: 87–90). On the other hand, the kelch elements of the β-scruin protein of *L. polyphemus* have been shown to bind to actin which lead. to the proposal, that kelch repeats may constitute an actin-binding domain (Schmid, et al., 1994, J. Cell. Biol. 124: 341–350; Way, et al., 1995, J. Cell Biol. 128: 51–60). However, other proteins that contain kelch repeats like the α-scruin or the calicin proteins were localized to intracellular regions that appear to be devoid of actin (von Bülow, et al., 1995, Exp. Ceil. Res. 219: 407–413; Way, et al., 1995, J. Cell Sci. 108: 3155–3162).

The proteins encoded by different. poxviruses that are homologous to NS1-BP have not been studied. The genes of the vaccinia virus A55R, C2L and F3L ORF products could be deleted without affecting viral replication in tissue culture and are therefore considered to be non-essential (Kotwal, et al., 1988, Virology 167: 524–537; Perkus, et al., 1991, Virology 180: 406–410). However, the presence of homologous proteins in different poxviruses argues for important roles of these proteins. For example, these gene products may increase virus virulence or otherwise play a role in infected animals.

By immunolocalization studies described in this example demonstrate that the NS1-BP is concentrated in discrete regions in the nucleus of non-infected cells. This intracellular distribution is compatible with a function of the NS1-BP in gene regulation. Confocal double-immunostaining analyses of cells has previously demonstrated that the NS1-BP co-localizes in a speckled pattern with the spliceosome assembly factor SC35 (Fu, et al., 1990, Nature 343: 437–441). Several immunolocalization studies have shown that a number of other factors involved in pre-mRNA splicing, among them the spliceosomal snRNPs, also accumulate in the 20 to 50 irregularly shaped SC35 domains termed 'speckles' (reviewed by Spector, D. L. 1993. Annu. Rev. Cell Biol. 9: 265–315). As shown by electron microscopic analysis, the speckle domains correspond to interchromatin granules and perichromatin fibrils (Fakan, 1994, Trends Cell Biol. 4: 86–90; Spector, et al., 1991, EMBO J. 10: 3467–3481). Different conclusions have been drawn about the functional significance of the accumulation of splicing factors in specific subnuclear compartments. Since speckle domains localize near genes that are transcribed and spliced, it was suggested that speckles constitute a compartment in which pre-mRNA is actively spliced (Xing, et al., 1995, J. Cell Biol. 6:1635–1647). However, nascent RNA polymerase II transcripts were detected by Br-UTP labeling in a random distribution throughout the nucleoplasm (Fay, et al., 1997, Exp. Cell Res. 231: 27–37). Since splicing is thought to occur co-transcriptionally it was concluded by this group that pre-mRNA is processed throughout the nucleoplasm. For the speckle domains, a role as a storage or recycling compartment that supplies splicing factors to transcription sites was also proposed (reviewed by Singer, et al., 1997, Cell 91: 291–294). In any case, the important role of speckle domains for cellular RNA biogenesis is emphasized by their dynamic appearance in response to alterations of cellular gene expression. Stress conditions like heat shock that result in inhibition of RNA splicing also induce apparent changes in the distribution of splicing factors (Bond, 1988, EMBO 7: 3509–3518; Spector, etal., 1991, EMBO J. 10: 3467–3481). The localization of the NS1-BP in nuclear regions that contain lugh concentrations of pre-mRNA splicing factors suggests a role for the NS1-BP in mRNA splicing.

The intranuclear localization of the NS1-BP was drastically-altered in influenza A virus-infected cells that expressed the NS1 protein. The speckled pattern was replaced by a rather homogenous distribution of NS1-BP throughout the nucleoplasm in a fashion similar to that observed for the viral NS1 protein. In contrast, only subtle changes were detected in the appearance of the SC35 protein in influenza A virus-infected cells. The relocalization of the NS1-BP is therefore apparently a specific effect and not the result of a disintegration of the SC35-enriched domains.

This idea is further supported by observations that stress conditions like heat-shock, serum starvation or the addition of actinomycin D which inhibits RNA polymerase II transcription, did not disrupt the colocalization of NS1-BP with SC35. Local changes in NS1-BP concentration in response to an influenza A virus infection may also influence its function.

The NS1 protein has previously been shown to inhibit pre-mRNA splicing in vitro and in vivo (Fortes, et al., 1994, EMBO J. 13: 704–712; Lu, et al., 1994, Genes Dev. 8:1817–1828). It was speculated that the inhibition of splicing would result in the retention of pre-mRNA in the nucleus of infected cells thereby increasing the concentration of MRNA cap structures available for cap-snatching by the viral RNA polymerase (Lu, et al., 1994, Genes Dev. 8:1817–1828). Alternatively, the activity of the NS1 protein may contribute to the observed regulated splicing of the viral mRNAs derived from segments 7 and 8 (Smith, et al., 1985, EMBO J. 4: 2313–2319; Valcarel, et al., 1991, J. Gen. Virol. 72: 1301–1308). Because the cellular NS1-BP is concentrated in nuclear regions enriched in pre-mRNA splicing factors and it relocalizes in virus-infected cells, the role of NS1-BP in pre-mRNA splicing in vitro examined. A truncated NS1-BP was used as a potential non-functional competitor of the endogenous protein in HeLa cell nuclear extract and the effects of this probe were compared to the known inhibition of pre-mRNA splicing by the NS1 protein. A similar experimental design has been used before by others to examine the role of the large subunit of RNA polymerase II in pre-mRNA splicing (Du, et al., 1997, J. Cell Biol. 136: 5–18; Yurev, A., et al., 1996. Proc. Natl. Acad. Sci. USA 93: 6975–6980). This example demonstrates that the truncated NS1-BP blocks the splicing of a $^{32}$P-labeled pre-mRNA in HeLa cell nuclear extracts at the same step as does the NS1 protein. Splicing complexes formed at only slightly reduced rates in the presence of each of the two proteins. However, the conversion of the pre-mRNA into splicing intermediates or products was highly reduced. This finding suggests that both proteins act on the same stage of the spliceosome pathway, i.e., they block an activity required for the first catalytic step. The shortened NS1-BP that was used lacks the 346 N-terminal amino acids of the wild-type protein and was fused to the 26 kDa GST protein. This mutant NS1-BP protein is therefore unlikely to retain the full activity of the wild-type protein. However, the truncated NS1-BP may still be able to interact with other essential splicing factors thereby preventing their association with the wild-type NS1-BP. These results are compatible with a role of the wild-type NS1-BP in pre-mRNA splicing.

In normal cells, NS1-BP is concentrated in intranuclear domains that are enriched with multiple splicing factors. This example demonstrates that the cellular NS1-BP is specifically relocalized in influenza A virus-infected cells that express the NS1 protein. Redistribution of NS1-BP is likely to alter its function or activity. The influenza A virus may thus inhibit host cell splicing in infected cells by the association of the viral NS1 protein with the cellular NS1-BP. The NS1 protein may either downregulate NS1-BP activity directly by blocking its normal association with spliceosomes. Alternatively, a mechanism can be envisioned, in which the viral NS1 protein removes the cellular NS1-BP from centers of active splicing thereby lowering its availability for participation in cellular mRNA splicing processes. In both models, the relocalization of NS1-BP may reflect its disrupted function. It has previously been suggested that the NS1 protein inhibits splicing by binding to U6 snRNA (Lu, et al., 1994, Genes Dev. 8:1817–1828; Qiu, et al., 1995, RNA 1: 304–316) which is a key component of the catalytic core within the spliceosome (Guthrie, 1991, Science 253: 157–163; Sharp, 1994, Cell 77: 805–815). The apparent inhibition of splicing by the NS1 protein through the binding to NS1-BP does not exclude an NS1-U6 interaction. It is estimated that at least 80–100 different factors are involved in pre-mRNA splicing (Green, 1991, Annu. Rev. Cell Biol. 7: 559–599; Sharp, 1994, Cell 77: 805–815). For that reason it has been difficult to dissect their dynamic and complex interactions during the assembly of a spliceosome and the catalysis of the splicing reaction. It is possible that interactions of the NS1 protein with both NS1-BP and U6 snRNA contribute to the inhibition of pre-mRNA splicing.

Like the influenza A virus NS1 protein, the essential ICP27 protein of herpes simplex virus type 1 (HSV-1) has been implicated in impairing cellular pre-mRNA splicing, possibly as part of a host cell shut-off mechanism (Hardy, et al., 1994, J. Virol. 68: 7790–7799). There appear to be parallels between lytic infections by influenza A virus and HSV-1. Similarly as shown for the NS1 protein, the ICP27 protein has been found to have pleiotropic regulatory effects. Roles for ICP27 in mRNA 3'-end processing (Brown, et al., 1995, J. Virol. 69: 7187–7195; McLauchlan, et al., 1992, J. Virol. 66: 6939–6945) and in mRNA export (Phelan, et al., 1997, J. Gen. Virol. 78: 3327–3331; Soliman, T. M., et al., 1997. J. Virol. 71: 9188–9197) were suggested in addition to an inhibitoiveffect on pre-mRNA splicing. Furthermore, the expression of ICP27 induces the redistriibution of SC35 and spliceosomal snRNPs from the known speckled pattern to few condensed intranuclear structures in which they colocalize with the ICP27 protein (Phelan, et al., 1993, Proc. Natl. Acad. Sci. USA 90: 9056–9060; Sandri-Goldin, et al., 1995, J. Virol. 69: 6063–6076). This pattern is basically the opposite to the situation observed in influenza A virus-infected cells. In this example, the number of SC35 domains appears to increase with a concomitant decrease in size (Fortes, et al., 1995, J. Gen. Virol. 76: 1001–1007) (this study) and in contrast to ICP27, the NS1 protein is localized throughout the nucleus in a diffuse pattern.

9. EXAMPLE

A PROLINE-RICH MOTIF WITHIN THE MATRIX PROTEIN OF RHABDOVIRUSES INTERACTS WITH CELLULAR WW-DOMAINS AND FUNCTIONS IN BUDDING

The matrix (M) protein of rhabdoviruses plays a key role in viral assembly and budding, however the precise mechanism by which M mediates these processes remains unclear. A highly conserved, proline-rich motif (PPxY or PY motif; where P-proline, Y-tyrosine and x-any amino acid) of rhabdoviral M proteins was found to be associated with a functional role in budding mediated by the M protein. Point mutations that disrupt the PY motif of the M protein of vesicular stomatitis virus (VSV) had no obvious effect on membrane localization of M, but instead lead to a decrease in the amount of M protein released from cells in a functional budding assay. Interestingly, the PPxY sequence within rhabdoviral M proteins was identical to that of the ligand which interacts with WW domains of cellular proteins. Indeed, far-western blotting demonstrated that the PY motifs of both VSV (PPPY) and rabies virus (PPEY) M proteins can interact specifically with WW domains of cellular proteins. Moreover, point mutations that disrupt the consensus PY motif of VSV or rabies virus M protein resulted in a significant decrease in their ability to bind to ellular WW domains. These properties of the PY motif of rhabdovirus M proteins are trikingly analogous to those of the late (L) budding domain identified in the gag-specific rotein p2b of Rous sarcoma virus (RSV). The results of the following example indicate hat rhabdoviruses usurp host proteins to facilitate the budding process, and that M-mediated budding of rhabdoviruses and gag-mediated budding of retroviruses have features in common.

This example demonstrates that a highly conserved PPxY motif at the amino termini of several rhabdoviral M proteins is important for viral budding. The PPxY motifs of both VSV and rabies virus M proteins were shown to interact specifically with WW domains of cellular proteins, including YAP. Mutations that disrupted the viral PPxY motifs of VSV and rabies virus M proteins also disrupted-their ability to interact with WW domains. Lastly, the PPxY motif of VSV M was shown to be important for the release of M protein from cells in a functional budding assay. Taken together, these results demonstrate that the M proteins of rhabdoviruses possess a proline-rich budding domain similar to the L domain found in the gag proteins of retroviruses, and that the budding domain of M may mediate its function through interactions with selected host proteins.

9.1. MATERIALS AND METHODS 9.1.1. CELLS AND VIRUSES

Stocks of CV-1 and BHK-21 cells were maintained in Dulbecco's Minimal Essential Medium (DMEM; Life Technologies) supplemented with 10 fetal calf serum (Hyclone). Vesicular stomatitis virus (Indiana serotype) was propagated in BHK-21 cells.

9.1.2. PLASMIDS

The M gene of VSV (Indiana serotype) was cloned by RT-PCR using primers flanking the open reading frame and containing an EcoRV (5') and XbaI (3') restriction endonuclease sites. The PCR product was inserted into the EcoR V/XbaI-digested pSP72 vector containing the bacteriophage T7 promoter (Promega) using standard protocols (Ausubel, et al., 1992, *Current Protocols in Molecular Biology*, John Wiley and Sons, New York). Briefly, total RNA was isolated from BHK-21 cells infected with VSV using the TRIzol reagent and protocol of the manufacturer (Life Technologies). Reverse-transcription was performed using AMV reverse transcriptase (Life Technologies), and PCR was performed using standard protocols with Vent DNA polymerase (New England Biolabs). PCR fragments encoding amino acids 1–74 of VSV M, 1–202, 1–69, and 1–52 of rabies M were inserted into the BamHI and EcoRI restriction sites of the vector pGEX-2TK (Pharmacia) for expression of gst fusion proteins. Oligonucleotide primers and standard PCR protocols were utilized to introduce point mutations within the PPxY motifs of VSV and rabies virus gst-M fusion proteins. All plasmids and introduced mutations were confirmed by restriction endonuclease digestion and DNA sequencing by the Sanger method (Sanger, et al., 1977, Proc. Natl. Acad. Sci. U.S.A., 74, 5463–5467.). Plasmid DNAs were maintained in either *E. coli* strain DH5alpha (Life Technologies) or strain SURE2 (Stratagene), and DNA was purified using the Qiagen purification system (Qiagen Inc.).

9.1.3. PURIFICATION OF M PROTEIN FROM VSV VIRIONS

Briefly, the supernatant was harvested from VSV infected BHK-21 cells at 36 hour post-infectionand clarified first at 2500 rpm for 10 min., and then at 3200 rpm for 10 min. The supernatant was then centrifuged at 36,000 rpm for 30 min. in an SW41 rotor. The virion pellet was then suspended in 400 μl of buffer containing 10 mM Tris pH=8.0, 0.25 M NaCl, 1.0 Triton-X100, and 0.2 mg/ml DTT and incubated at room temperature for 30 min. The sample was then centrifuged at 75,000 rpm for 2 hours in a TL-100 ultracentrifuge (Beckman). The supernatant fraction (S) was removed and stored at −70° C., while the pellet fraction (P) was suspended in 400 μl of the above buffer and then stored at −70° C.

9.1.4. PURIFICATION AND RADIOLABELING OF GST FUSION PROTEINS

All gst fusion proteins were expressed from the plasmid pGEX-2TK in *E. coli* SURE2 cells using the gst Gene Fusion System and the protocols of the manufacturer (Pharmacia). The labeling of the fusion proteins with $^{32}$P-gamma ATP (6000Ci/mmol; NEN Dupont) and far-western blotting were as described previously (Kaelin, et al., 1992, Cell, 70, 351–364, Chen and Sudol, 1995, Proc. Natl. Acad. Sci. USA, 92, 7819–7823).

9.1.5. BUDDING ASSAY

The budding assay was essentially performed as described in Justice, et al., 1995, J. Virol., 69, 3156–3160. Briefly, 35 mm dishes of CV-1 cells were infected with VvT7 (generously provided by B. Moss, National Institutes of Health), and then transfected with the appropriate plasmid using the DOTAP reagent (Boehringer Mannheim Corporation). At 2 hours post-transfection the cells were metabolically labeled with 150 μCi of $^5$SMet-Cys (NEN Dupont), and the cells and media were harvested at various times post-transfection. Cells were lysed in RIPA buffer (50 mM Tris pH=8.0, 150 mM NaCl, 1.0 NP-40, 0.5 deoxycholate, 0.1 SDS), while 900 μl of media was added to 100 μl of 10× NTE buffer (0.5 M Tris-HCl pH=7.5, 1.5M NaCl, 1.0 NP-40, 10 mM EDTA, 2.5 gelatin, and 0.2M sodium azide). Immunoprecipitation of both cells and media were performed using polyclonal antiserum directed against VSV M. Protein samples were fractionated by SDS-PAGE and visualized by autoradiography.

9.1.6. INDIRECT IMMUNOFLUORESCENCE

Sub-cellular localization of the VSV M protein was accomplished by indirect immunofluorescence. CV-1 cells expressing the M protein of VSV were fixed and permeabilized for 15 minutes in 2.5 formaldehyde/0.5 Triton X-100/PBS. The primary antibody was polyclonal anti-VSV M, while the secondary antibody was affinity purified goat-anti-rabbit conjugated to FITC (Boehringer Mannheim Corporation). Positive cells were visualized with the use of a Leica CLSM confocal microscope.

9.2. RESULTS 9.2.1. CONSERVATION OF THE PY MOTIF IN THE M PROTEIN OF RHABDOVIRUSES

A globular domain that mediates protein-protein interactions was identified recently and shown to be present in a wide range of cellular proteins involved in signal transduction, gene regulation, and cytoskeletal formation (Sudol, 1996, In Blundell, et al., (eds.), *Prog. Biophys. Molec. Biol*, Vol. 65, Elsevier Science Ltd., Great Britain, pp. 113–132). This domain, termed WW domain, is about 38–40 amino acids long and contains a number of conserved amino acids including two highly conserved tryptophans spaced 20–22 amino acids apart (Sudol, 1996, In Blundell, et al., (eds.), *Prog. Biophys. Molec. Biol.*, Vol. 65, Elsevier Science Ltd., Great Britain, pp. 113–132). The WW domain was shown to interact with a polyproline ligand having the core consensus sequence PPxY (Chen, et al., 1997, J. Biol. Chem., 272, 17070–17077; Einbond and Sudol, 1996, FEBS Lett., 384, 1–8). Of interest to us, is that this PPxY motif is highly conserved in the M proteins of various rhabdoviruses (Table III, below; Gill and Banerjee, 1986, Virology, 150, 308–312; Kiuchi and Roy, 1984, Virology, 134, 238–243; Rayssiguier, et al., 1986, Virus Res., 5, 177–190; Rose and Gallione, 1981, J. Virol., 39, 519–528). Not only is the primary sequence conserved, but also the relative location within the N-termini of these M proteins is maintained (Table III, below). In addition to the rhabdoviruses, the putative matrix proteins (VP4O) of both Ebola and Marburg viruses (filoviruses that were initially classified as rhabdoviruses) also contain the PPxY motif at their amino termini (Table III, below; Bukreyev, et al., 1995, Arch. Virol., 140, 1589–1600; Sanchez, et al., 1993, Virus Res., 29, 215–240). The highly conserved nature of the sequence and topology of the PPxY motif within these viral structural proteins implies an importance perhaps in the structure and/or function of these proteins.

9.2.2. VSV M PROTEIN INTERACTS WITH CELLULAR WW DOMAINS IN VITRO

Since the highly conserved PY motif present within rhabdoviral M proteins is identical to the sequence of the ligand which interacts with WW domains, it was determined whether the M protein of VSV could interact with WW domains of cellular proteins in a far-western blotting assay. To isolate the M protein from VSV virion, BHK-21 cells were infected with VSV, and progeny virions were purified from the supernatant as described (see Section 9.1 Materials and Methods). The virion preparation was divided into pellet (P) and soluble (S) fractions, and the viral proteins present within each fraction were analyzed by SDS-PAGE and visualized by staining with coomassie brilliant blue (FIG. 24A). As expected, the soluble fraction contained predominantly the two viral envelope-associated proteins G (glycoprotein) and M, while the pellet fraction contained the viral nucleocapsid (N) protein in addition to G and M (FIG. 24A). In addition to the soluble fraction of purified virions (VR), cell extracts from mock-infected (m) or VSV infected (V) BHK-21 cells were probed with $^{32}$P-labeled glutathione-S-transferase alone (gst), or a fusion protein consisting of gst and WW domain 1 (gstYAPWW1) from the mouse YAP (FIG. 24B). Following a 12 hour exposure of the film, the M protein (at approximately 30 kD molecular mass) from purified virions interacted strongly with gstYAPWW1, but not with gst alone (FIG. 24B, lanes VR). A longer exposure of the filter (FIG. 24C) demonstrated that the VSV M protein from infected cell extracts also interacted with the gstYAPWW1 probe (FIG. 24C, lane V), but not with gst alone (data not shown). A protein of 30 kD was not detected in the mock-infected cell extract (FIG. 24C, lane m). Instead, a protein of approximately 38 kD was observed in the mock-infected cell extract probed with gstYAPWW1 (FIG. 24C, lane m). The presence of this cellular protein was not unexpected, since it has been described previously as WBP-2; a cellular protein of unknown function that interacts with the WW domain of YAP (Chen and Sudol, 1995, Proc. Natl. Acad. Sci. USA, 92, 7819–7823). Interestingly, WBP-2 was not observed in the VSV-infected cell extract (FIG. 24C, lane V). WBP-2 was also not detected when probed with gst alone (data not shown). These data indicate that full-length M protein from VSV virions and VSV-infected cell extracts can interact with the WW domain of a cellular protein.

9.2.3. THE N-TERMINUS OF VSV M IS SUFFICIENT FOR INTERACTING WITH CELLULAR WW DOMAINS

To determine whether the N-tenninus of VSV M containing the PPxY motif was sufficient to mediate the interaction with the WW domains of YAP, the full-length M gene of VSV was first cloned by RT-PCR. Several plasmids were then constructed to express the N-terminal 74 amino acids of VSV M fused to the gst moiety (FIG. 25). The PPxY motif, which begins at amino acid position 24, was unmodified in plasmid gstVSVM74WT (FIG. 25). However, in plasmids gstVSVM74P-A and gstVSVM74Y-A proline (P) 24 was changed to alanine (A) and tyrosine (Y) 27 was changed to (A), respectively (FIG. 25). The gstVSVM74WT protein was expressed in *E. coli* grown under inducing (IN) conditions (FIG. 26A). Equivalent amounts of induced or uninduced bacterial extracts were immobilized onto nitrocellulose filters and probed with gstYAPWW2 (FIG. 26B, lanes 2 and 3), gstYAPWW1 (lanes 4 and 5), or gst alone (lanes 6 and 7). The gstVSVM74WT fusion protein interacted with both WW domains 1 and 2 from the mouse YAP, however a reproducibly stronger interaction was observed with WW domain 1 (FIG. 26B, compare lanes 2 and 4). A similar preference for WW domain 1 was also observed when full-length M protein from purified virions and VSV-infected cells extracts were assayed by far-western analysis. The gstVSVM74WT fusion protein did not interact with gst alone (FIG. 26B, lane 6).

To further confirm that the PY motif present within the N-terminal 74 amino acids of VSV M was responsible for this interaction, the fusion proteins containing point mutations within the PY motif were used in a similar far-western blotting assay. Mutations of the first P or Y in PPxY to alanine have been shown to result in a decrease in the efficiency of binding to WW domains (Chen and Sudol, 1995, Proc. Natl. Acad. Sci. USA, 92, 7819–7823; Chen, et al., 1997, J. Biol. Chem., 272, 17070–17077). The wild type and mutant gst fusion proteins were expressed to equivalent levels in *E. coli* (FIG. 27A) and probed with gstYAPWW2 (FIG. 27B). As expected, WW domain 2 of YAP interacted with the gstVSVM74WT protein (FIG. 27B, lane 1), however the ability of WW domain 2 of YAP to interact with either of the point mutants was reduced by 90 (FIG. 27B, lanes 2 and 3). The gstYAPWW2 probe did not interact with gst alone, and the gst probe did not interact with the wild type or mutant gstVSVM74 fusion proteins (data not shown). These data demonstrate that the N-terminal 74 amino acids of VSV M are sufficient for interacting with WW domains of YAP, and that the viral PPxY motif can serve as the core ligand for this cellular protein domain.

9.2.4. RABIES VIRUS M PROTEIN INTERACTS WITH CELLULAR WW DOMAINS IN VITRO

To determine whether a second rhabdoviral M protein (with limited overall sequence identity to M protein of VSV) could interact with WW domains, the full-length rabies virus M protein or various C-terminal truncations of rabies M were fused to gst (FIG. 28). The fusion protein gstRabM52Y-A is identical to gstRabM52WT except for a single point mutation in the PY motif of the rabies M protein which changes the tyrosine to an alanine (FIG. 28). All four gstRabM fusion proteins were expressed in *E. coli* grown under inducing conditions and used in far-western blotting assays (FIG. 29). Duplicate filters containing gstRabM202 and gstRabM69 were probed with either gst alone, or gstYAPWW2 (FIG. 29A). Both gstRabM202 and gstRabM69 fusion proteins interacted with the gstYAPWW2 probe (FIG. 29A, lanes 3 and 4), but not with gst alone (FIG. 29A, lanes 1 and 2). Identical amounts of gstRabM52WT and gstRabM52Y-A fusion proteins (as shown in FIG. 29B) were also probed with either gst alone, or gstYAPWW2 (FIG. 29C). The gstRabM52WT fusion protein interacted with gstYAPWW2 (FIG. 29C, lane 4), but not with gst alone (lane 2). In contrast, a single point mutation within the PPxY motif in protein gstRabM52Y-A completely abolished the interaction with the YAP WW domain (FIG. 29C, lane 3).

To examine further the rabies M protein and WW domain interaction, the rabies fusion proteins were now purified, quantitated, and labeled as probes against a panel of gstWW domain fusion proteins (FIG. 30). In addition to gst alone, equivalent amounts (as shown in FIG. 30C) of gstYAPWW1, gstYAP WW2, gstDystrophinWW, gstNedd4WW2, gstNedd4WW3, and gstFE65WW fusion proteins were probed with either gstRabM52WT (FIG. 30A), or gstRabM52Y-A (FIG. 30B). As expected, gstRabM52WT interacted with WW domain 2 and WW domain 1 (upon longer exposure of the filter) of YAP (FIG. 30A). Interestingly, gstRabM52WT also interacted strongly with WW domain 2 from the Nedd4 protein (FIG. 30A). The gstRabM52WT protein did not interact with the remaining gstWW domains fusion proteins demonstrating that there is specificity in this protein-protein interaction. Once again, the interactions between the rabies M protein and the various WW domains observed (FIG. 30A) were completely abolished by the introduction of a single point mutation in the PPxY motif in the gstRab52MY-A protein (FIG. 30B).

9.2.5. THE PY MOTIF OF VSV M FACILITATES BUDDING

A functional budding assay for VSV M has been described previously Justice, et al., 1995, J. Virol., 69, 3156–3160. This assay was utilized to determine whether the PPxY motif of VSV M protein is important in M-mediated budding. CV-1 cells were first infected with the recombinant vaccinia Vifus (VvT7) expressing the bacteriophage T7 polymerase, and then transfected with plasmid pT7VSVMWT (expressing fill-length, wild type M protein), plasmid pT7VSVMY-A (identical to wild type M except for a single point mutation within the PY motif changing tyrosine to alanine), or no DNA (mock-transfected). Both the cells and media were harvested and subjected to immunoprecipitation using polyclonal anti-VSV M antiserum (FIG. 31). Identical amounts of both wild type and mutant VSV M proteins were observed in the cell lysates (FIG. 31A, lanes 3 and 4), while no M protein was detected in niock-transfected cells (FIG. 31A, lane 2). In contrast, the amount of the mutant M protein (FIG. 31B, lane 3) released into the media by budding was reduced reproducibly by about 70% as compared to the amount of wild type VSV M protein in the media (FIG. 31B, lane 2). Thus, a single point mutation within the PPxY motif of VSV M resulted in a significant decrease in budding efficiency.

To determine whether the defect in budding of the mutant M protein was due to an inability to localize to the cell membrane, indirect immunofluorescence and confocal microscopy were performed on cells transfected with either the wild type or mutant M protein (FIGS. 32A–32C). Transfected cells were examined at 5, 8, and 10 hours post-transfection (data not shown for 5 and 10 hour time points). For all time points tested, both the wild type and mutant M proteins localized to the cytoplasmic membrane equally well (FIGS. 32A–32C). These data indicate that the defect in budding of the mutant M protein is not simply due to mislocalization within the cell, but rather to a defect in a later stage of the budding process.

9.3. DISCUSSION

Much progress has been made in studying the assembly and budding pathways of negative-sense RNA viruses in general, however many questions remain concerning the role of both viral and host proteins in these late stages of the viral life-cycle. With respect to rhabdoviral assembly and egress, the results described in Section 9.2, above, demonstrates that: (i) A highly conserved PPxY motif within the M protein of VSV and rabies virus can function as a ligand that interacts in vitro with WW domains of cellular proteins, and (ii) This same PPxY motif of VSV M protein is functionally important for the budding process. Taken together, these findings indicate that rhabdoviral budding mediated by the M protein is facilitated by viral-host interactions.

The polyproline ligand that interacts with the WW domain has been identified and well characterized as having the core consensus sequence PPxY. While the M protein of many rhabdoviruses maintain the PPxY motif at their amino-termini (Table III), it should be noted that the M proteins from several rhabdoviruses of fish possess a PPxH (H-histidine) motif rather than PPxY (Benmansour, et al., 1994, Virology, 198, 602–612). Although the aromatic nature of the amino acid position occupied by H rather than Y is maintained, this PPxH motif may also interact with either WW domains, or perhaps a WW-like domain. WW domains from YAP and the Nedd4 protein interacted strongly and specifically with the PPxY motifs of both VSV and rabies virus M proteins, whereas WW domains from other cellular proteins (dystrophin, FE65, and ESS 1) did not interact with either viral protein (FIG. 30 and data not shown). Single point mutations within the PPxY motifs of VSV M protein and rabies virus M protein were sufficient to either significantly reduce, or abolish interactions with cellular WW domains. Both the WW domains of YAP and of the Nedd4 protein were able to interact with the viral M proteins, and both YAP and Nedd4 can be found on the inner side of the plasma membrane, indicating that these cellular proteins represent authentic, in vivo targets for interacting with the rhabdoviral M protein.

Both the WW domain and the related SH3 domain have been implicated in mediating virus-host protein-protein interactions. The Nef protein of HIV-1 for example possesses a polyproline ligand which has been shown to interact with Src-family SH3 domains of cellular proteins and to be important for optimal viral replication (Lee, et al., 1995, EMBO J., 14, 5006–5015; Lee, et al., 1996, Cell, 85, 931–942). The LMP2 protein of Epstein-Barr virus (EBV) contains two polyproline motifs that have been postulated to mediate an interaction between LMP2 and the Src-family tyrqsine kinases, FYN and LYN (Longnecker, et al., 1991, J. Virol., 65, 3681–3692). Lastly, of particular interest to us, the PPxY motif is highly conserved in the gag proteins of many animal and human retroviruses (Wills, et al., 1994, J. Virol., 68, 6605–6618). One of the better characterized gag proteins in terms of functional domains important for gag-mediated budding, is that of Rous sarcoma virus (Bennett, et al., 1991, J. Virol., 65, 272–280; Bennett, et al., 1993, J. Virol., 67, 6487–6498; Craven, et al., 1993, J. Virol., 67, 6246–6252; Weldon, et al., 1990, J. Virol., 64, 4169–4179; Weldon, et al., 1993, J. Virol., 67, 5550–5561; Wills and Craven, 1991, AIDS, 5, 639–654; Wills, et al., 1991, J. Virol., 65, 3804–3812; Wills, et al., 1994, J. Virol., 68, 6605–6618). Elegant studies have demonstrated that the PPxY motif present within the p2b protein of RSV gag not only interacts with WW domains in vitro, but also functions as a late budding domain (L domain) which is essential for a late stage in retroviral assembly and release (Gamier, et al., 1996, Nature, 381, 744–745; Wills, et al., 1994, J. Virol., 68, 6605–6618). RSV gag proteins having mutations in the PPxY motif, or those deleted in this motif are defective in budding. Late budding domains have been identified in gag proteins of human immunodeficiency virus HIVl-1 and equine infectious anemia virus, and have been implicated in mediating interactions with host proteins (Gottlinger, et al., 1991, Proc. Nati. Acad. Sci. USA., 88, 3195–3199; Huang, et al., 1995, J. Virol., 69, 6810–6818; Puffer, et al., 1997, J.

Virol., 71, 6541–6546). For example, Tyr Xaa Xaa Leu is apparently the "budding motif" in the gag p⁹ protein of the equine infectious anemia virus. (Puffer, et al., 1997, J. Virol., 71, 6541–6546). A similar motif in the influenza virus M1 protein is Tyr Xaa Xaa Leu (aa 100–103).

represents a common step in the assembly pathways of rhabdoviruses, retroviruses, and filoviruses, it is tempting to speculate that antivirals which target this interaction may be effective against a variety of viral pathogens including Ebola and Marburg viruses.

TABLE III

| VIRUS | PROTEIN SEQ.[1] | | | POSITION[2] | SEQ ID NO: | ACCESSION #[7] |
|---|---|---|---|---|---|---|
| VSV (Ind.) | KLGIA | PPPY | EEDTS | 24–27 | 33 | X04452 |
| VSV (N.J.) | KKMGL | PPPY | DESCP | 24–27 | 34 | M14553 |
| Rabies[3] | DLWLP | PPEY | VPLKE | 35–38 | 35 | M31046 |
| PIRY | MEWES | PPSY | NEIKS | 33–36 | 36 | D26175 |
| S.V. of C.[4] | KSKGT | PPTY | EETLA | 17–20 | 37 | K02123 |
| Ebola[5] | ILPTA | PPEY | MEAIY | 10–13 | 38 | L11365 |
| Marburg[6] | MQYLN | PPPY | ADHGA | 16–19 | 39 | Z29337 |

[1] The sequence is derived from the matrix protein of VSV, rabies, Piry, and S.V. of C. viruses
The sequence is derived from the VP40 protein of Ebola and Marburg viruses.
[2] The numbers represent amino acid positions of the PY motif within the protein beginning from the N-terminus.
[3] This sequence (14 amino acids) of the rabies virus matrix protein is perfectly conserved in strains SAD B19,CVS, Nishigahara, ERA, and PV.
[4] Spring Viremia of Carp virus.
[5] Ebola virus (Zaire strain).
[6] Marburg virus (Popp strain).
[7] GenBank Accession number.

Thus, for the PPxY-containing gag proteins, it has been postulated that cellular proteins containing WW domains may play a role in the maturation and budding of these retroviruses (Garnier, et al., 1996, Nature, 381, 744–745). Our findings with the M protein of rhabdoviruses parallel those of RSV gag in that the PPxY motif of VSV M can also interact with WW domains and appears to be important in the budding process (FIGS. 31 and 32A–32C). These data provide further evidence that the M protein of rhabdoviruses and the gag protein of retroviruses are in many ways functionally equivalent. Indeed, the N-terminal 74 amino acids of VSV M protein containing the PPxY motif are capable of functionally replacing the L-domain of the p2b protein of RSV in a functional retroviral budding assay. Moreover, point mutations that altered the PPxY motif of VSV M in these chimeric M-gag proteins resulted in a protein that was defective in budding. Results from the initial immunofluorescence analyses (FIGS. 32A–32C) lend support to the idea that the PPxY motif of VSV M protein is not required for membrane localization, but rather appears to be required for a later step in the budding pathway. Thus, the PPxY motif of the VSV M protein likely functions as a rhabdoviral late budding domain.

Should the PPxY-WW domain interaction prove to be a crucial interaction between the virus and host in vivo, then this virus-host interaction could serve as a potential target for antiviral agents designed to disrupt or block this step of viral assembly and release. Since the WW domain and the core motif of its ligand are relatively short, one could speculate that such antiviral agents could be easily selected from chemical libraries of low molecular weight compounds (Sudol, 1997, Emerging therapeutic targets, Vol. 1, pp. 81–84). Also, if indeed the PPxY-WW domain interaction

10. EXAMPLE

INHIBITION OF GROWTH OF INFLUENZA A/WSN/VIRUS BY THE NP-SPECIFIC NLS OLIGOPEPTIDE

The yeast 2-hybrid assay has been used previously to identify the specific domains on the NP that bind to the NPI protein (Wang, et al., 1997, J. Virology 71(3): 1850–1856). Mutational analysis including alanine scanning identified the motifs Ser Xaa Gly Thr Lys Arg Ser Tyr Xaa Xaa Met (SEQ ID NO:40) and Thr Lys Arg Ser Xaa Xaa Xaa Met (SEQ ID NO:41). which are required for binding of NP to NPI-1 and NPI-3, respectively. These sequences were shown to possess nuclear localization signal (NLS) activity. In the present example, MDBK cells were infected at an m.o.i.=1 in the presence or absence of a 19-amino acid NP-NLS oligopeptide (Ala Ser Gln Gly Thr Lys Arg Ser Tyr Glu Gln Met Glu Thr Asp Gly Glu Arg Gln (SEQ ID NO:22); corresponding to amino acids 2–20 of NP) and an 11-amino-acid control peptide (Cys Gly Asp Leu Arg Leu Thr Leu Leu Glu Leu (SEQ ID NO:42)). Hemagglutination titer was measured at 24 hours p.i. At a concentration of 100 μm, the NP-NLS oligopeptide inhibits viral growth a thousand-fold.

The ability of different fragments of the NPI-1 protein to bind the NP-NLS peptide were analyzed. The region of NPI-1 primarily responsible for the binding of NPI-1 to the NP-NLS lies between aa 425–538 at the carboxy terminus of NPI-1, in the region of the STAT-1 binding domain.

These results demonstrate that peptides that correspond to the NP-NLS target site of the NPI-1 binding domain of NP can inhibit the interaction of NP with NPI proteins and can therefore be used to treat influenza infection.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for identifying a test compound that inhibits the interaction between an NS1-BP protein and an influenza virus NS1 protein, said method comprising:

a) contacting an NS1-BP protein or a peptide fragment of the NS1-BP protein comprising the binding site for an NS1 protein with an immobilized NS1 protein or a peptide fragment of the NS1 protein comprsing the binding site for an NS1-BP protein, under conditions and for a time sufficient to pemit the NS1-BP protein or NS1-BP peptide fragment to bind to and form a complex with the NS1 protein or NS1 peptide fragment;

b) removing unbound NS1-BP protein or NS1-BP peptide fragment; and c) detecting the complex, so if there is a decrease in the complex detected in c) as compared to the amount of complex detected in the absence of the test compound, a test compound that inhibits the interaction between an NS1-BP protein and an NS1 protein is identified.

2. A method for identifying a test compound that inhibits the interaction between an NS1-BP protein and an influenza virus NS1 protein, said method comprising:

a) contacting an NS1 protein or a peptide fragment of the NS1 protein comprising the binding site for the NS1-BP protein with an immobilized NS1-BP protein or a peptide fragment of the NS1-BP protein comprising the binding site for the NS1 protein, under conditions and for a time sufficient to permit the NS1 protein or NS1 peptide fragment to bind to and form a complex with the NS1-BP protein or NS1-BP peptide fragment, in the presence of test compound;

b) removing unbound NS1 protein or NS1 peptide fragment; and c) detecting the complex, so if there is a decrease in the complex detected in c) as compared to the amount of complex detected in the absence of the test compound, a test compound that inhibits the interaction between an NS1-BP protein and an NS1 protein is indentified.

3. A method for identifying a test compound that inhibits the interaction between an NS1-BP protein and an influenza virus NS1 protein, said method comprising:

a) contacting a fusion protein with an immobilized NS1 protein or a peptide fragment of the NS1 protein comprising the binding site of the NS1 protein, under conditions and for a time sufficient to permit the fusion protein to bind to and form a complex with the NS1 protein or NS1 peptide fragment, in the presence of test compound, wherein the fusion protein comprises an NS1-BP protein or a peptide fragment of the NS1-BP protein comprising the binding site for NS1 protein;

b) removing unbound fusion protein; and c) detecting the complex, so if there is a decrease in the complex detected in c) as compared to the amount of complex detected in the absence of the test compound, a test compound that inhibits the interaction between an NS1-BP protein and an NS1 protein is identified.

4. A method for identifying a test compound that inhibits the interaction between an NS1-BP protein and an influenza virus NS1 protein, said method comprising:

a) contacting a fusion protein with an immobilized NS1-BP protein or a peptide fragment of the NS1-BP protein comprising the binding site of the NS1 protein, under conditions and for a time sufficient to permit the fusion protein to bind to and form a complex with the NS1-BP protein or NS1-BP peptide fragment, in the presence of test compound, wherein the fusion protein comprises an NS1 protein or a peptide fragment of the NS1 protein comprising the binding site for NS1-BP protein;

b) removing unbound fusion protein; and c) detecting the complex, so if there is a decrease in the complex detected in c) as compared to the amount of complex detected in the absence of the test compound, a test compound that inhibits the interaction between an NS1-BP protein and an NS1 protein is identified. identified.

5. A method for identifying a test compound that disrupts the interaction between an NS1-BP protein and an influenza virus NS1 protein, said method comprising:

a) contacting an NS1-BP/NS1 protein complex with a test compound, wherein the NS1-BP/NS1 protein complex comprises an NS1-BP protein or a peptide fragment of the NS1-BP protein comprising the binding site for an NS1 protein, and an NS1 protein or a peptide fragment of the NS1 protein comprising the binding site for an NS1-BP protein; and b) detecting the NS1-BP/NS1 protein complex, so that if there is a decrease in the complex detected in b) as compared to the amount of complex detected in the absence of the test compound, a test compound that disrupts the interaction between an NS1-BP protein and an NS1 protein is identified.

6. A method for identifying a test compound that inhibits the interaction between an NS1-BP protein and an influenza virus NS1 protein, said method comprising:

a) contacting, in a reaction mixture, an NS1 protein or a peptide fragment of the NS1 protein comprising the binding site for an NS1-BP protein with an NS1-BP protein or a peptide fragment of the NS1-BP protein comprising the binding site for an NS1 protein, under conditions and for a time sufficient to permit the NS1 protein or NS1 peptide fragment to bind to and form a complex with the NS1-BP protein or NS1-BP peptide fragment, in the presence of test compound;

b) separating the complex from the reaction mixture; and c) detecting the complex, so if there is a decrease in the complex detected in c) as compared to the amount of complex detected in the absence of the test compound, a test compound that inhibits the interaction between an NS1-BP protein and an NS1 protein is identified.

7. A method for identifying a test compound that inhibits the interaction between an NS1-BP protein and an influenza virus NS1 protein, said method comprising:

a) contacting an NS1 protein or a peptide fragment of the NS1 protein comprising the binding site for an NS1-BP protein with an immobilized fusion protein, under conditions and for a time sufficient to permit the NS1 protein or NS1 peptide fragment to bind to and form a complex with the fusion protein, in the presence of test compound, wherein the fusion protein comprises an NS1-BP protein or a peptide fragment of the NS1-BP protein comprising the binding site for an NS 1 protein;

b) removing unbound NS1 protein or NS1 peptide fragment; and c) detecting the complex, so if there is a decrease in the complex detected in c) as compared to the amount of complex detected in the absence of the test compound, a test compound that inhibits the interaction between an NS1-BP protein and an NS1 protein is identified.

8. A method for identifying a test compound that inhibits the interaction between an NS1-BP protein and an influenza virus NS1 protein, said method comprising:

a) contacting an NS1-BP protein or a peptide fragment of the NS1-BP protein comprising the binding site for an NS1 protein with an immobilized fusion protein, under conditions and for a time sufficient to permit the NS1-BP protein or NS1-BP peptide fragment to bind to and form a complex with the fusion protein, in the presence of test compound, wherein the fusion protein comprises an NS1 protein or a peptide fragment of the NS1 protein comprising the binding site for an NS1-BP protein;

b) removing unbound NS1-BP protein or NS1-BP peptide fragment; and c) detecting the complex, so if there is a decrease in the complex detected in c) as compared to the amount of complex detected in the absence of the test compound, a test compound that inhibits the interaction between an NS1-BP protein and an NS1 protein is identified.

9. A method for identifying a test compound that inhibits the interaction between an NS1-BP protein and an influenza virus NS1 protein, said method comprising:

a) contacting, in a reaction mixture, an NS1-BP protein or a peptide fragment of the NS1-BP protein comprising the binding site for an NS1 protein with a fusion protein, under conditions and for a time sufficient to permit the NS1-BP protein or NS1-BP peptide fragment to bind to and form a complex with the fusion protein, in the presence of test compound, wherein the fusion protein comprises an NS1 protein or a peptide fragment of the NS1 protein comprising the binding site for an NS1-BP protein;

b) separating the complex from the reaction mixture; and c) detecting the complex, so if there is a decrease in the complex detected in c) as compared to the amount of complex detected in the absence of the test compound, a test compound that inhibits the interaction between an NS1-BP protein and an NS1 protein is identified.

10. A method for identifying a test compound that inhibits the interaction between an NS1-BP protein and an influenza virus NS1 protein, said method comprising:

a) contacting, in a reaction mixture, an NS1 protein or a peptide fragment of the NS1 protein comprising the binding site for an NS1-BP protein with a fusion protein, under conditions and for a time sufficient to permit the NS1 protein or NS1 peptide fragment to bind to the fusion protein and form a complex with, in the presence of test compound, wherein the fusion protein comprises an NS1-BP protein or a peptide fragment of the NS1-BP protein comprising the binding site for an NS1 protein;

b) separating the complex from the reaction mixture; and c) detecting the complex, so if there is a decrease in the complex detected in c) as compared to the amount of complex detected in the absence of the test compound, a test compound that inhibits the interaction between an NS1-BP protein and an NS1 protein is identified.

11. The method of claim 1 or 3, wherein the NS1 protein or NS1 peptide fragment is immobilized on a solid surface.

12. The method of claim 1, 6, 8, or 9, wherein the NS1-BP protein or NS1-BP peptide fragment is directly or indirectly labeled.

13. The method of claim 2 or 4, wherein the NS1-BP protein or NS1-BP peptide fragment is immobilized on a solid surface.

14. The method of claim 2, 6, 7, or 10, wherein the NS1 protein or NS1 peptide fragment is directly or indirectly labeled.

15. The method of claim 12, wherein the label is a radioisotope or an enzymatic label.

16. The method of claim 14, wherein the label is a radioisotope or an enzymatic label.

17. The method of claim 7 or 8, wherein the fusion protein is immobilized on a solid surface.

18. The method of claim 3, 4, 9, or 10, wherein the fusion protein is directly or indirectly labeled.

19. The method of claim 18, wherein the label is a radioisotope or an enzymatic label.

20. The method as in any one of claims 1–10, wheren the test compound is a peptide, antibody, or organic molecule.

21. The method of claim 7 or 8, wherein the fusion protein further comprises glutathione-S-transferase.

* * * * *